United States Patent [19]
Hu et al.

[11] Patent Number: 6,117,841
[45] Date of Patent: Sep. 12, 2000

[54] SUBSTITUTED PEPTIDYLAMINE CALCIUM CHANNEL BLOCKERS

[75] Inventors: Lain-Yen Hu, Ann Arbor; Thomas Charles Malone, Canton, both of Mich.; Laszlo Nadasdi, Oakland, Calif.; Michael Francis Rafferty; Todd Robert Ryder, both of Ann Arbor, Mich.; Diego F. Silva, Burlingame, Calif.; Yuntao Song, Ann Arbor, Mich.; Balazs G. Szoke, Palo Alto; Laszlo Urge, Berkeley, both of Calif.

[73] Assignee: Warner-Lambert Company, Morris Plains, N.J.

[21] Appl. No.: 09/230,229

[22] PCT Filed: May 28, 1998

[86] PCT No.: PCT/US98/10838

§ 371 Date: Jan. 19, 1999

§ 102(e) Date: Jan. 19, 1999

[87] PCT Pub. No.: WO98/54123

PCT Pub. Date: Dec. 3, 1998

Related U.S. Application Data

[60] Provisional application No. 60/048,252, May 30, 1997, and provisional application No. 60/052,191, Jul. 10, 1997.

[51] Int. Cl.[7] .......................... A61K 38/05; C07K 16/00
[52] U.S. Cl. .......................... 514/19; 530/334; 530/343
[58] Field of Search .............................. 514/19; 530/334, 530/343

[56] References Cited

PUBLICATIONS

Doroteo Chillemi et al.; "Synthesis of peptides of side chain A of insulin", Gazz chim, ital. 87, 1356–66(1957) also cited as CA52:14540f, Apr. 1957.
H.L.Slates et al.; "Degradation of alpha–methyl–3,4–dihydroxyphenylalanine", J.Org.Che. 29(6), 1424–9(1964);also cited as CA61:1933e, Jun. 1964.
DeSarro, G.B., et al., "Anticonvulsant Properties of Flunarizine on Reflex and Generalized Models of Epilepsy," *Neruopharmacology*, 1986, vol. 25, No. 7, pp 695–701.
DeSarro, G.B., et al., "Anticonvulsant effects of some calcium entry blockers in DBA/2 mice," *Br. J. Pharmacol.*, 1988, 93:247–256.
Valentino, K., et al., "A selective N–type calcium channel antagonist protects against neuronal loss after global cerebral ischemia," *Proc. Natl. Acad. Sci. USA*, Aug. 1993, vol. 90, pp. 7894–7897.
Chaplan, S.R., et al., "Role of Voltage–Dependent Calcium Channel Subtypes in Experimental Tactile Allodynia," *The Journal of Pharmacology and Experimental Therapeutics*, 1994, vol. 269, No. 3, 1117–1123.
Buchan, A.M., et al., "A Selective N–Type Ca2+–Channel Blocker Prevents CA1 Injury 24 h Following Severe Forebrain Ischemia and Reduces Infarction Following Focal Ischemia," *Journal of Cerebral Blood Flow and Metabolism*, 1994, 14:903–910.
Kwapiszewski, W. and Bialasiewicz, W., "Synthesis of α–Perhydroheterocyclicalkyl Acids," Acta Poloniae Pharmaceutica—Drug Research, 1994, vol. 51, No. 3, pp 227–229.

Malmberg, A.B. and Yaksh, T.L., "Voltage–Sensitive Calcium channels in Spinal Nociceptive Processing: Blockade of N– and P–type Channels Inhibits Formalin–induced Nociception," The Journal of Neuroscience, Aug. 1994, 14(B)L4882–4890.
IBID, "Effect of continuous intrathecal infusion of ω–conopeptides, N–type calcium–channel blockers, on behavior and antinociception in the formalin and hot–plate tests in rats," *Pain*, 1995, 60:83–90.
Takizawa, S., et al., "A Selective N–Type Calcium Channel Antagonist Reduces Extracellular Glutamate Release and Infarct Volume in Focal Cerebral Ischemia," *Journal of Cerebral Blood Flow and Metabolism*, 1995, 15:611–618.
Yenari, M.A., et al., "Time–course and treatment response with SNX–111, an N–type calcium channel blocker, in a rodent model of focal cerebral ischemia using diffusion––weighted MRI," *Brain Research*, 1996, 739:36–45.
Pringle, A.K., et al., "Selective N–Type Calcium Channel Antagonist Omega Conotoxin MVIIA Is Neuroprotective Against Hypoxic Neurodegeneration in Organotypic Hippocampal–Slice Cultures," *Stroke*, Nov. 1996, vol. 27, No. 11, 2124–2130.
Bowersox, S.S., et al., "Selective N–type Neuronal voltage–Sensitive Calcium Channel Blocker, SNX–111, Produces Spinal Antinociception in Rat Models of Acute, Persistent and Neuropathic Pain," *The Journal of Pharmacology and Experimental Therapeutics*, 1996, vol. 279, No. 3, 1243–1249.
Jackson, H.C. and Scheideler, M.A., "Behavioural and anticonvulsant effects of CA2+ channel toxins in DBA/2 mice," *Psychopharmacology*, 1996, 126:85–90.
Diaz, A. and Dickenson, A. H., "Blockade of spinal N– and P–type, but not L–type, calcium channels inhibits the excitability of rat dorsal horn neurones produced by subcutaneous formalin inflammation," *Pain*, 1997, 69:93–100.

*Primary Examiner*—Richard L. Raymond
*Assistant Examiner*—Sudhaker B. Patel
*Attorney, Agent, or Firm*—Charles W. Ashbrook

[57] ABSTRACT

The present invention provides compounds that block calcium channels having the Formula I shown below.

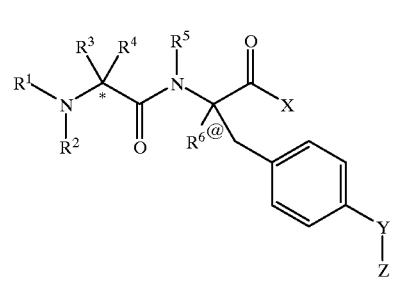

The present invention also provides methods of using the compounds of Formula I to treat stroke, cerebral ischemia, head trauma, or epilepsy and to pharmaceutical compositions that contain the compounds of Formula I.

29 Claims, No Drawings

SUBSTITUTED PEPTIDYLAMINE CALCIUM CHANNEL BLOCKERS

CROSS-REFERENCE TO RELATED APPLICATIONS

This application claims priority of PCT/US 98/10838, filed May 28, 1998, and U.S. Ser. No. 60/052,191, filed Jul. 10, 1997, and U.S. Ser. No. 60/048,252, filed May 30, 1997.

FIELD OF THE INVENTION

The present invention relates to compounds that act to block calcium channels; methods of using the compounds to treat stroke, cerebral ischemia, pain, head trauma or epilepsy; and to pharmaceutical compositions that contain the compounds of the present invention.

BACKGROUND OF THE INVENTION

The entry of excessive amounts of calcium ions into neurons following an ischemic episode or other neuronal trauma has been well documented. Uncontrolled high concentrations of calcium in neurons initiates a cascade of biochemical events that disrupts normal cellular processes. Among these events are the activation of proteases and lipases, breakdown of neuronal membranes and the formation of free radicals, which may ultimately lead to cell death. Several types of calcium channels have been discovered and called the L, N, P, Q, R, and T types. Each type possesses distinct structural features, functional properties and cellular/subcellular distributions. Type selective calcium channel blockers have been identified. For example, SNX-111 has been shown to be a selective N-type calcium channel blocker and has demonstrated activity in a number of models of ischemia and pain (Bowersox S. S., et al., *Drug News and Perspective*, 1994:7:261–268 and references cited therein). The compounds of the present invention are calcium channel blockers that can block N-type calcium channels and can be used to treat stroke, pain, cerebral ischemia, head trauma, and epilepsy.

SUMMARY OF THE INVENTION

The present invention provides compounds having the Formula I

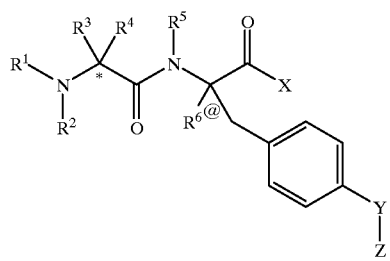

wherein
* denotes a first chiral center when $R^3$ and $R^4$ are different;
@ denotes a second chiral center;
$R^1$ and $R^2$ are independently hydrogen, $C_1$–$C_8$alkyl, $C_3$–$C_7$cycloalkyl,
  $C_3$–$C_8$substituted alkyl, $C_1$–$C_6$alkoxy, hydroxy, $C_3$–$C_6$heterocycloalkyl,
  $C_3$–$C_7$cycloalkenyl, $C_3$–$C_7$substituted, cycloalkenyl, $C_3$–$C_7$substituted cycloalkyl, —(CH$_2$)$_n$-aryl, (CH$_2$)$_n$-substituted aryl, $C_2$–$C_8$alkenyl,

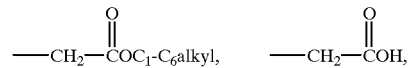

$C_2$–$C_8$substituted alkenyl, —CH$_2$—COC$_1$–C$_6$alkyl,
  —CH$_2$—COH,
—(CH$_2$)$_n$-heteroaryl, —(CH$_2$)$_n$-substituted heteroaryl,
—(CH$_2$)$_n$—C$_3$–C$_7$heterocycle, —(CH$_2$)$_n$-substituted C$_3$–C$_7$heterocycle,
—(CH$_2$)$_n$-cycloalkyl, —(CH$_2$)$_n$-substituted cycloalkyl, or $R^1$ and $R^2$ may be taken together to form a 5- to 7-membered ring which may contain heteroatoms, provided that $R^1$ and $R^2$ are not both hydrogen;

$R^3$, $R^5$, and $R^6$ are independently hydrogen or $C_1$–$C_8$alkyl;

$R^4$ is $C_1$–$C_8$alkyl,
  —(CH$_2$)$_n$C$_3$–C$_7$cycloalkyl,
  —(CH$_2$)$_n$C$_3$–C$_7$substituted cycloalkyl, or
  —(CH$_2$)$_n$phenyl;

Y is —(CH$_2$)$_n$—, —O(CH$_2$)$_n$—, —(CH$_2$)$_n$O—, —N(R$^3$)(CH$_2$)$_n$—, —(CH$_2$)$_n$N(R$^3$)—,
—S(CH$_2$)$_n$—, —(CH$_2$)$_n$S—, —C=C—, or —C≡C—;

Z is aryl, substituted aryl, heteroaryl, substituted heteroaryl, $C_3$–$C_7$cycloalkyl, substituted $C_3$–$C_7$cycloalkyl, or $C_1$–$C_8$alkyl;

X is heterocycle, substituted heterocycle,
  —NH(CH$_2$)$_n$NR$^3$R$^5$,
  —NH(CH$_2$)$_n$heteroaryl,
  —NH(CH$_2$)$_n$substituted heteroaryl,
  —NH(CH$_2$)$_n$NH(CH$_2$)$_n$phenyl,
  —NH(CH$_2$)$_n$NH(CH$_2$)$_n$—OH,
  —NH-heterocycle-CH$_2$phenyl,

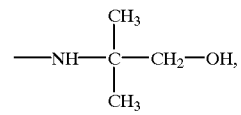

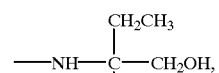

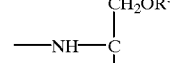

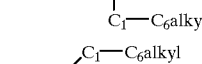

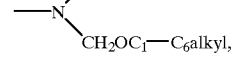

—NH(CH$_2$)$_n$-heterocycloalkyl,

—OC$_1$–C$_6$alkyl,

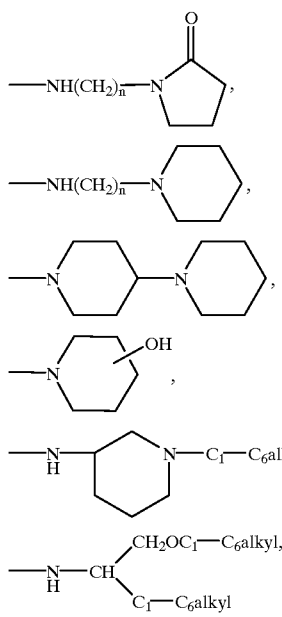

—NH(CH$_2$)$_n$heterocycle,
—NH(CH$_2$)$_n$substituted heterocycle;
—OR$^3$, —NHR$^3$, —NR$^3$R$^5$, wherein in addition to the definitions of R$^3$ and R$^5$ above, R$^3$ and R$^5$ can together with the nitrogen atom form a ring having from 3 to 7 atoms;
each n is 0 to 5, and the pharmaceutically acceptable salts, esters, amides and prodrugs thereof.

In a preferred embodiment of the compound of Formula I, R$^1$ is methyl.

In another preferred embodiment of the compounds of Formula I, R$^3$, R$^5$, and R$^6$ are hydrogen.

In another preferred embodiment of the compounds of Formula I,

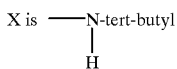

or —O-tert-butyl.

In another preferred embodiment of the compounds of Formula I,

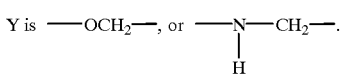

In another preferred embodiment of the compounds of Formula I, Z is phenyl.

In another preferred embodiment of the compounds of Formula I, R$^1$ is methyl, R$^3$, R$^5$, and R$^6$ are hydrogen, R$^4$ is isobutyl,

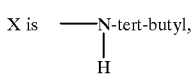

Y is —OCH$_2$—, and Z is phenyl.

In another preferred embodiment of the compounds of Formula I, R$^3$ is hydrogen and R$^2$ is C$_1$–C$_8$ alkyl, substituted cyclohexyl, cyclohexyl, cyclohexenyl, —CH$_2$-phenyl, —CH$_2$-substituted phenyl, —CH$_2$-cyclohexyl,

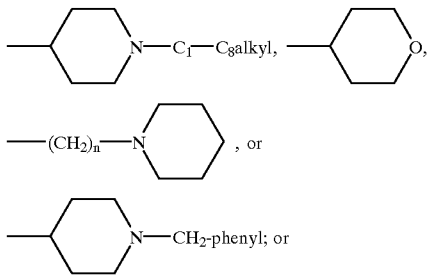

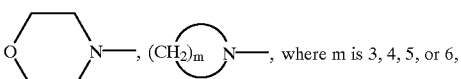

R$^2$ and R$^3$ taken together along with the nitrogen atom form a ring having the structure

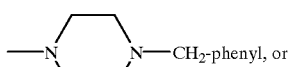

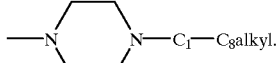

In another preferred embodiment of the compounds of Formula I, R$^3$ is isobutyl, and R$^4$ is hydrogen.

In another preferred embodiment of the compounds of Formula I, R$^5$ and R$^6$ are hydrogen.

In another preferred embodiment of the compounds of Formula I, R$^2$ is C$_1$–C$_8$alkyl, cyclohexyl, substituted cyclohexyl, —CH$_2$-phenyl, or —CH$_2$-substituted phenyl.

In another preferred embodiment of the compounds of Formula I,

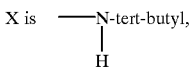

—O-tert-butyl,

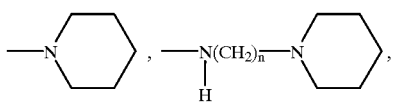

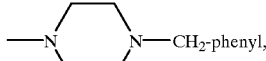

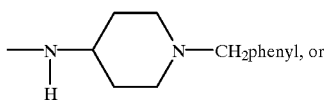

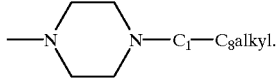

In another more preferred embodiment of the compounds of Formula I, $R^1$ is methyl; and $R^2$ is $C_1$–$C_8$alkyl, substituted cyclohexyl, cyclohexyl, cyclohexenyl, —$CH_2$-phenyl, —$CH_2$-substituted phenyl, —$CH_2$-cyclohexyl, $C_1$–$C_8$alkenyl, —$CH_2$-pyridyl,

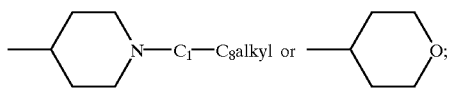

wherein m is 3, 4, 5, or 6;

$R^3$, $R^5$, and $R^6$ are hydrogen;

$R^4$ is isobutyl;

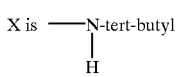

or —O-tert-butyl;

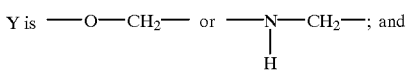

Z is phenyl.

In another more preferred embodiment of the compounds of Formula I,

Y is —O—$CH_2$— or

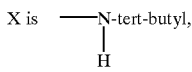

Z is phenyl;

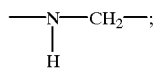

—O-tert-butyl

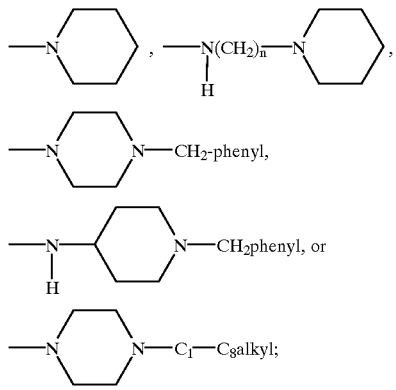

$R^4$ and $R^5$ are hydrogen;

$R^3$ is isobutyl;

$R^1$ is methyl; and $R^2$ is $C_1$–$C_8$alkyl, —$(CH_2)_n$substituted phenyl, or cyclohexyl.

In a most preferred embodiment of the present invention, the compounds are:

2-Dimethylamino-4-methyl-pentanoic acid [2-(4-benzyloxy-phenyl)-1-tert-butylcarbamoyl-ethyl]-amide;

2-Dimethylamino-4-methyl-pentanoic acid [2-(4-benzyloxy-phenyl)-1-(piperidine-1-carbonyl)-ethyl]-amide;

2-Dimethylamino-4-methyl-pentanoic acid [2-(4-benzyloxy-phenyl)-1-(2-piperidin-1-yl-ethylcarbamoyl)-ethyl]-amide;

2-Dimethylamino-4-methyl-pentanoic acid [1-(4-benzyloxy-benzyl)-2-(4-benzyl-piperazin-1-yl)-2-oxo-ethyl]-amide;

2-Dimethylamino-4-methyl-pentanoic acid [2-(4-benzyloxy-phenyl)-1-(1-benzyl-piperidin-4-yl-carbamoyl)-ethyl]-amide;

2-Dimethylamino-4-methyl-pentanoic acid [1-(4-benzyloxy-benzyl)-2-(4-methyl-piperazin-1-yl)-2-oxo-ethyl]-amide;

4-Methyl-2-[methyl-(3-methyl-butyl)-amino]-pentanoic acid [2-(4-benzyloxy-phenyl)-1-tert-butylcarbamoyl-ethyl]-amide;

4-Methyl-2-[methyl-(3-methyl-butyl)-amino]-pentanoic acid [1-(4-benzyloxy-benzyl)-2-oxo-2-piperidin-1-yl-ethyl]-amide;

4-Methyl-2-[methyl-(3-methyl-butyl)-amino]-pentanoic acid [2-(4-benzyloxy-phenyl)-1-(2-piperidin-1-yl-ethylcarbamoyl)-ethyl]-amide;

4-Methyl-2-[methyl-(3-methyl-butyl)-amino]-pentanoic acid [1-(4-benzyloxy-benzyl)-2-(4-benzyl-piperazin-1-yl)-2-oxo-ethyl]-amide;

4-Methyl-2-[methyl-(3-methyl-butyl)-amino]-pentanoic acid [2-(4-benzyloxy-phenyl)-1-(1-benzyl-piperidin-4-ylcarbamoyl)-ethyl]-amide;

4-Methyl-2-[methyl-(3-methyl-butyl)-amino]-pentanoic acid [1-(4-benzyloxy-benzyl)-2-(4-methyl-piperazin-1-yl)-2-oxo-ethyl]-amide;

2-[(4-tert-Butyl-benzyl)-methyl-amino]-4-methyl-pentanoic acid [2-(4-benzyloxy-phenyl)-1-tert-butylcarbamoyl-ethyl]-amide;

2-[(4-tert-Butyl-benzyl)-methyl-amino]-4-methyl-pentanoic acid [2-(4-benzyloxy-phenyl)-1-(piperidine-1-carbonyl)-ethyl]-amide;

2-[(4-tert-Butyl-benzyl)-methyl-amino]-4-methyl-pentanoic acid [2-(4-benzyloxy-phenyl)-1-(2-piperidin-1-yl-ethylcarbamoyl)-ethyl]-amide;

2-[(4-tert-Butyl-benzyl)-methyl-amino]-4-methyl-pentanoic acid [1-(4-benzyloxy-benzyl)-2-(4-benzyl-piperazin-1-yl)-2-oxo-ethyl]-amide;

2-[(4-tert-Butyl-benzyl)-methyl-amino]-4-methyl-pentanoic acid [2-(4-benzyloxy-phenyl)-1-(1-benzyl-piperidin-4-yl-carbamoyl)-ethyl]-amide;

2-[(4-tert-Butyl-benzyl)-methyl-amino]-4-methyl-pentanoic acid [1-(4-benzyloxy-benzyl)-2-(4-methyl-piperazin-1-yl)-2-oxo-ethyl]-amide;

2-(Cyclohexyl-methyl-amino)-4-methyl-pentanoic acid [2-(4-benzyloxy-phenyl)-1-tert-butylcarbamoyl-ethyl]-amide;

2-(Cyclohexyl-methyl-amino)-4-methyl-pentanoic acid [2-(4-benzyloxy-phenyl)-1-(piperidine-1-carbonyl)-ethyl]-amide;

2-(Cyclohexyl-methyl-amino)-4-methyl-pentanoic acid [2-(4-benzyloxy-phenyl)-1-(2-piperidin-1-yl-ethylcarbamoyl)-ethyl]-amide;

2-(Cyclohexyl-methyl-amino)-4-methyl-pentanoic acid [1-(4-benzyloxy-benzyl)-2-(4-benzyl-piperazin-1-yl)-2-oxo-ethyl]-amide;

2-(Cyclohexyl-methyl-amino)-4-methyl-pentanoic acid [2-(4-benzyloxy-phenyl)-1-(1-benzyl-piperidin-4-ylcarbamoyl)-ethyl]-amide;

2-(Cyclohexyl-methyl-amino)-4-methyl-pentanoic acid [1-(4-benzyloxy-benzyl)-2-(4-methyl-piperazin-1-yl)-2-oxo-ethyl]-amide;

2-(Cyclohexylmethyl-methyl-amino)-4-methyl-pentanoic acid [2-(4-benzyloxy-phenyl)-1-tert-butylcarbamoyl-ethyl]-amide;

2-(Cyclohexylmethyl-methyl-amino)-4-methyl-pentanoic acid [2-(4-benzyloxy-phenyl)-1-(piperidine-1-carbonyl)-ethyl]-amide;

2-(Cyclohexylmethyl-methyl-amino)4-methyl-pentanoic acid [2-(4-benzyloxy-phenyl)-1-(2-piperidin-1-yl-ethylcarbamoyl)-ethyl]-amide;

2-(Cyclohexylmethyl-methyl-amino)-4-methyl-pentanoic acid [1-(4-benzyloxy-benzyl)-2-(4-benzyl-piperazin-1-yl)-2-oxo-ethyl]-amide;

2-(Cyclohexylmethyl-methyl-amino)-4-methyl-pentanoic acid [2-(4-benzyloxy-phenyl)-1-(1-benzyl-piperidin4-ylcarbamoyl)-ethyl]-amide;

2-(Cyclohexylmethyl-methyl-amino)-4-methyl-pentanoic acid [1-(4-benzyloxy-benzyl)-2-(4-methyl-piperazin-1-yl)-2-oxo-ethyl]-amide;

3-(4-Benzyloxy-phenyl)-2-[4-methyl-2-(3-methyl-but-2-enylamino)-pentanoylamino]-propionic acid tert-butyl ester;

3-(4-Benzyloxy-phenyl)-2-[2-(4-tert-butyl-benzylamino)-4-methyl-pentanoylamino]-propionic acid tert-butyl ester;

2-(2-Benzylamino-4-methyl-pentanoylamino)-3-(4-benzyloxy-phenyl)-propionic acid tert-butyl ester;

4-Methyl-2-[methyl-(3-methyl-butyl)-amino]-pentanoic acid [2-(4-benzyloxy-phenyl)-1-tert-butylcarbamoyl-ethyl]-amide;

4-Methyl-2-methylamino-pentanoic acid [2-(4-benzyloxy-phenyl)-1-tert-butylcarbamoyl-ethyl]-amide;

2-[(3,3-Dimethyl-butyl)-methyl-amino]-4-methyl-pentanoic acid [2-(4-benzyloxy-phenyl)-1-tert-butylcarbamoyl-ethyl]-amide;

2-Diethylamino-4-methyl-pentanoic acid [2-(4-benzyloxy-phenyl)-1-tert-butylcarbamoyl-ethyl]-amide;

2-[(4-tert-Butyl-cyclohexyl)-methyl-amino]-4-methyl-pentanoic acid [2-(4-benzyloxy-phenyl)-1-tert-butylcarbamoyl-ethyl]-amide;

4-Methyl-2-[methyl-(4-methyl-cyclohexyl)-amino]-pentanoic acid [2-(4-benzyloxy-phenyl)-1-tert-butylcarbamoyl-ethyl]-amide;

2-[(4-Dimethylamino-benzyl)-methyl-amino]-4-methyl-pentanoic acid [2-(4-benzyloxy-phenyl)-1-tert-butylcarbamoyl-ethyl]-amide;

2-(Butyl-methyl-amino)-4-methyl-pentanoic acid [2-(4-benzyloxy-phenyl)-1-tert-butylcarbamoyl-ethyl]-amide;

2-(Isobutyl-methyl-amino)-4-methyl-pentanoic acid [2-(4-benzyloxy-phenyl)-1-tert-butylcarbamoyl-ethyl]-amide;

4-Methyl-2-methylamino-pentanoic acid [1-(4-benzyloxy-benzyl)-2-(4-benzyl-piperazin-1-yl)-2-oxo-ethyl]-amide;

3-Methyl-2-[methyl-(3-methyl-butyl)-amino]-pentanoic acid [2-(4-benzyloxy-phenyl)-1-tert-butylcarbamoyl-ethyl]-amide;

4-Methyl-2-[ethyl-(3-methyl-butyl)-amino]-pentanoic acid [2-(4-benzyloxy-phenyl)-1-tert-butylcarbamoyl-ethyl]-amide;

4-Methyl-2-[methyl-(3-methyl-butyl)-amino]-butyric acid [2-(4-benzyloxy-phenyl)-1-tert-butylcarbamoyl-ethyl]-amide;

2-(Cyclohex-2-enyl-methyl-amino)-4-methyl-pentanoic acid [2-(4-benzyloxy-phenyl)-1-tert-butylcarbamoyl-ethyl]-amide;

2-[(4-tert-Butyl-benzyl)-methyl-amino]-4-methyl-pentanoic acid [2-(4-benzyloxy-phenyl)-1-tert-butylcarbamoyl-ethyl]-amide;

2-(Cyclohex-2-enylamino)-4-methyl-pentanoic acid [2-(4-benzyloxy-phenyl)-1-tert-butylcarbamoyl-ethyl]-amide;

2-(4-tert-Butyl-benzylamino)-4-methyl-pentanoic acid [2-(4-benzyloxy-phenyl)-1-tert-butylcarbamoyl-ethyl]-amide;

4-Methyl-2-[methyl-(3-methyl-but-2-enyl)-amino]-pentanoic acid [2-(4-benzyloxy-phenyl)-1-tert-butylcarbamoyl-ethyl]-amide;

2-(4-tert-Butyl-benzylamino)-4-methyl-pentanoic acid [1-(4-benzyloxy-benzyl)-2-(4-benzyl-piperazin-1-yl)-2-oxo-ethyl]-amide;

4-Methyl-2-(3-methyl-but-2-enylamino)-pentanoic acid [1-(4-benzyloxy-benzyl)-2-(4-benzyl-piperazin-1-yl)-2-oxo-ethyl]-amide;

2-(Benzyl-methyl-amino)-4-methyl-pentanoic acid [2-(4-benzyloxy-phenyl)-1-tert-butylcarbamoyl-ethyl]-amide;

2-[(4-tert-Butyl-benzyl)-methyl-amino]-4-methyl-pentanoic acid [2-(4-benzylamino-phenyl)-1-tert-butylcarbamoyl-ethyl]-amide; and 2-(Cyclohexyl-methyl-amino)-4-methyl-pentanoic acid [2-(4-benzyloxy-phenyl)-1-tert-butylcarbamoyl-ethyl]-amide.

In another most preferred embodiment of the present invention, the compounds are:

2-[(4-Chloro-benzyl)-methyl-amino]-4-methyl-pentanoic acid [2-(4-benzyloxy-phenyl)-1-tert-butylcarbamoyl-ethyl]-amide;

2-[(2-Chloro-benzyl)-methyl-amino]-4-methyl-pentanoic acid [2-(4-benzyloxy-phenyl)-1-tert-butylcarbamoyl-ethyl]-amide;

2-[(3-Chloro-benzyl)-methyl-amino]-4-methyl-pentanoic acid [2-(4-benzyloxy-phenyl)-1-tert-butylcarbamoyl-ethyl]-amide;

2-[(4-Methoxybenzyl)-methyl-amino]-4-methyl-pentanoic acid [2-(4-benzyloxy-phenyl)-1-tert-butylcarbamoyl-ethyl]-amide;

2-[(4-Ethoxybenzyl)-methyl-amino]-4-methyl-pentanoic acid [2-(4-benzyloxy-phenyl)-1-tert-butylcarbamoyl-ethyl]-amide;

2-[(3-Methoxybenzyl)-methyl-amino]-4-methyl-pentanoic acid [2-(4-benzyloxy-phenyl)-1-tert-butylcarbamoyl-ethyl]-amide;

2-[(2-Methoxybenzyl)-methyl-amino]-4-methyl-pentanoic acid [2-(4-benzyloxy-phenyl)-1-tert-butylcarbamoyl-ethyl]-amide;

2-[(4-Pyridyl)-methyl-amino]-4-methyl-pentanoic acid [2-(4-benzyloxy-phenyl)-1-tert-butylcarbamoyl-ethyl]-amide;

2-(2-Hydroxycyclohexyl-methyl-amino)-4-methyl-pentanoic acid [2-(4-benzyloxy-phenyl)-1-tert-butylcarbamoyl-ethyl]-amide;

4-Methyl-2-[methyl-(N,N-dimethyl-3-amino-propyl)-amino]-pentanoic acid [2-(4-benzyloxy-phenyl)-1-tert-butylcarbamoyl-ethyl]-amide;

2-(Cyclohexyl-amino)-4-methyl-pentanoic acid [2-(4-benzyloxy-phenyl)-1-tert-butylcarbamoyl-ethyl]-amide;

2-[(Isoprop-2-yl)-amino]-4-methyl-pentanoic acid [2-(4-benzyloxy-phenyl)-1-tert-butylcarbamoyl-ethyl]-amide;

2-[(Isoprop-2-yl)-methyl-amino]-4-methyl-pentanoic acid [2-(4-benzyloxy-phenyl)-1-tert-butylcarbamoyl-ethyl]-amide;

2-[(N-methyl-piperidin-4-yl)-methyl-amino]-4-methyl-pentanoic acid [2-(4-benzyloxy-phenyl)-1-tert-butylcarbamoyl-ethyl]-amide;

2-[(N-methyl-piperidin-4-yl)-amino]-4-methyl-pentanoic acid [2-(4-benzyloxy-phenyl)-1-tert-butylcarbamoyl-ethyl]-amide;

2-[(Pyran-4-yl)-methyl-amino]-4-methyl-pentanoic acid [2-(4-benzyloxy-phenyl)-1-tert-butylcarbamoyl-ethyl]-amide;

2-[(Pyran-4-yl)-amino]-4-methyl-pentanoic acid [2-(4-benzyloxy-phenyl)-1-tert-butylcarbamoyl-ethyl]-amide;

2-Morpholine-4-methyl-pentanoic acid [2-(4-benzyloxy-phenyl)-1-tert-butylcarbarnoyl-ethyl]-amide;

2-Pyrrolidine-4-methyl-pentanoic acid [2-(4-benzyloxy-phenyl)-1-tert-butylcarbamoyl-ethyl]-amide;

2-Piperidine-4-methyl-pentanoic acid [2-(4-benzyloxy-phenyl)-1-tert-butylcarbamoyl-ethyl]-amide;

2-Hexamethyleneimine-4-methyl-pentanoic acid [2-(4-benzyloxy-phenyl)-1-tert-butylcarbamoyl-ethyl)]-amide;

2-[(4-Fluoro-benzyl)-methyl-amino]-4-methyl-pentanoic acid [2-(4-benzyloxy-phenyl)-1-(piperidine-1-carbamoyl-ethyl)]-amide;

2-[(4-Chloro-benzyl)-methyl-amino]-4-methyl-pentanoic acid [2-(4-benzyloxy-phenyl)-1-(piperidine-1-carbamoyl-ethyl)]-amide;

2-[(4-Bromo-benzyl)-methyl-amino]-4-methyl-pentanoic acid [2-(4-benzyloxy-phenyl)-1-(piperidine-1-carbamoyl-ethyl)]-amide;

2-[(2-Chloro-benzyl)-methyl-amino]-4-methyl-pentanoic acid [2-(4-benzyloxy-phenyl)-1-(piperidine-1-carbamoyl-ethyl)]-amide;

2-[(3-Chloro-benzyl)-methyl-amino-4-methyl-pentanoic acid [2-(4-benzyloxy-phenyl)-1-(piperidine-1-carbamoyl-ethyl)]-amide;

2-[(4-Hydroxybenzyl)-methyl-amino]-4-methyl-pentanoic acid [2-(4-benzyloxy-phenyl)-1-(piperidine-1-carbamoyl-ethyl)]-amide;

2-[(4-Methoxybenzyl)-methyl-amino]-4-methyl-pentanoic acid [2-(4-benzyloxy-phenyl)-1-(piperidine-1-carbamoyl-ethyl)]-amide;

2-[(4-Ethoxybenzyl)-methyl-amino]-4-methyl-pentanoic acid [2-(4-benzyloxy-phenyl)-1-tert-(piperidine-1-carbamoyl-ethyl)]-amide;

2-[(3-Methoxybenzyl)-methyl-amino]-4-methyl-pentanoic acid [2-(4-benzyloxy-phenyl)-1-(piperidine-1-carbamoyl-ethyl)]-amide;

2-[(2-Methoxybenzyl)-methyl-amino]-4-methyl-pentanoic acid [2-(4-benzyloxy-phenyl)-1-(piperidine-1-carbamoyl-ethyl)]-amide;

2-[(4-Pyridyl)-methyl-amino]-4-methyl-pentanoic acid [2-(4-benzyloxy-phenyl)-1-(piperidine-1-carbamoyl-ethyl)]-amide;

2-[(2-Hydroxycyclohexyl-methyl-amino]-4-methyl-pentanoic acid [2-(4-benzyloxy-phenyl)-1-(piperidine-1-carbamoyl-ethyl)]-amide;

4-Methyl-2-[methyl-(N,N-dimethyl-3-amino-propyl)-amino]-pentanoic acid [2-(4-benzyloxy-phenyl)-1-(piperidine-1-carbamoyl-ethyl)]-amide;

2-(Cyclohexyl-amino)-4-methyl-pentanoic acid [2-(4-benzyloxy-phenyl)-1-(piperidine-1-carbamoyl-ethyl)]-amide;

2-(Isoprop-2-yl)-amino]-4-methyl-pentanoic acid [2-(4-benzyloxy-phenyl)-1-(piperidine-1carbamoyl-ethyl)]-amide;

2-(Isoprop-2-yl)-methyl-amino)-4-methyl-pentanoic acid [2-(4-benzyloxy-phenyl)-1-(piperidine-1-carbamoyl-ethyl)]-amide;

2-[N-methyl-piperidin-4-yl)-methyl-amino]-4-methyl-pentanoic acid [2-(4-benzyloxy-phenyl)-1-(piperidine-1-carbamoyl-ethyl)]-amide;

2-[(N-methyl-piperidin-4-yl)-methyl-amino]-4-methyl-pentanoic acid [2-(4-benzyloxy-phenyl)-1-(piperidine-1-carbamoyl-ethyl)]-amide;

2-[(Pyran-4-yl)-methyl-amino]-4-methyl-pentanoic acid [2-(4-benzyloxy-phenyl)-1-(piperidine-1-carbamoyl-ethyl)]-amide;

2-[(Pyran-4-yl)-amino]-4-methyl-pentanoic acid [2-(4-benzyloxy-phenyl)-1-(piperidine-1-carbamoyl-ethyl)]-amide;

2-Pyrrolidine-4-methyl-pentanoic acid [2-(4-benzyloxy-phenyl)-1-(piperidine-1-carbamoyl-ethyl)]-amide;

2-Morpholine-4-methyl-pentanoic acid [2-(4-benzyloxy-phenyl)-1-(piperidine-1-carbamoyl-ethyl)]-amide;

2-Piperidine-4-methyl-pentanoic acid [2-(4-benzyloxy-phenyl-1-(piperidine-1-carbamoyl-ethyl)]-amide;

2-Hexamethyleneimine-4-methyl-pentanoic acid [2-(4-benzyloxy-phenyl)-1-(piperidine-1-carbamoyl-ethyl)]-amide;

2-[(4-Fluoro-benzyl)-methyl-amino]-4-methyl-pentanoic acid [1-(4-benzyloxy-phenyl)-2-(4-methyl-piperazine-1-yl)-2-oxo-ethyl]-amide;

2-[(4-Chloro-benzyl)-methyl-amino]-4-methyl-pentanoic acid [2-(4-benzyloxy-phenyl)-2-(4-methyl-piperazine-1-yl)-2-oxo-ethyl]-amide;

2-[(4-Bromo-benzyl)-methyl-amino]-4-methyl-pentanoic acid [2-(4-benzyloxy-phenyl)-2-(4-methyl-piperazine-1-yl)-2-oxo-ethyl]-amide;

2-[(2-Chloro-benzyl)-methyl-amino]-4-methyl-pentanoic acid [2-(4-benzyloxy-phenyl)-2-(4-methyl-piperazine-1-yl)-2-oxo-ethyl]-amide;

2-[(3-Chloro-benzyl)-methyl-amino]-4-methyl-pentanoic acid [2-(4-benzyloxy-phenyl)-2-(4-methyl-piperazine-1-yl)-2-oxo-ethyl]-amide;

2-[(4-Hydroxybenzyl)-methyl-amino]-4-methyl-pentanoic acid [2-(4-benzyloxy-phenyl)-2-(4-methyl-piperazine-1-yl)-2-oxo-ethyl]-amide;

2-[(4-Methoxybenzyl)-methyl-amino]-4-methyl-pentanoic acid [2-(4-benzyloxy-phenyl)-2-(4-methyl-piperazine-1-yl)-2-oxo-ethyl]-amide;

2-[(4-Ethoxybenzyl)-methyl-amino]-4-methyl-pentanoic acid [2-(4-benzyloxy-phenyl)-2-(4-methyl-piperazine-1-yl)-2-oxo-ethyl]-amide;

2-[(3-Methoxybenzyl)-methyl-amino]-4-methyl-pentanoic acid [2-(4-benzyloxy-phenyl)-2-(4-methyl-piperazine-1-yl)-2-oxo-ethyl]-amide;

2-[(2-Metboxybenzyl)-methyl-amino]-4-methyl-pentanoic acid [2-(4-benzyloxy-phenyl)-2-(4-methyl-piperazine-1-yl)-2-oxo-ethyl]-amide;

2-[(4-Pyridyl)-methyl-amino]-4-methyl-pentanoic acid [2-(4-benzyloxy-phenyl)-2-(4-methyl-piperazine-1-yl)-2-oxo-ethyl]-amide;

2-(2-Hydroxycyclohexyl-methyl-amino)-4-methyl-pentanoic acid [2-(4-benzyloxy-phenyl)-2-(4-methyl-piperazine-1-yl)-2-oxo-ethyl]-amide;

4-Methyl-2-[methyl-(N,N-dimethyl-3-amino-propyl)-amino]-pentanoic acid [2-(4-benzyloxy-phenyl)-2-(4-methyl-piperazine-1-yl)-2-oxo-ethyl]-amide;

2-(Cyclohexyl-amino)-4-methyl-pentanoic acid [2-(4-benzyloxy-phenyl)-2-(4-methyl-piperazin-1-yl]-2-oxo-ethyl-amide;

2-[(Isoprop-2-yl)-amino]-4-methyl-pentanoic acid [2-(4-benzyloxy-phenyl)-2-(4-methyl-piperazin-1-yl)-2-oxo-ethyl]-amide;

2-[(Isoprop-2-yl)-methyl-amino]-4-methyl-pentanoic acid [2-(4-benzyloxy-phenyl)-2-(4-methyl-piperazin-1-yl)-2-oxo-ethyl]-amide;

2-Pyrrolidine-4-methyl-pentanoic acid [2-(4-benzyloxy-phenyl)-2-(4-methyl-piperazin-1-yl)-2-oxo-ethyl]-amide;

2-Morpholine-4-methyl-pentanoic acid [2-(4-benzyloxy-phenyl-1-tert-butylcarbamoyl-ethyl]-amide;

2-Piperidine-4-methyl-pentanoic acid [2-(4-benzyloxy-phenyl)-2-(4-methyl-piperazin-1-yl)-2-oxo-ethyl]-amide;

2-Hexamethyleneimine-4-methyl-pentanoic acid [2-(4-benzyloxy-phenyl)-2-(4-methyl-piperazin-1-yl)-2-oxo-ethyl]-amide;

[S-(R*,R*)]-4-Methyl-2-morpholin-4-yl-pentanoic acid [2-(4-benzyloxy-phenyl)-1-(2-morpholin-4-yl-ethylcarbamoyl)-ethyl]-amide;

[S-(R*,R*)]-4-Methyl-2-morpholin-4-yl-pentanoic acid [2-(4-benzyloxy-phenyl)-1-(2-pyridin-2-yl-ethylcarbamoyl)-ethyl]-amide;

[S-(R*,R*)]-4-Methyl-2-morpholin-4-yl-pentanoic acid [2-(4-benzyloxy-phenyl)-1-(3-imidazol-1-yl-propylcarbamoyl)-ethyl]-amide;

[S-(R*,R*)]-4-Methyl-2-morpholin-4-yl-pentanoic acid [2-(4-benzyloxy-phenyl)-1-(2-thiomorpholin-4-yl-ethylcarbamoyl)-ethyl]-amide;

[S-(R*,R*)]-4-Methyl-2-morpholin4-yl-pentanoic acid [2-(4-benzyloxy-phenyl)-1-(2-hydroxy-1,1 -dimethyl-ethylcarbamoyl)-ethyl]-amide;

[S-(R*,R*)]-4-Methyl-2-morpholin-4-yl-pentanoic acid [2-(4-benzyloxy-phenyl)-1-(1,1 -bis-hydroxymethyl-propyl-carbamoyl)-ethyl]-amide;

[S-(R*,R*)]-4-Methyl-2-morpholin4-yl-pentanoic acid [2-(4-benzyloxy-phenyl)-1-(2-pyrrolidin-1-yl-ethylcarbamoyl)-ethyl]-amide;

[S-(R*,R*)]-4-Methyl-2-morpholin-4-yl-pentanoic acid [2-(4-benzyloxy-phenyl)-1-(4-hydroxypiperidinylcarbamoyl)-ethyl]-amide;

[S-(R*,R*)]-4-Methyl-2-(tetrahydropyran-4-yl-amino)-pentanoic acid [2-(4-benzyloxy-phenyl)-1-(2-morpholin-4-yl-ethylcarbamoyl)-ethyl]-amide;

[S-(R*,R*)]-4-Methyl-2-(tetrahydropyran-4-y-amino)-pentanoic acid [2-(4-benzyloxy-phenyl)-1-(-(2-pyridin-2-yl-ethylcarbamoyl)-ethyl]-amide;

[S-(R*,R*)]-4-Methyl-2-(tetrahydropyran-4-yl-amino)-pentanoic acid [2-(4-benzyloxy-phenyl)-1-(3-imidazol-1-yl-propylcarbamoyl)-ethyl]-amide;

[S-(R*,R*)]-4-Methyl-2-(tetrahydropyran-4-yl-amino)-pentanoic acid [2-(4-benzyloxy-phenyl)-1-(2-pyrrolidine-1-yl-ethylcarbamoyl]-amide;

[S-(R*,R*)]-4-Methyl-2-(tetrahydropyran-4-yl-amino)-pentanoic acid [2-(4-benzyloxy-phenyl)-1-(4-hydroxy-piperinylcarbamoyl]-amide;

[S-(R*,R*)]-2-Dimethylamino-4-methyl-pentanoic acid [2-(4-benzyloxy-phenyl)-1-(2-morpholin4-yl-ethylcarbamoyl)-ethyl]-amide;

[S-(R*,R*)]-2-Dimethylamino-4-methyl-pentanoic acid [2-(4-benzyloxy-phenyl)-1-(2-(2-aminoethyl)pyridine carbamoyl)-ethyl]-amide;

[S-(R*,R*)]-2-Dimethylamino-4-methyl-pentanoic acid [2-(4-benzyloxy-phenyl)-1-(3-imidazol-1-yl-propylcarbamoyl)-ethyl]-amide;

[S-(R*,R*)]-2-Dimethylamino-4-methyl-pentanoic acid [2-(4-benzyloxy-phenyl)-1-(thiomorpholinecarbamoyl)-ethyl]-amide;

[S-(R*,R*)]-2-Dimethylamino-4-methyl-pentanoic acid [2-(4-benzyloxy-phenyl)-1-(2-aminopropan-1-ol carbamoyl)-ethyl]-amide;

[S-(R*,R*)]-2-Dimethylamino-4-methyl-pentanoic acid [2-(4-benzyloxy-phenyl)-1-(2-hydroxymethylbutan-1-ol)-ethyl]-amide;

[S-(R*,R*)]-2-Dimethylamino-4-methyl-pentanoic acid [2-(4-benzyloxy-phenyl)-1-(1-methoxymethyl-propylcarbamoyl)-ethyl]-amide;

[S-(R*,R*)]-2-Dimethylamino-4-methyl-pentanoic acid [2-(4-benzyloxy-phenyl)-1-(2-pyrrolidin-1-yl-ethylcarbamoyl)-ethyl]-amide; and

[S-(R*,R*)]-2-Dimethylamino-4-methyl-pentanoic acid {2-(4-benzyloxy-phenyl)-1-[2-(2-hydroxy-ethylamino)-ethylcarbamoyl]-ethyl }-amide;

[S-(R*,R*)]-4-Methyl-2-[methyl-(3-methylbutyl)-amino]-pentanoic acid [2-(4-benzyloxy-phenyl)-1-(2-hydroxy-1,1-dimethyl-ethylcarbamoyl)-ethyl]-amide;

[S-(R*,R*)]-4-Methyl-2-[methyl-(3-methylbutyl)-amino]-pentanoic acid [2-(4-benzyloxy-phenyl)-1-(2-piperidin-1-yl-ethylcarbamoyl)-ethyl]-amide;

[S-(R*,R*)]-4-Methyl-2-[methyl-(3-methyl-butyl)-amino]-pentanoic acid {2-(4-benzyloxy-phenyl)-1-[3-(2-oxo-pyrrolidin- 1 -yl)-propylcarbamoyl]-ethyl}-amide;

[S-(R*,R*)]-4-Methyl-2-morpholin-4-yl-pentanoic acid [2-(4-benzyloxy-phenyl)-1-(2-morpholin-4-yl-ethylcarbamoyl)-ethyl]-amide;

[S-(R*,R*)]-4-Methyl-2-morpholin-4-yl-pentanoic acid [2-(4-benzyloxy-phenyl)-1-(2-pyridin-2-yl-ethylcarbamoyl)-ethyl]-amide;

[S-(R*,R*)]4-Methyl-2-morpholin-4-yl-pentanoic acid [2-(4-benzyloxy-phenyl)-1-(3-imidazol-1-yl-propylcarbamoyl)-ethyl]-amide;

[S-(R*,R*)]-4-Methyl-2-morpholin-4-yl-pentanoic acid [2-(4-benzyloxy-phenyl)-1-(2-thiomorpholin4-yl-ethylcarbamoyl)-ethyl]-amide;

[S-(R*,R*)]-4-Methyl-2-morpholin-4-yl-pentanoic acid [2-(4-benzyloxy-phenyl)-1-(2-hydroxy-1,1-dimethyl-ethylcarbamoyl)-ethyl]-amide;

[S-(R*,R*)]-4-Methyl-2-morpholin-4-yl-pentanoic acid [2-(4-benzyloxy-phenyl)-1-(1,1-bis-hydroxymethyl-propyl-carbamoyl)-ethyl]-amide;

[S-(R*,R*)]-4-Methyl-2-morpholin-4-yl-pentanoic acid [2-(4-benzyloxy-phenyl)-1-(2-pyrrolidin-1-yl-ethylcarbamoyl)-ethyl]-amide;

[S-(R*,R*)]-4-Methyl-2-morpholin-4-yl-pentanoic acid [2-(4-benzyloxy-phenyl)-1-(4-hydroxypiperidinylcarbamoyl)-ethyl]-amide;

[S-(R*,R*)]-4-Methyl-2-(tetrahydropyran-4-yl-amino)-pentanoic acid [2-(4-benzyloxy-phenyl)-1-(2-morpholin-4-yl-ethylcarbamoyl)-ethyl]-amide;

[S-(R*,R*)]-4-Methyl-2-(tetrahydropyran-4-yl-amino)-pentanoic acid [2-(4-benzyloxy-phenyl)-1-(-(2-pyridin-2-yl-ethylcarbamoyl)-ethyl]-amide;

[S-(R*,R*)]-4-Methyl-2-(tetrahydropyran-4-yl-amino)-pentanoic acid [2-(4-benzyloxy-phenyl)-1-(3-imidazol-1-yl-propylcarbamoyl)-ethyl]-amide;

[S-(R*,R*)]-4-Methyl-2-(tetrahydropyran-4-yl-amino)-pentanoic acid [2-(4-benzyloxy-phenyl)-1-(2-pyrrolidine-1-yl-ethylcarbamoyl)-ethyl]-amide;

[S-(R*,R*)]-4-Methyl-2-(tetrahydropyran-4-yl-amino)-pentanoic acid [2-(4-benzyloxy-phenyl)-1-(4-hydroxy-piperinylcarbamoyl]-amide;

[S-(R*,R*)]-2-Dimethylamino-4-methyl-pentanoic acid [2-(4-benzyloxy-phenyl)-1-(2-morpholin-4-yl-ethylcarbamoyl)-ethyl]-amide;

[S-(R*,R*)]-2-Dimethylamino-4-methyl-pentanoic acid [2-(4-benzyloxy-phenyl)-1-(2-(2-aminoethyl)pyridine carbamoyl)-ethyl]-amide;

[S-(R*,R*)]-2-Dimethylamino-4-methyl-pentanoic acid [2-(4-benzyloxy-phenyl)-1-(3-imidazol-1-yl-propylcarbamoyl)-ethyl]-amide;

[S-(R*,R*)]-2-Dimethylamino-4-methyl-pentanoic acid [2-(4-benzyloxy-phenyl)-1-(thiomorpholinecarbamoyl)-ethyl]-amide;

[S-(R*,R*)]-2-Dimethylamino-4-methyl-pentanoic acid [2-(4-benzyloxy-phenyl)-1-(2-aminopropan-1-ol carbamoyl)-ethyl]-amide;

[S-(R*,R*)]-2-Dimethylamino-4-methyl-pentanoic acid [2-(4-benzyloxy-phenyl)-1-(2-hydroxymethylbutan-1-ol)-ethyl]-amide;

[S-(R*,R*)]-2-Dimethylamino-4-methyl-pentanoic acid [2-(4-benzyloxy-phenyl)-1-(1-methoxymethyl-propylcarbamoyl)-ethyl]-amide;

[S-(R*,R*)]-2-Dimethylamino-4-methyl-pentanoic acid [2-(4-benzyloxy-phenyl)-1-(2-pyrrolidin-1-yl-ethylcarbamoyl)-ethyl]-amide; and

[S-(R*,R*)]-2-Dimethylamino-4-methyl-pentanoic acid {2-(4-benzyloxy-phenyl)-1-[2-(2-hydroxy-ethylamino)-ethylcarbamoyl]-ethyl}-amide.

Also provided is a pharmaceutical composition comprising a compound of Formula I.

Also provided is a method of blocking calcium channels, the method comprising administering to a patient in need of calcium channel blocking, a therapeutically effective amount of a compound of Formula I to block calcium channels.

In a preferred embodiment of the method, the calcium channels are N-type calcium channels.

In another embodiment, the present invention provides a method of blocking N-type calcium channels, the method comprising administering to a patient in need of N-type calcium channel blocking a therapeutically effective amount of a compound of Formula I effective to block N-type calcium channels.

The invention also provides a method of treating stroke, the method comprising administering to a patient having a stroke a therapeutically effective amount of a compound of Formula I.

The invention also provides a method of preventing a stroke, the method comprising administering to a patient at risk of having a stroke a therapeutically effective amount of a compound of Formula I.

The invention also provides a method of treating cerebral ischemia, the method comprising administering to a patient having cerebral ischemia a therapeutically effective amount of a compound of Formula I.

The invention also provides a method of treating head trauma, the method comprising administering to a patient having head trauma a therapeutically effective amount of a compound of Formula I.

Also provided is a method of treating epilepsy, the method comprising administering to a patient having epilepsy a therapeutically effective amount of a compound of Formula I.

Also provided is a method of treating pain, the method comprising administering to a patient having pain a therapeutically effective amount of a compound Formula I.

Also provided are the compounds:

[S-(R*,R*)]-4-Methyl-2-[methyl-(3-methyl-butyl)-amino]-pentanoic acid [2-(4-benzyloxy-phenyl)-1-(2-morpholin-4-yl-ethylcarbamoyl)-ethyl]-amide;

[S-(R*,R*)]-4-Methyl-2-[methyl-(3-methyl-butyl)-amino]-pentanoic acid [2-(4-benzyloxy-phenyl)-1-(2-pyridin-2-yl-ethylcarbamoyl)-ethyl]-amide;

[S-(R*,R*)]-4-Methyl-2-[methyl-(3-methyl-butyl)-amino]-pentanoic acid [2-(4-benzyloxy-phenyl)-1-(3-imidazol-1-yl-propylcarbamoyl)-ethyl]-amide;

[S-(R*,R*)]-4-Methyl-2-[methyl-(3-methyl-butyl)-amino]-pentanoic acid [1-(2-benzylamino-ethylcarbamoyl)-2-(4-benzyloxy-phenyl)-ethyl]-amide;

[S-(R*,R*)]-4-Methyl-2-[methyl-(3-methyl-butyl)-amino]-pentanoic acid [1-(4-benzyloxy-benzyl)-2-oxo-2-thiomorpholin-4-yl-ethyl]-amide;

[S-(R*,R*)]-4-Methyl-2-[methyl-(3-methyl-butyl)-amino]-pentanoic acid [2-(4-benzyloxy-phenyl)-1-(2-hydroxy-1-hydroxymethyl-1-methyl-ethylcarbamoyl)-ethyl]-amide;

[S-(R*,R*)]-4-Methyl-2-[methyl-(3-methyl-butyl)-amino]-pentanoic acid [2-(4-benzyloxy-phenyl)-1-(1-methoxymethyl-propylcarbamoyl)-ethyl]-amide;

[S-(R*,R*)]-4-Methyl-2-[methyl-(3-methyl-butyl)-amino]-pentanoic acid [2-(4-benzyloxy-phenyl)-1-(2-pyrrolidin-1-yl-ethylcarbamoyl)-ethyl]-amide;

[S-(R*,R*)]-4-Methyl-2-[methyl-(3-methyl-butyl)-amino]-pentanoic acid [1-(4-benzyloxy-benzyl)-2-(4-hydroxy-piperidin-1-yl)-2-oxo-ethyl]-amide;

[S-(R*,R*)]-4-Methyl-2-[methyl-(3-methyl-butyl)-amino]-pentanoic acid {2-(4-benzyloxy-phenyl)-1-[2-(2-hydroxy-ethylamino)-ethylcarbamoyl]-ethyl}-amide;

[S-(R*,R*)]-4-Methyl-2-[methyl-(3-methyl-butyl)-amino]-pentanoic acid [2-(4-benzyloxy-phenyl)-1-(1,1-benzyl-pyrrolidin-3-ylcarbamoyl)-ethyl]-amide;

[S-(R*,R*)]-4-Methyl-2-morpholin-4-yl-pentanoic acid [1-(2-benzylamino-ethylcarbamoyl)-2-(4-benzyloxy-phenyl)-ethyl]-amide;

[S-(R*,R*)]-4-Methyl-2-morpholin4-yl-pentanoic acid [2-(4-benzyloxy-phenyl)-1-(1-benzyl-pyrrolidin-3-ylcarbamoyl)-ethyl]-amide;

[S-(R*,R*)]-4-Methyl-2-morpholin4-yl-pentanoic acid [1-(4-benzyloxy-benzyl)-2-oxo-2-piperidin-1-yl-ethyl]-amide;

[S-(R*,R*)]-4-Methyl-2-(tetrahydro-pyran-4-ylamino)-pentanoic acid [1-(2-benzylamino-ethylcarbamoyl)-2-(4-benzyloxy-phenyl)-ethyl]-amide;

[S-(R*,R*)]-4-Methyl-2-(tetrahydro-pyran-4-ylamino)-pentanoic acid [1-(4-benzyloxy-benzyl)-2-oxo-2-thiomorpholin-4-yl-ethyl]-amide;

[S-(R*,R*)]-4-Methyl-2-(tetrahydro-pyran4-ylamino)-pentanoic acid [2-(4-benzyloxy-phenyl)-1-(2-hydroxy-1,1-dimethyl-ethylcarbamoyl)-ethyl]-amide;

[S-(R*,R*)]4-Methyl-2-(tetrahydro-pyran-4-ylamino)-pentanoic acid [2-(4-benzyloxy-phenyl)-1-(1,1-bis-hydroxymethyl-propylcarbamoyl)-ethyl]-amide;

[S-(R*,R*)]-4-Methyl-2-(tetrahydro-pyran-4-ylamino)-pentanoic acid [2-(4-benzyloxy-phenyl)-1-(1-methoxymethyl-propylcarbamoyl)-ethyl]-amide;

[S-(R*,R*)]-4-Methyl-2-(tetrahydro-pyran-4-ylamino)-pentanoic acid [2-(4-benzyloxy-phenyl)-1-(1-benzyl-pyrrolidin-3-ylcarbamoyl)-ethyl]-amide;

[S-(R*,R*)]-4-Methyl-2-(tetrahydro-pyran-4-ylamino)-pentanoic acid [2-(4-benzyloxy-phenyl)-1-(2-piperidin-1-yl-ethylcarbamoyl)-ethyl]-amide;

[S-(R*,R*)]4-Methyl-2-(tetrahydro-pyran-4-ylamino)-pentanoic acid [2-(4-benzyloxy-phenyl)-1-tert-butylcarbamoyl-ethyl]-amide;

[S-(R*,R*)]-4-Methyl-2-(tetrahydro-pyran-4-ylamino)-pentanoic acid [2-(4-benzyloxy-benzyl)-2-oxo-2-piperidin-1-yl-ethyl]-amide;

[S-(R*,R*)]-2-[(4-Fluoro-benzyl)-methyl-amino]-4-methyl-pentanoic acid [2-(4-benzyloxy-phenyl)-1-tert-butylcarbamoyl-ethyl]-amide;

[S-(R*,R*)]-2-[(4-Bromo-benzyl)-methyl-amino-]4-methyl-pentanoic acid [2-(4-benzyloxy-phenyl)-1-tert-butylcarbamoyl-ethyl]-amide;

[S-(R*,R*)]-2-[(4-Hydroxy-benzyl)-methyl-amino]-4-methyl-pentanoic acid [2-(4-benzyloxy-phenyl)-1-tert-butylcarbamoyl-ethyl]-amide;

[S-(R*,R*)]-4-Methyl-2-(methyl-pyridin-4-ylmethyl-amino)-pentanoic acid [2-(4-bezyloxy-phenyl)-1-tert-butylcarbamoyl-ethyl]-amide;

[S-(R*,S*)]-4-Methyl-2-[methyl-(3-methyl-butyl)-amino]-pentanoic acid [2-(4-benzyloxy-phenyl)-1-tert-butylcarbamoyl-ethyl]-amide;

[S-(R*,R*)]-3-(4-Benzyloxy-phenyl)-2-[4-methyl-2-(tetrahydro-pyran-4-ylamino)-pentanoylamino]-propionic acid tert-butyl ester;

[S-(R*,R*)]-2-(Isopropyl-methyl-amino)-4-methyl-pentanoic acid [2-(4-benzyloxy-phenyl)-1-tert-butylcarbamoyl-ethyl]-amide;

[S-(R*,R*)]-4-Methyl-2-[methyl-(tetrahydro-pyran-4-yl)-amino]-pentanoic acid [2-(4-benzyloxy-phenyl)-1-tert-butylcarbamoyl-ethyl]-amide;

[S-[R*,R*,(RS)]]-2-[(2-Hydroxy-1-methyl-ethyl)-methyl-amino]-4-methyl-pentanoic acid [2-(4-benzyloxy-phenyl)-1-tert-butylcarbamoyl-ethyl]-amide;

[S-(R*,R*)]-4-Methyl-2-[methyl-(1H-pyrrol-2-ylmethyl)-amino]-pentanoic acid [2-(4-benzyloxy-phenyl)-1-tert-butylcarbamoyl-ethyl]-amide;

[S-(R*,R*)]-2-(Furan-2-ylmethyl-methyl-amino)-4-methyl-pentanoic acid [2-(4-benzyloxy-phenyl)-1-tert-butylcarbamoyl-ethyl]-amide;

[S-(R*,R*)]-[S-(R*,R*)]-3-(4-Benzyloxy-phenyl)-2-[2-(cyclohexylmethyl-amino)-4-methyl-pentanoylamino]-propionic acid tert-butyl ester;

[S-(R*,R*)]-3-(4-Benzyloxy-phenyl)-2-(2-isopropylamino-4-methyl-pentanoylamino)-propionic acid tert-butyl ester;

[S-(R*,R*)]-3-(4-Benzyloxy-phenyl)-2-(2-cyclohexylamino-4-methyl-pentanoylamino)-propionic acid tert-butyl ester;

[S-(R*,R*)]-4-Methyl-2-morpholin-4-yl-pentanoic acid [2-(4-benzyloxy-phenyl)-1-tert-butylcarbamoyl-ethyl]-amide;

[S-(R*,R*)]-3-(4-Benzyloxy-phenyl)-2-[4-methyl-2-(3-methyl-butylamino)-pentanoylamino]-propionic acid tert-butyl ester;

[S-(R*,R*)]-({1-[2-(4-Benzyloxy-phenyl)-1-tert-butylcarbamoyl-ethylcarbamoyl]-3-methyl-butyl}-methyl-amino)-acetic acid ethyl ester;

[S-(R*,R*)]-2-[(3 -Hydroxy-butyl)-methyl-amino]-4-methyl-pentanoic acid [2-(4-benzyloxy-phenyl)-1-tert-butylcarbamoyl-ethyl]-amide;

[S-(R*,R*)]-2-[(4-Methoxy-benzyl)-methyl-amino]-4-methyl-pentanoic acid [2-(4-benzyloxy-phenyl)-1-tert-butylcarbamoyl-ethyl]-amide;

[S-(R*,R*)]4-Methyl-2-piperidin-1-yl-pentanoic acid [2-(4-benzyloxy-phenyl)-1-tert-butylcarbamoyl-ethyl]-amide;

[S-(R*,R*)]-2-Ethylamino4-methyl-pentanoic acid [2-(4-benzyloxy-phenyl)-1-tert-butylcarbamoyl-ethyl]-amide;

[S-(R*,R*)]-4-Methyl-2-(methyl-pyridin-3-ylmethyl-amino)-pentanoic acid [2-(4-benzyloxy-phenyl)-1-tert-butylcarbamoyl-ethyl]-amide;

[S-(R*,R*)]-3-(4-Benzyloxy-phenyl)-N-tert-butyl-2-{2-[methyl-(3-methyl-butyl)-amino]-acetylamino}-propionamide;

[S-[R*,R*,(RS)]]-2-(sec-Butyl-methyl-amino)-4-methyl-pentanoic acid [2-(4-benzyloxy-phenyl)-1-tert-butylcarbamoyl-ethyl]-amide;

(S)-N-[2-(4-Benzyloxy-phenyl)-1-tert-butylcarbarnoyl-ethyl]-2-(3-methyl-butylamino)-isobutyramide;

[S-(R*,R*)]-4-Methyl-2-(3-methyl-butylamino)-pentanoic acid [2-(4-benzyloxy-phenyl)-1-tert-butylcarbamoyl-ethyl]-amide;

4-Methyl-2-[methyl-(tetrahydro-pyran-4-yl)-amino]-pentanoic acid [2-(4-benzyloxyphenyl)-1-(1-methoxymethyl-propylcarbamoyl)-ethyl]-amide;

4-Methyl-2-[methyl-(3-methylbutyl)-amino]-pentanoic acid [2-(4-benzyloxyphenyl)-1-(1-methoxymethyl-propylcarbamoyl)-ethyl]-amide;

2-(Isopropyl-methyl-amino)4-methyl-pentanioc acid [2-(4-benzyloxyphenyl)-1-(1-methoxymethyl-propylcarbamoyl)-ethyl]-amide;

2-[(4-tert-butyl-benzyl)-methyl-amino]-4-methyl-pentanoic acid [2-(4-benzyloxyphenyl)-1-(1-methoxymethyl-propylcarbamoyl)-ethyl]-amide;

2-[(4-Dimethylamino-benzyl)-methyl-amino]-4-methyl-pentanoic acid [2-(4-benzyloxyphenyl)-1-(1-methoxymethyl-propylcarbamoyl)-ethyl]-amide;

4-Methyl-2-[methyl-tetrahydropyran-4-yl)-amino]-pentanoic acid [2-(4-benzyloxyphenyl)-1-(1-propyl-piperidin-3-ylcarbarnoyl)-ethyl]-amide;

4-Methyl-2-[methyl-(3-methyl-butyl-amino]-pentanoic acid [2-(4-benzyloxyphenyl)-1-(1-propyl-piperidin-3-ylcarbamoyl)-ethyl]-amide;

2-(Isopropyl-methyl-amino)-methyl-pentanoic acid [2-(4-benzyloxyphenyl)-1-(1-propyl-piperidin-3-ylcarbamoyl)-ethyl]-amide;

2-[(4-tertButyl-benzyl-)-methyl-amino]-4-methyl-pentanoic acid [2-(4-benzyloxyphenyl)-1-(1-propyl-piperidin-3-ylcarbamoyl)-ethyl]-amide;

2-[(4-Dimethylamino-benzyl)-methyl-amino]-4-methyl-pentanoic acid [2-(4-benzyloxyphenyl)-1-(1-propyl-piperidin-3-ylcarbamoyl)-ethyl]-amide;

[S, (R*,R*)]-4-Methyl-2-piperidin-1-yl-pentanoic acid [2-(4-benzyloxy-phenyl)-1-tert-butylcarbamoyl-ethyl]-amide;

[S, (R*,R*)]-4-Methyl-2-morpholin-4-yl-pentanoic acid [2-(4-benzyloxy-phenyl)-1-tert-butylcarbamoyl-ethyl]-amide monohydrochloride;

[S-(R*,R*)]-2-Dimethylamino-4-methyl-pentanoic acid {1-tert-butylcarbamoyl-2-[4-(pyridin-3-ylmethoxy)-phenyl]-ethyl}-amide;

[S-(R*,R*)]-2-(Cyclohexyl-methyl-amino)-4-methyl-pentanoic acid {1-tert-butylcarbamoyl-2-[4-(pyridin-3-ylmethoxy)-phenyl]-ethyl}-amide;

[S-(R*,R*)]-4-Methyl-2-[methyl-(3-methyl-butyl)-amino]-pentanoic acid {1-tert-butylcarbamoyl-2-[4-(pyridin-3-ylmethoxy)-phenyl]-ethyl}-amide;

[S-(R*,R*)]-2-[(4-tert-Butyl-benzyl)-methyl-amino]-4-methyl-pentanoic acid {1-tert-butylcarbamoyl-2-[4-(pyridin-3-ylmethoxy)-phenyl]-ethyl}-amide;

[S-(R*,R*)]-2-[(3-Methoxy-benzyl)-methyl-amino]-4-methyl-pentanoic acid [2-(4-benzyloxy-phenyl)-1-tert-butylcarbamoyl-ethyl]-amide;

[S-(R*,R*)]-2-[(2-Methoxy-benzyl)-methyl-amino]-4-methyl-pentanoic acid [2-(4-benzyloxy-phenyl)-1-tert-butylcarbamoyl-ethyl]-amide;

[S-(R*,R*)]-2-[(4-Chloro-benzyl)-methyl-amino]-4-methyl-pentanoic acid [2-(4-benzyloxy-phenyl)-1-tert-butylcarbamoyl-ethyl]-amide;

[S-(R*,R*)]-2-[(3-Chloro-benzyl)-methyl-amino]-4-methyl-pentanoic acid [2-(4-benzyloxy-phenyl)-1-tert-butylcarbamoyl-ethyl]-amide;

[S-(R*,R*)]-2-[(2-Chloro-benzyl)-methyl-amino]-4-methyl-pentanoic acid [2-(4-benzyloxy-phenyl)-1-tert-butylcarbamoyl-ethyl]-amide;

[S-(R*,R*)]-4-Methyl-2-[methyl-(4-methylsulfanyl-benzyl)-amino]-pentanoic acid [2-(4-benzyloxy-phenyl)-1-tert-butylcarbamoyl-ethyl]-amide;

[S-(R*,R*)]-4-Methyl-2-[methyl-(tetrahydro-pyran-4-yl)-amino]-pentanoic acid {2-(4-benzyloxy-phenyl)-1-[3-(2-oxo-pyrrolidin-1-yl)-propylcarbamnoyl]-ethyl}-amide;

[S-(R*,R*)]-4-Methyl-2-[methyl-(3-methyl-butyl)-amino]-pentanoic acid {2-(4-benzyloxy-phenyl)-1-[3-(2-oxo-pyrrolidin- 1 -yl)-propylcarbamoyl]-ethyl}-amide;

[S-(R*,R*)]-2-(sopropyl-methyl-amino)-4-methyl-pentanoic acid {2-(4-benzyloxy-phenyl)-1-[3-(2-oxo-pyrrolidin- 1-yl)-propylcarbamoyl]-ethyl}-amide;

[S-(R*,R*)]-2-[(3-Hydroxy-butyl)-methyl-amino]-4-methyl-pentanoic acid {2-(4-benzyloxy-phenyl)-1-[3-(2-oxo-pyrrolidin-1-yl)-propylcarbamoyl]-ethyl}-amide;

[S-(R*,R*)]-2-[(4-tert-Butyl-benzyl)-methyl-amino]4-methyl-pentanoic acid {2-(4-benzyloxy-phenyl)-1-[3-(2-oxo-pyrrolidin-1-yl)-propylcarbamoyl]-ethyl}-amide;

[S-(R*,R*)]-2-[(4-Dimethylamino-benzyl)-methyl-amino]-4-methyl-pentanoic acid {2-(4-benzyloxy-phenyl)-1-[3-(2-oxo-pyrrolidin-1-yl)-propylcarbamoyl]-ethyl}-amide;

[S-(R*,R*)]-2-(Isopropyl-methyl-amino)-4-methyl-pentanoic acid [2-(4-benzyloxy-phenyl)-1-(2-piperidin-1-yl-ethylcarbamoyl)-ethyl]-amide;

[S-(R*,R*)]-2-[(3-Hydroxy-butyl)-methyl-amino]-4-methyl-pentanoic acid [2-(4-benzyloxy-phenyl)-1-(2-piperidin-1-yl-ethylcarbamoyl)-ethyl]-amide;

[S-(R*,R*)]-2-[(4-tert-Butyl-benzyl)-methyl-amino]-4-methyl-pentanoic acid [2-(4-benzyloxy-phenyl)-1-(2-piperidin-1-yl-ethylcarbamoyl)-ethyl]-amide;

[S-(R*,R*)]-2-[(4-Dimethylamino-benzyl)-methyl-amino]-4-methyl-pentanoic acid [2-(4-benzyloxy-phenyl)-1-(2-piperidin-1-yl-ethylcarbamoyl)-ethyl]-amide;

[S-(R*,R*)]4-Methyl-2-[methyl-(tetrahydro-pyran-4-yl)-amino]-pentanoic acid [1-(4-benzyloxy-benzyl)-2-[1,4']bipiperidinyl-1'-yl-2-oxo-ethyl]-amide;

[S-(R*,R*)]-4-Methyl-2-[methyl-(3-methyl-butyl)-amino]-pentanoic acid [1-(4-benzyloxy-benzyl)-2-[1,4']bipiperidinyl- 1'-yl-2-oxo-ethyl]-amide;

[S-(R*,R*)]-2-(Isopropyl-methyl-amino)-4-methyl-pentanoic acid [1-(4-benzyloxy-benzyl)-2-[1,4']bipiperidinyl- 1'-yl-2-oxo-ethyl]-amide;

2-[(3-Hydroxy-butyl)-methyl-amino]-4-methyl-pentanoic acid [1-(4-benzyloxy-benzyl)-2-[1,4']bipiperidinyl-1'-yl-2-oxo-ethyl]-amide;

[S-(R*,R*)]-2-[(4-tert-Butyl-benzyl)-methyl-amino]-4-methyl-pentanoic acid [1-(4-benzyloxy-benzyl)-2-[1,4']bipiperidinyl-1'-yl-2-oxo-ethyl]-amide;

[S-(R*,R*)]-2-[(4-Dimethylamino-benzyl)-methyl-amino]-4-methyl-pentanoic acid [1-(4-benzyloxy-benzyl)-2-[1,4']bipiperidinyl-1'-yl-2-oxo-ethyl]-amide;

[S-(R*,R*)]-2-[(4-tert-Butyl-benzyl)-methyl-amino]-4-methyl-pentanoic acid [1-(2-benzylamino-ethylcarbamoyl)-2-(4-benzyloxy-phenyl)-ethyl]-amide;

[S-(R*,R*)]-2-[(4-Dimethylamino-benzyl)-methyl-amino]-4-methyl-pentanoic acid [1-(2-benzylamino-ethylcarbamoyl)-2-(4-benzyloxy-phenyl)-ethyl]-amide;

[S-(R*,R*)]-4-Methyl-2-[methyl-(tetrahydro-pyran-4-yl)-amino]-pentanoic acid [1-(2-benzylamino-ethylcarbamoyl)-2-(4-benzyloxy-phenyl)-ethyl]-amide;

[S-(R*,R*)]-4-Methyl-2-[methyl-(3-methyl-butyl)-amino]-pentanoic acid [1-(2-benzylamino-ethylcarbamoyl)-2-(4-benzyloxy-phenyl)-ethyl]-amide;

[S-(R*,R*)]-2-[(3-Hydroxy-butyl)-methyl-amino]-4-methyl-pentanoic acid [2-(4-benzyloxy-phenyl)-1-(1-propyl-piperidin-3-ylcarbamoyl)-ethyl]-amide;

[S-(R*,R*)]-4-Methyl-2-[methyl-(3-methyl-butyl)-amino]-pentanoic acid [2-(4-benzyloxy-phenyl)-1-(1-propyl-piperidin-3-ylcarbamoyl)-ethyl]-amide;

[S-(R*,R*)]-2-(Isopropyl-methyl-amino)-4-methyl-pentanoic acid [2-(4-benzyloxy-phenyl)-1-(3-imidazol-1-yl-propylcarbamoyl)-ethyl]-amide;

2-[(3-Hydroxy-butyl)-methyl-amino]-4-methyl-pentanoic acid [2-(4-benzyloxy-phenyl)-1-(1,1-bis-hydroxymethyl-propylcarbamoyl)-ethyl]-amide;

[S-(R*,R*)]-2-[(4-tert-Butyl-benzyl)-methyl-amino]-4-methyl-pentanoic acid [2-(4-benzyloxy-phenyl)-1-(1,1-bis-hydroxymethyl-propylcarbamoyl)-ethyl]-amide;

[S-(R*,R*)]-2-[(4-Dimethylamino-benzyl)-methyl-amino]-4-methyl-pentanoic acid [2-(4-benzyloxy-phenyl)-1-(1,1-bis-hydroxymethyl-propylcarbamoyl)-ethyl]-amide;

[S-(R*,R*)]-2-[(4-tert-Butyl-benzyl)-methyl-amino]-4-methyl-pentanoic acid [2-(4-benzyloxy-phenyl)-1-(3-imidazol-1-yl-propylcarbamoyl)-ethyl]-amide;

[S-(R*,R*)]-2-[(4-Dimethylamino-benzyl)-methyl-amino]4-methyl-pentanoic acid [2-(4-benzyloxy-phenyl)-1-(3-imidazol-1-yl-propylcarbamoyl)-ethyl]-amide;

[S-(R*,R*)]-2-(Isopropyl-methyl-amino)-4-methyl-pentanoic acid [2-(4-benzyloxy-phenyl)-1-(3-imidazol-1-yl-propylcarbamoyl)-ethyl]-amide;

[S-(R*,R*)]-2-[(3-Hydroxy-butyl)-methyl-amino]-4-methyl-pentanoic acid [2-(4-benzyloxy-phenyl)-1-(3-imidazol-1-yl-propylcarbamoyl)-ethyl]-amide;

[S-(R*,R*)]-2-(Isopropyl-methyl-amino)-4-methyl-pentanoic acid [2-(4-benzyloxy-phenyl)-1-(2-hydroxy-1,1-dimethyl-ethylcarbamoyl)-ethyl]-amide;

2-[(3-Hydroxy-butyl)-methyl-amino]-4-methyl-pentanoic acid [2-(4-benzyloxy-phenyl)-1-(2-hydroxy-1,1-dimethyl-ethylcarbamoyl)-ethyl]-amide;

2-[(4-tert-Butyl-benzyl)-methyl-amino]-4-methyl-pentanoic acid [2-(4-benzyloxy-phenyl)- 1-(2-hydroxy-1,1-dimethyl-ethylcarbamoyl)-ethyl]-amide;

2-[(4-Dimethylamino-benzyl)-methyl-amino]-4-methyl-pentanoic acid [2-(4-benzyloxy-phenyl)-1-(2-hydroxy-1,1-dimethyl-ethylcarbamoyl)-ethyl]-amide;

2-[(3-Hydroxy-butyl)-methyl-amino]-4-methyl-pentanoic acid [2-(4-benzyloxy-phenyl)- 1-(1-methoxymethyl-propylcarbamoyl)-ethyl]-amide;

[S-(R*,R*)]-4-Methyl-2-[methyl-(3-methyl-butyl)-amino]-pentanoic acid [2-(4-benzyloxy-phenyl)-1-(2-hydroxy-1,1-dimethyl-ethylcarbamoyl)-ethyl]-amide;

[S-(R*,R*)]-4-methyl-2-(3-methyl-butylamino)-pentanoic acid [2-(4-phenethyl-phenyl)-1-tert-butylcarbamoyl-ethyl] amide;

[S-(R*,R*)]-4-methyl-2-(3-methyl-butylamino)-pentanoic acid [2-(4-(2-cyclohexyl-ethyl)-phenyl)-1-tert-butylcarbamoyl-ethyl] amide;

[S-(R*,R*)]-4-methyl-2-(3-methyl-butylamino)-pentanoic acid [2-(4-(2-cyclopentyl-ethyl)-phenyl)-1-tert-butylcarbamoyl-ethyl] amide;

[S-(R*,R*)]-4-methyl-2-(3-methyl-butylamino)-pentanoic acid [2-(4-(2-cyclohexyl-ethyl)-phenyl)-1-(1,1-bis-hydroxymethyl-propylcarbamoyl)-ethyl] amide;

4-Methyl-2-[methyl-(tetrahydro-pyran-4-yl)-amino]-pentanoic acid [2-(4-benzyloxyphenyl)-1-(1-methoxymethyl-propylcarbamoyl)-ethyl]-amide;

4-Methyl-2-[methyl-(3-methylbutyl)-amino]-pentanoic acid [2-(4-benzyloxy-phenyl)-1-(1-methoxymethyl-propylcarbamoyl)-ethyl]-amide;

2-(Isopropyl-methyl-amino)-4-methyl-pentanioc acid [2-(4-benzyloxyphenyl)-1-(1-methoxymethyl-propylcarbamoyl)-ethyl]-amide;

2-[(4-tert-butyl-benzyl)-methyl-amino]-4-methyl-pentanoic acid [2-(4-benzyloxyphenyl)-1-(1-methoxymethyl-propylcarbamoyl)-ethyl]-amide;

2-[(4-Dimethylamino-benzyl)-methyl-amino]-4-methyl-pentanoic acid [2-(4-benzyloxyphenyl)-1-(1-methoxymethyl-propylcarbamoyl)-ethyl]-amide;

4-Methyl-2-[methyl-tetrahydropyran-4-yl)-amino]-pentanoic acid [2-(4-benzyloxyphenyl)-1-(1-propyl-piperidin-3-ylcarbamoyl)-ethyl]-amide;

4-Methyl-2-[methyl-(3-methyl-butyl-amino]-pentanoic acid [2-(4-benzyloxyphenyl)-1-(1-propyl-piperidin-3-ylcarbamoyl)-ethyl]-amide;

2-(Isopropyl-methyl-amino)-methyl-pentanoic acid [2-(4-benzyloxyphenyl)-1-(1-propyl-piperidin-3-ylcarbamoyl)-ethyl]-amide;

2-[(4-tertButyl-benzyl-)-methyl-amino]-4-methyl-pentanoic acid [2-(4-benzyloxyphenyl)-1-(1-propyl-piperidin-3-ylcarbanoyl)-ethyl]-amide; and 2-[(4-Dimethylamino-benzyl)-methyl-amino]-4-methyl-pentanoic acid [2-(4-benzyloxy phenyl)-1-(1-propyl-piperidin-3-ylcarbamoyl)-ethyl]-amide.

DETAILED DESCRIPTION OF THE INVENTION

The present invention provides compounds having the Formula I

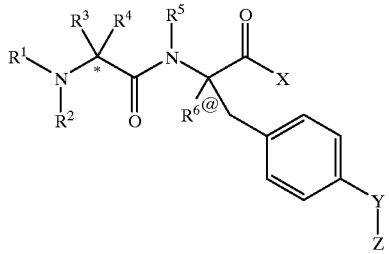

wherein

* denotes a first chiral center when $R^3$ and $R^4$ are different;

@ denotes a second chiral center;

$R^1$ and $R^2$ are independently hydrogen, $C_1$–$C_8$alkyl, $C_3$–$C_7$cycloalkyl,
$C_3$–$C_8$substituted alkyl, $C_1$–$C_6$alkoxy, hydroxy, $C_3$–$C_6$heterocycloalkyl,
$C_3$–$C_7$cycloalkenyl, $C_3$–$C_7$substituted, cycloalkenyl, $C_3$–$C_7$substituted cycloalkyl, —(CH$_2$)$_n$-aryl, (CH$_2$)$_n$-substituted aryl, $C_2$–$C_8$alkenyl,
$C_2$–$C_8$ substituted alkenyl,

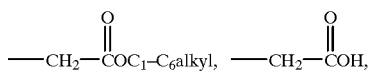

—(CH$_2$)$_n$-heteroaryl, —(CH$_2$)$_n$-substituted heteroaryl, —(CH$_2$)$_n$—$C_3$–$C_7$heterocycle, —(CH$_2$)$_n$-substituted $C_3$–$C_7$heterocycle, —(CH$_2$)$_n$-cycloalkyl, —(CH$_2$)$_n$-substituted cycloalkyl, or $R^1$ and $R^2$ may be taken together to form a 5- to 7-membered ring which may contain heteroatoms, provided that $R^1$ and $R^2$ are not both hydrogen;

$R^3$, $R^5$, and $R^6$ are independently hydrogen or $C_1$–$C_8$alkyl;

$R^4$ is $C_1$–$C_8$alkyl,
—(CH$_2$)$_n$$C_3$–$C_7$cycloalkyl,
—(CH$_2$)$_n$$C_3$–$C_7$substituted cycloalkyl, or
—(CH$_2$)$_n$phenyl;

Y is —(CH$_2$)$_n$—, —O(CH$_2$)$_n$—, —(CH$_2$)$_n$O—, —N(R$^3$)(CH$_2$)$_n$—, —(CH$_2$)$_n$N(R$^3$)—, —S(CH$_2$)$_n$—, —(CH$_2$)$_n$S—, —C=C—, or —C≡C—;

Z is aryl, substituted aryl, heteroaryl, substituted heteroaryl, $C_3$–$C_7$cycloalkyl, substituted $C_3$–$C_7$cycloalkyl, or $C_1$–$C_8$alkyl;

X is heterocycle, substituted heterocycle,
—NH(CH$_2$)$_n$NR$^3$R$^5$,
—NH(CH$_2$)$_n$heteroaryl,
—NH(CH$_2$)$_n$substituted heteroaryl,
—NH(CH$_2$)$_n$NH(CH$_2$)$_n$phenyl,
—NH(CH$_2$)$_n$NH(CH$_2$)$_n$—OH,
—NH-heterocycle-CH$_2$phenyl,

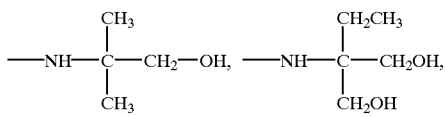

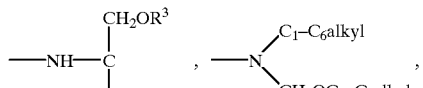

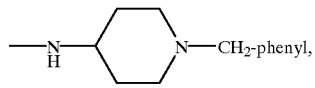

—NH(CH$_2$)$_n$-heterocycloalkyl,
—OC$_1$–C$_6$alkyl,

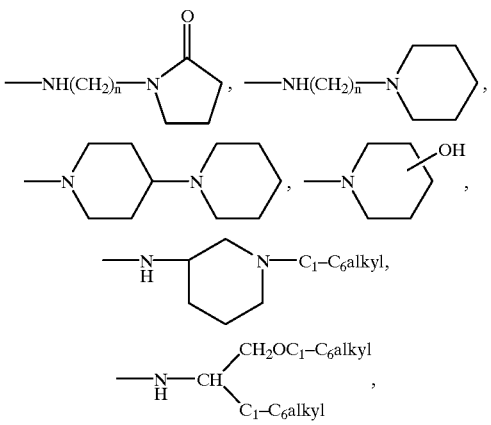

—NH(CH$_2$)$_n$heterocycle,
—NH(CH$_2$)$_n$substituted heterocycle;
—OR$^3$, —NHR$^3$, —NR$^3$R$^5$, wherein in addition to the definitions of R$^3$ and R$^5$ above, R$^3$ and R$^5$ can together with the nitrogen atom form a ring having from 3 to 7 atoms;

each n is 0 to 5, and the pharmaceutically acceptable salts, esters, amides, and prodrugs thereof.

Two chiral centers that can have either R or S configurations are designated above in Formula I by the symbols "*" and "@". It is intended that the present invention cover compounds having the S,S; R,R; S,R; or R,S configurations and mixtures thereof.

The term "alkyl" means a straight or branched chain hydrocarbon. Representative examples of alkyl groups are methyl, ethyl, propyl, isopropyl, isobutyl, butyl, tert-butyl, sec-butyl, pentyl, and hexyl.

The term "alkoxy" means an alkyl group attached to an oxygen atom. Representative examples of alkoxy groups include methoxy, ethoxy, tert-butoxy, propoxy, and isobutoxy.

The term "halogen" includes chlorine, fluorine, bromine, and iodine.

The term "alkenyl" means a branched or straight chain hydrocarbon having one or more carbon-carbon double bond.

The term "aryl" means an aromatic hydrocarbon. Representative examples of aryl groups include phenyl and naphthyl.

The term "heteroatom" includes oxygen, nitrogen, and sulfur.

The term "heteroaryl" means an aryl group wherein one or more carbon atom of the aromatic hydrocarbon has been replaced with a heteroatom. Examples of heteroaryl radicals include, but are not limited to, pyridyl, imidazolyl, pyrrolyl, thienyl, furyl, pyranyl, pyrimidinyl, pyridazinyl, indolyl, quinolyl, naphthyridinyl, and isoxazolyl.

The term "cycloalkyl" means a cyclic hydrocarbon. Examples of cycloalkyl groups include cyclopropyl, cyclobutyl, cyclopentyl, and cyclohexyl.

The symbol "—" means a bond.

The term "patient" means all animals including humans. Examples of patients include humans, cows, dogs, cats, goats, sheep, and pigs.

The term "substituted" means that the base organic radical has one or more substituents. For example, substituted cyclohexyl means a cyclohexyl radical that has one or more substituents. Substituents include, but are not limited to, halogen, $C_1$–$C_8$alkyl, —CN, $CF_3$, —$NO_2$, —$NH_2$, —$NHC_1$–$C_8$alkyl, —N($C_1$–$C_8$alkyl)$_2$, —SC 1–$C_8$alkyl, —$OC_1$–$C_8$alkyl, and —OH. Particularly preferred substituents include, but are not limited to tert-butyl, methyl, chlorine, fluorine, bromine, —$OCH_3$, —$OCH_2CH_3$, —OH, and —N($CH_3$)$_2$.

The term "cycloalkenyl" means a cycloalkyl group having at least one carbon-carbon double bond. Examples of cycloalkenyl groups include cyclopentene, cyclobutene, and cyclohexene.

The term "heterocycle" means a cycloalkyl group wherein one or more carbon atom is replaced with a heteroatom. Examples of heterocycles include, but are not limited to, pyrrolidinyl, piperidinyl, and piperazinyl.

Those skilled in the art are easily able to identify patients having a stroke or at risk of having a stroke; cerebral ischemia; head trauma; or epilepsy. For example, patients who are at risk of having a stroke include, but is not limited to patients having hypertension or undergoing major surgery.

A therapeutically effective amount is an amount of a compound of Formula I, that when administered to a patient, ameliorates a symptom of the disease.

The compounds of the present invention can be administered to a patient either alone or a part of a pharmaceutical composition. The compositions can be administered to patients either orally, rectally, parenterally (intravenously, intramuscularly, or subcutaneously), intracisternally, intravaginally, intraperitoneally, intravesically, locally (powders, ointments, or drops), or as a buccal or nasal spray.

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, carboxymethylcellulose, alignates, gelatin, polyvinylpyrrolidone, sucrose, and acacia, (c) humectants, as for example, glycerol, (d) disintegrating agents, as for example, agar-agar, calcium carbonate, potato or tapioca starch, alginic acid, certain complex silicates, and sodium carbonate, (e) solution retarders, as for example paraffin, (f) absorption accelerators, as for example, quaternary ammonium compounds, (g) wetting agents, as for example, cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragées, capsules, pills, and granules can be prepared with coatings and shells, such as enteric coatings and others well known in the art. They may contain opacifying agents, and can also be of such composition that they release the active compound or compounds in a certain part of the intestinal tract in a delayed manner. Examples of embedding compositions which can be used are polymeric substances and waxes. The active compounds can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan or mixtures of these substances, and the like.

Besides such inert diluents, the composition can also include adjuvants, such as wetting agents, emulsifying and suspending agents, sweetening, flavoring, and perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are preferably suppositories which can be prepared by mixing the compounds of the present invention with suitable non-irritating excipients or carriers such as cocoa butter, polyethyleneglycol or a suppository wax, which are solid at ordinary temperatures but liquid at body temperature and therefore, melt in the rectum or vaginal cavity and release the active component.

Dosage forms for topical administration of a compound of this invention include ointments, powders, sprays, and inhalants. The active component is admixed under sterile conditions with a physiologically acceptable carrier and any preservatives, buffers, or propellants as may be required. Ophthalmic formulations, eye ointments, powders, and solutions are also contemplated as being within the scope of this invention.

The term "pharmaceutically acceptable salts, esters, amides, and prodrugs" as used herein refers to those carboxylate salts, amino acid addition salts, esters, amides, and prodrugs of the compounds of the present invention which are, within the scope of sound medical judgment, suitable for use in contact with the tissues of patients without undue toxicity, irritation, allergic response, and the like, commensurate with a reasonable benefit/risk ratio, and effective for their intended use, as well as the zwitterionic forms, where possible, of the compounds of the invention. The term "salts" refers to the relatively non-toxic, inorganic and organic acid addition salts of compounds of the present invention. These salts can be prepared in situ during the final isolation and purification of the compounds or by separately reacting the purified compound in its free base form with a suitable organic or inorganic acid and isolating the salt thus formed. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate and laurylsulphonate salts, and the like. These may include cations based on the alkali and alkaline earth metals, such as sodium, lithium, potassium, calcium, magnesium, and the like, as well as non-toxic ammonium, quaternary ammonium and amine cations including, but not limited to ammonium, tetramethylammonium, tetraethylammonium, methylamine, dimethylamine, trimethylamine, triethylamine, ethylamine, and the like. (See, for example, S. M. Berge, et al., "Pharmaceutical Salts," *J. Pharm. Sci.,* 1977;66:1–19 which is incorporated herein by reference.)

Examples of pharmaceutically acceptable, non-toxic esters of the compounds of this invention include $C_1$–$C_6$alkyl esters wherein the alkyl group is a straight or branched chain. Acceptable esters also include $C_5$–$C_7$cycloalkyl esters as well as arylalkyl esters such as, but not limited to benzyl. $C_1$–$C_4$alkyl esters are preferred. Esters of the compounds of the present invention may be prepared according to conventional methods.

Examples of pharmaceutically acceptable, non-toxic amides of the compounds of this invention include amides derived from ammonia, primary $C_1$–$C_6$alkyl amines and secondary $C_1$–$C_6$dialkyl amines wherein the alkyl groups are straight or branched chain. In the case of secondary amines the amine may also be in the form of a 5- or 6-membered heterocycle containing one nitrogen atom. Amides derived from ammonia, $C_1$–$C_3$alkyl primary amines, and $C_1$–$C_2$dialkyl secondary amines are preferred. Amides of the compounds of the invention may be prepared according to conventional methods.

The term "prodrug" refers to compounds that are rapidly transformed in vivo to yield the parent compound of the above formulae, for example, by hydrolysis in blood. A thorough discussion is provided in T. Higuchi and V. Stella, "Pro-drugs as Novel Delivery Systems," Vol 14 of the A.C.S. Symposium Series, and in *Bioreversible Carriers in Drug Design,* ed. Edward B. Roche, American Pharmaceutical Association and Pergamon Press, 1987, both of which are incorporated herein by reference.

In addition, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention.

The compounds of the present invention can exist in different stereoisomeric forms by virtue of the presence of asymmetric centers in the compounds. It is contemplated that all stereoisomeric forms of the compounds, as well as mixtures thereof including racemic mixtures, form part of this invention.

The compounds of the present invention can be administered to a patient at dosage levels in the range of about 0.1 to about 1,000 mg per day. For a normal human adult having a body weight of about 70 kilograms, a dosage in the range of about 0.01 to about 100 mg per kilogram of body weight per day is preferable. The specific dosage used, however, can vary. For example, the dosage can depended on a numbers of factors including the requirements of the patient, the severity of the condition being treated, and the pharmacological activity of the compound being used. The determination of optimum dosages for a particular patient is well known to those skilled in the art.

In addition, it is intended that the present invention cover compounds made either using standard organic synthetic techniques, including combinatorial chemistry or by biological methods, such as through metabolism.

The examples presented below are intended to illustrate particular embodiments of the invention and are not intended to limit the scope of the specification, including the claims, in any way.

The following abbreviations are used throughout this application:

| | |
|---|---|
| Pr | Propyl |
| Et | Ethyl |
| HBTU | 2-(1H-benzotriazol-1-yl)-1,1,3,3-tetramethyl uranium hexafluorophosphate |
| Bz or Bn | Benzyl |
| TFA | Trifluoroacetic acid |
| APCI | Atmospheric pressure chemical ionization |
| NMR | Nuclear magnetic resonance |
| TLC | Thin layer chromatography |
| HPLC | High pressure liquid chromatography |
| DMF | Dimethyl formamide |
| EtOAC | Ethyl acetate |
| EtOH | Ethanol |
| MS | Mass spectrum |
| DCM | Dichloromethane |
| Et$_3$N | Triethyl amine |
| THF | Tetrahydrofuran |
| IR | Infrared |
| OAc | Acetate |
| bu | Butyl |
| iso-pr | Iso-propyl |
| FMOC | 9-Fluorenylmethyloxycarbonyl |
| BOC | Tertiary butyloxycarbonyl |

EXAMPLES

Synthesis

Scheme IV below illustrates the preparation of N,N-disubstituted-leucine-(OBz)-tyrosine amides (IV) using polymer supported resins in synthesis. The preparation of Tyrosine-(O-Benzyl)-amides (intermediates 1) are illustrated in Scheme I. The preparation of N,N-dialkyl leucine acids (intermediates II) are illustrated in Schemes II and III.

Step I: The Preparation of Tyrosine-(OBenzyl)-Amides (I)

Scheme I

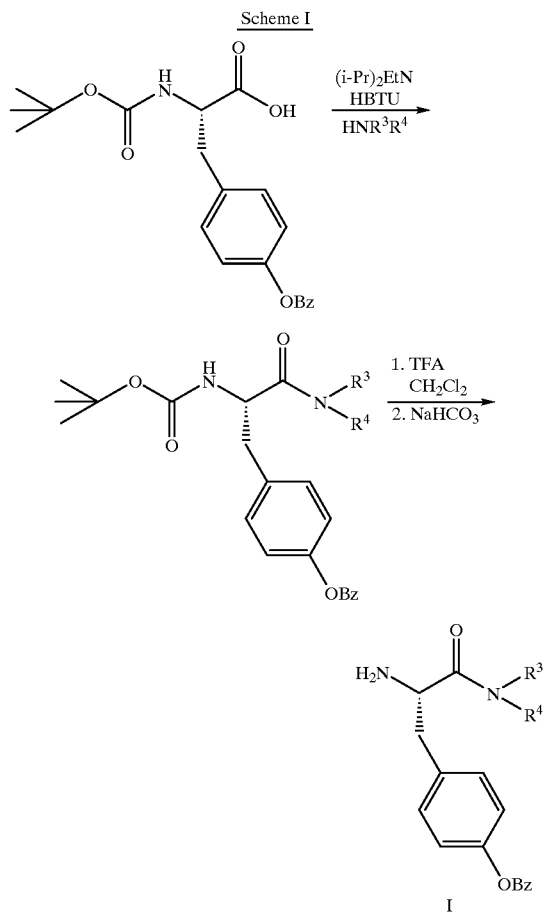

Step II: The Preparation of N,N-dialkyl Leucine Acids (II)

Schemes II and III illustrate general methods of preparing N,N-dialkyl Leucine acids (II).

Scheme II

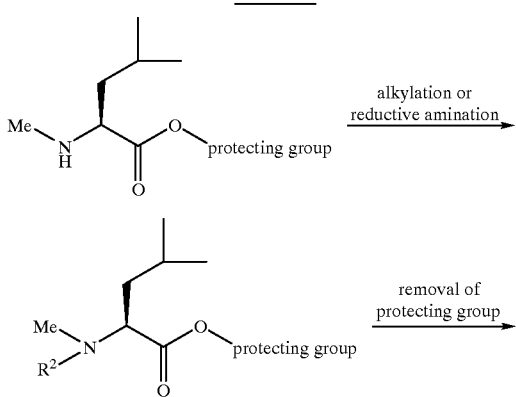

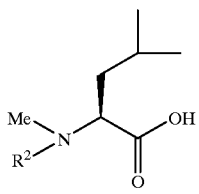

Scheme III

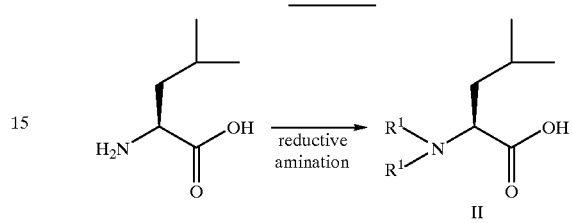

Step III: The preparation of N,N-disubstituted-Leucine-(OBz)-Tyrosine amides (IV)

Scheme IV

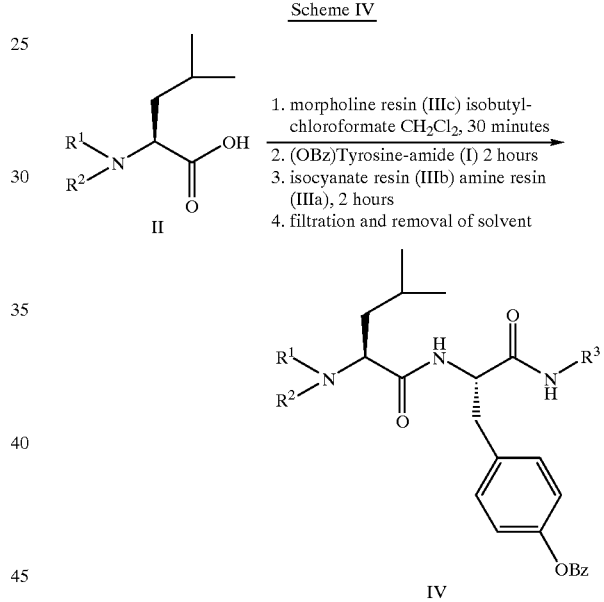

N,N-Dialkyl leucine acid [II, 0.1 mmol, 1 equivalent (eq.)] was placed in a 2 dram vial and morpholine resin (IIIc, 150 mg, 3.6 mmol/g, 5.4 eq.) was added. The mixture was treated with dichloromethane (1.5 mL) and isobutylchloroformate (18 μL, 1.4 eq.). The vial was capped and shaken for 30 minutes. The (O-benzyl)-tyrosine amide (I, 0.1 mmol, 1 eq.) was added as a solution in dichloromethane (1 mL), and the mixture was shaken for 2 hours. Isocyanate resin (IIIb, 100 mg, 1.5 mmol/g, 1.5 eq.) and amine resin (IIIa, 100 mg, 1.5 mmol/g, 1.5 eq.) were added, and the mixture was shaken for 2 hours. The solids were filtered away through a plug of glass wool in a pipette. The solids were rinsed with 1 mL dichloromethane, and the combined solvent volume was evaporated under a stream of $N_2$. The product was analyzed by APCI mass spectrometry, $^1H$ NMR, TLC ($SiO_2$), and HPLC.

Example 1
[S-(R*,R*)]-2-Dimethylamino-4-methyl-pentanoic acid [2-(4-benzyloxy-phenyl)-1-tert-butylcarbamoyl-ethyl]-amide Step 1: The Preparation of (S)-2-Amino-3-(4-benzyloxy-phenyl)-N-tert-butyl-propionamide (Ia)

Scheme V

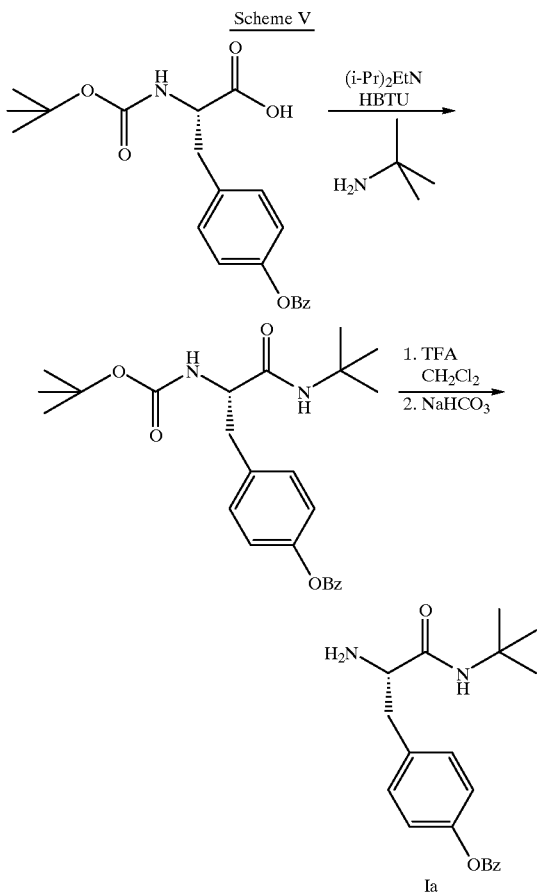

Step i: N-Boc-O-Benzyl-tyrosine (20.0 g, 53.9 mmol) was dissolved in DMF (270 mL) and treated with diisopropylethylamine (19 mL, 108 mmol), tert-butylamine (5.7 mL. 53.9 mmol), and HBTU (13.9 g, 53.9 mmol). The reaction was stirred for 15 minutes and then diluted with EtOAc (1 L), washed with saturated bicarbonate solution (2×1 L) and brine (1 L), dried over $Na_2SO_4$ and concentrated to give 22.1 g (92%) of (S)-[2-(4-benzyloxyphenyl)-1-tert-butylcarbamoyl-ethyl]-carbamic acid tert-butyl ester.

MS: 428 (M+1 for $C_{25}H_{34}N_2O_4$); TLC: $SiO_2$, $R_f$ 0.49 (10% $MeOH/CH_2Cl_2$).

Step ii: (S)-[2-(4-Benzyloxy-phenyl)-1-tert-butylcarbamoyl-ethyl]-carbamic acid tert-butyl ester (6.0 g, 14.1 mmol) was dissolved in $CH_2Cl_2$ (28 mL) and treated with trifluoroacetic acid (28 mL). The reaction was stirred for 20 minutes and then concentrated. The residue was diluted with EtOAc (300 mL), washed with saturated bicarbonate solution (2×300 mL) and brine (300 mL), dried over $Na_2SO_4$, and concentrated to give 4.2 g (91%) of Ia.

MS: 328 (M+1 for $C_{20}H_{26}N_2O_3$); TLC: $SiO_2$, $R_f$ 0.43 (10% $MeOH/CH_2Cl_2$).

Step 2: The Preparation of (S)-2-(Dimethyl-amino)-4-methyl-pentanoic acid (IIa)

Scheme VI

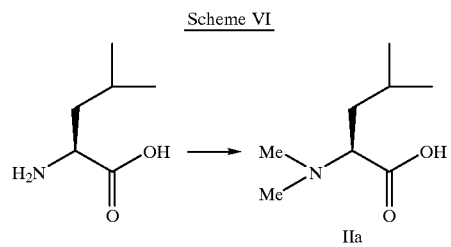

(S)-2-Amino-4-methyl-pentanoic acid (10.42 g, 80 mmol) was dissolved in $H_2O$ (120 mL) and treated with formaldehyde (80 mL, 37% solution), and Raney Nickel (2 g), and stirred for 21 hours. The solution was concentrated to a solid, dissolved in hot EtOH, boiled with charcoal, and filtered through Celite. The solution was allowed to cool. Acetone was added, and the solution was placed in the refrigerator. The solution was filtered and the crystals were washed with acetone to give 9.7 g (77%) of IIa.

MS: 160 (M+1 for $C_8H_{17}N_1O_2$); TLC $SiO_2$, $R_f$0.04 (12% $MeOH/CH_2Cl_2$).

Step 3: The Preparation of Polymer-supported Resins (III)
The Preparation of the Polymer-supported Tris(2-aminoethyl)Amine (IIIa)

A suspension of Merrifield resin (Fluka, 50 g, 1.7 mmol Cl/g resin, 85 mmol) in DMF (500 mL) was treated with tris(2-aminoethyl)amine (50 mL, 342 mmol). The resulting mixture was shaken at 65° C. for 6 hours under $N_2$ atmosphere. After cooling to room temperature, the resin was filtered and washed successively with MeOH, DMF, $Et_3N$, MeOH, DCM, $Et_3N$, MeOH, DCM, MeOH, DCM, and MeOH. The resulting amine resin was dried at 45–50° C., 20 mmHg for 24 hours, and stored in tightly sealed bottles. Calc'd: N, 8.02; Cl, 0.00. Found: N, 5.96; Cl, 0.42 (indicates approx. 25% cross-linking). A small sample reacted with excess 3,4-dichlorophenyl isocyanate in DCM indicates a quenching capacity of 3.18 mmol/g resin, consistent with three-quarters of the N content in the amine resin (IIIa). Calc'd: N, 6.51; Cl, 14.15. Found: N, 6.25; Cl, 13.99.

The Preparation of the Polymer-Supported Isocyanate (IIIb)

A suspension of aminomethyl resin (Fluka, 1.1 mmol N/g resin, 15 g, 16.5 mmol) in DCM (150 mL) was treated with $Et_3N$ (11.5 mL, 83 mmol) and triphosgene (3.25 g, 2 mmol equivalents of phosgene) and shaken 5 hours at room temperature. The resulting isocyanate resin was filtered and washed DCM (2×200 mL), $CHCl_3$ (2×200 mL), $Et_2O$ (1×200 mL), THF (1×200 mL), $Et_2O$ (1×200 mL), THF (1×200 mL), and $Et_2O$ (1×200 mL). The resin was then dried at 35–40° C., 25 mmHg for 24 hours. Yield (15 g of IIIb) IR (KBr) 2260 (N=C=O). Calc'd: C,; N,; Found: C, 87.04; N, 1.45.

The Preparation of the Polymer-Supported Morpholine (IIIc)

A suspension of Merrifield resin (Fluka, Ronkankoma, New York, 20 g, 4.3 mmol Cl/g resin, 86 mmol) in DMF (100 mL) was treated with morpholine (20 mL, 229 mmol). The resulting mixture was shaken at 65° C. for 6 hours under $N_2$ atmosphere, then allowed to stand at room temperature 24 hours. After cooling to room temperature, the resin was filtered and washed successively with MeOH, DMF, MeOH, $Et_3N$, DCM, MeOH, $Et_3N$, DCM, MeOH, EtOAc, and Hexanes. The resulting N-methylmorpholine resin (IIIc) was dried at 45–50° C., 20 mmHg for 48 hours, and stored in tightly sealed bottles. Calc'd. N, 4.83; Cl, 0.00. Found: N, 4.98; Cl, 0.21.

Step 4: Example 1: [S-(R*,R*)]-2-Dimethylamino-4methyl-pentanoic acid [2-(4-benzyloxy-phenyl)-1-tert-butylcarbamoyl-ethyl]-amide

Scheme VII

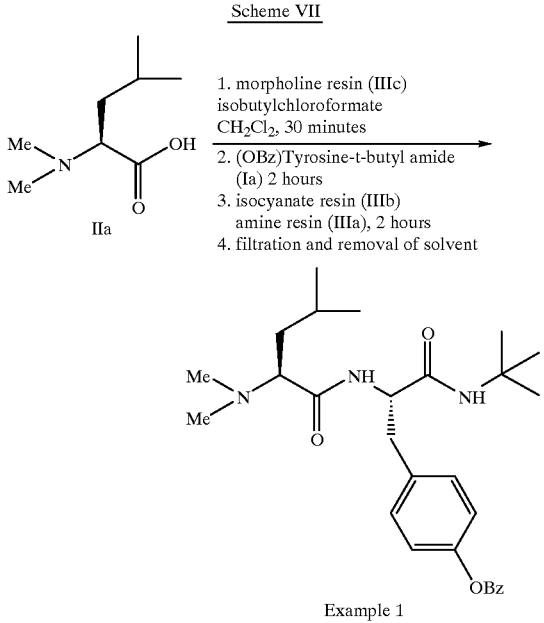

Example 1

N,N-Dimethyl-L-leucine (IIa, 15.9 mg, 0.1 mmol) and morpholine resin (IIIc, 150 mg, 0.54 mmol) were treated with $CH_2Cl_2$ (1.5 mL) and isobutylchloroformate (18 μL, 0.14 mmol). The vial was capped and shaken for 30 minutes. O-Benzyl-L-tyrosine-t-butyl-amide (Ia, 32.6 mg, 0.1 mmol) was added as a solution in dichloromethane (1 mL), and the mixture was shaken for 2 hours. Isocyanate resin (IIIb, 100 mg, 0.15 mmol) and amine resin (IIIa, 100 mg, 0.15 mmol) were added, and the mixture was shaken for 2 hours. The solids were filtered away through a plug of glass wool in a pipette. The solids were rinsed with 1 mL dichloromethane, and the combined solvent volume was evaporated under a stream of $N_2$ to give 41 mg (88%) of the title compound (Example 1).
MS: 469 (M+1 for $C_{28}H_{41}N_3O_3$); TLC: $SiO_2$, $R_f$ 0.56 (10% $MeOH/CH_2Cl_2$).

Example 2

[S-(R*,R*)]-2-Dimethylamino-4-methyl-pentanoic acid [2-(4-benzyloxy-phenyl)-1-(piperidine-1-carbonyl)-ethyl]-amide Step 1: The preparation of (S)-2-Amino-3-(4-benzyloxy-phenyl)-N-(piperidin-1-yl)-propionamide (Ib): Ib is made in accordance in the process of Ia, except piperidine was used instead of t-butylamine.
Step 2: Example 2: [S-(R*,R*)]-2-Dimethylamino-4-methyl-pentanoic acid [2-(4-benzyloxy-phenyl)-1-(piperidine-1-carbonyl)-ethyl]-amide is made in accordance with the process of Example 1, except (S)-2-amino-3-(4-benzyloxy-phenyl)-N-(piperidin-1-yl)-propionamide (Ib) was used instead of (S)-2-amino-3-(4-benzyloxy-phenyl)-N-tert-butyl-propionamide.
MS: 481 (M+1 for $C_{29}H_{41}N_3O_3$); sticky solid; TLC: $R_f$ 0.52 (10% $MeOH/CH_2Cl_2$).

Example 3

[S-(R*,R*)]-2-Dimethylamino-4-methyl-pentanoic acid [2-(4-benzyloxy-phenyl)-1-(2-piperidin-1-yl-ethylcarbamoyl)-ethyl]-amide Step 1: The preparation of (S)-2-Amino-3-(4-benzyloxy-phenyl)-N-(2-piperidin-1-yl-ethyl)-propionamide (Ic): Ic is made in accordance in the process of Ia, except 2-piperidinyl 1-ethylamine was used instead of t-butylamine.
Step 2: Example 3: [S-(R*,R*)]-2-Dimethylamino-4-methyl-pentanoic acid [2-(4-benzyloxy-phenyl)-1-(2-piperidin-1-yl-ethylcarbamoyl)-ethyl]-amide is made in accordance with the process of Example 1, except (S)-2-amino-3-(4-benzyloxy-phenyl)-N-(2-piperidin-1-yl-ethyl)-propionamide (Ic) was used instead of (S)-2-amino-3-(4-benzyloxy-phenyl)-N-tert-butyl-propionamide.
MS: 524 (M+1 for $C_{31}H_{46}N_4O_3$); sticky solid; TLC: $R_f$ 0.16 (10% $MeOH/CH_2Cl_2$).

Example 4

[S-(R*,R*)]-2-Dimethylamino-4-methyl-pentanoic acid [1-(4-benzyloxy-benzyl)-2-(4-benzyl-piperazin-1-yl)-2-oxo-ethyl]-amide Step 1: The preparation of (S)-2-Amino-3-(4-benzyloxy-phenyl)-1-(4-benzyl-piperazin-1-yl)-propan-1-one (Id): Id is made in accordance in the process of Ia, except 4-benzyl-piperazine was used instead of t-butylamine.
Step 2: Example 4: [S-(R*,R*)]-2-Dimethylamino-4-methyl-pentanoic acid [1-(4-benzyloxy-benzyl)-2-(4-benzyl-piperazin-1-yl)-2-oxo-ethyl]-amide is made in accordance with the process of Example 1, except (S)-2-amino-3-(4-benzyloxy-phenyl)-1-(4-benzyl-piperazin-1-yl)-propan-1-one (Id) was used instead of (S)-2-amino-3-(4-benzyloxy-phenyl)-N-tert-butyl-propionamide.
MS: 572 (M+1 for $C_{35}H_{46}N_4O_3$); sticky solid; TLC: $R_f$ 0.55 (10% $MeOH/CH_2Cl_2$).

Example 5

[S-(R*,R*)]-2-Dimethylamino-4-methyl-pentanoic acid [2-(4-benzyloxy-phenyl)-1-(1-benzyl-piperidin-4-yl-carbamoyl)-ethyl]-amide Step 1. (S)-2-Amino-3-(4-benzyloxy-phenyl)-N-(1-benzyl-piperidin-4-yl)-propionamide (Ie): Ie is made in accordance with the process of Ia, except 4-amino-1-benzyl-piperidine was used instead of t-butylamine.
Step 2. Example 5: [S-(R*,R*)]-2-Dimethylamino-4-methyl-pentanoic acid [2-(4-benzyloxy-phenyl)-1-(1-benzyl-piperidin-4-yl-carbamoyl)-ethyl]-amide is made in accordance with the process of Example 1, except (S)-2-amino-3-(4-benzyloxy-phenyl)-N-(1-benzyl-piperidin-4-yl)-propionamide (Ie) was used instead of (S)-2-amino-3-(4-benzyloxy-phenyl)-N-tert-butyl-propionamide.
MS: 586 (M+1 for $C_{36}H_{48}N_4O_3$); sticky solid; TLC: $R_f$ 0.44 (10% $MeOW/CH_2Cl_2$).

Example 6

[S-(R*,R*)]-2-Dimethylamino-4-methyl-pentanoic acid [1-(4-benzyloxy-benzyl)-2-(4-methyl-piperazin-1-yl)-2-oxo-ethyl]-amide Step 1. (S)-2-Amino-3-(4-benzyloxy-phenyl)-1-(4-methyl-piperazin-1-yl)-propan-1-one (If): If is made in accordance with the process of Ia, except 4-methylpiperazine was used instead of t-butylamine.
Step 2. Example 44: [S-(R*,R*)]-2-Dimethylamino-4-methyl-pentanoic acid [1-(4-benzyloxy-benzyl)-2-(4-methyl-piperazin-1-yl)-2-oxo-ethyl]-amide is made in accordance with the process of Example 1, except (S)-2-amino-3-(4-benzyloxy-phenyl)-1-(4-methyl-piperazin-1-yl)-propan-1-one (If) was used instead of (S)-2-amino-3-(4-benzyloxy-phenyl)-N-tert-butyl-propionamide.

MS: 495 (M+1 for $C_{29}H_{42}N_4O_3$); sticky solid; TLC: $R_f$0.66 (10% MeOH/$CH_2Cl_2$).

Example 7

[S-(R*,R*)]-4-Methyl-2-[methyl-(3-methyl-butyl)-amino]-pentanoic acid [2-(4-benzyloxy-phenyl)-1-tert-butylcarbamoyl-ethyl]-amide Step 1: The preparation of (S)-4-Methyl-2-[methyl-(3-methyl-butyl)-amino]-pentanoic acid IIb)

Scheme VIII

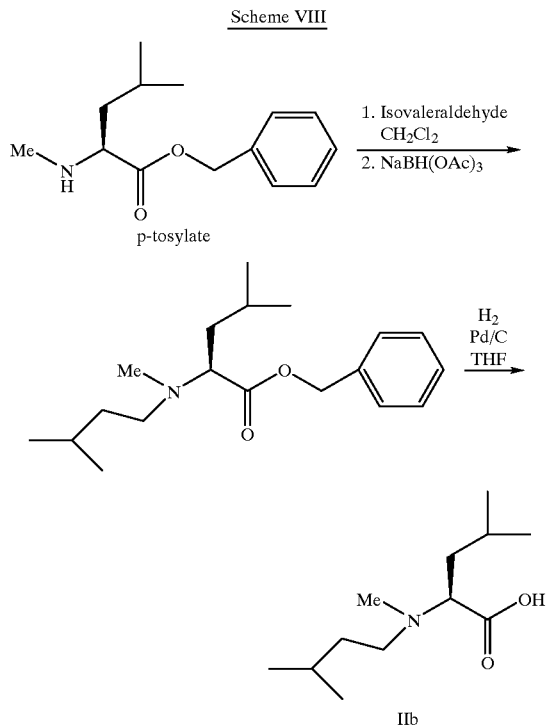

Step i: N-Methyl-O-benzyl-L-leucine p-tosylate salt (4.01 g, 9.84 mmol) was dissolved in $CH_2Cl_2$ (50 mL) and treated with isovaleraldehyde (1.06 mL, 9.84 mmol). The reaction was stirred at room temperature for 30 minutes and then cooled to 0° C. Sodium triacetoxyborohydride (3.13 g, 14.8 mmol) was added, and the reaction was allowed to warm to room temperature and stir overnight. The reaction was diluted with $CH_2Cl_2$ (400 mL). The organic layer was washed twice with saturated bicarbonate solution (2×400 mL), once with brine (400 mL), and then dried over $Na_2SO_4$. The solution was filtered, concentrated, and the crude material chromatographed on silica gel eluting with 10% EtOAc/hexanes to give 2.86 g (90%) of (S)4-methyl-2-[methyl-(3-methyl-butyl)-amino]-pentanoic acid benzyl ester as a pale oil.

MS: 306 (M+1 for $C_{19}H_{31}N_1O_2$); TLC: $SiO_2$, $R_f$0.33 (10% EtOAc/hexanes).

Step ii: (S)-4-Methyl-2-[methyl-(3-methyl-butyl)-amino]-pentanoic acid benzyl ester (0.89 g, 2.89 mmol) was dissolved in THF (75 mL) and shaken with 20% Pd/C (0.1 g) under an $H_2$ atmosphere (52 psi) for 30 minutes. The catalyst was removed by filtration through a pad of Celite, and the solution was concentrated to give 0.50 g (81%) of IIb as a white solid.

MS: 216 (M+1 for $C_{12}H_{25}N_1O_2$); TLC: $SiO_2$, $R_f$0.32 (10% MeOH/$CH_2Cl_2$).

Step 2: Example 6: [S-(R*,R*)]-4-Methyl-2-[methyl-(3-methyl-butyl)-amino]-pentanoic acid [2-(4-benzyloxy-phenyl)-1-tert-butylcarbamoyl-ethyl]-amide is made in accordance with the process of Example 1, except N-(3-methyl-butyl)-N-methyl-leucine (IIb) was used instead of N,N-dimethyl-L-leucine.

MS: 525 (M+1 for $C_{32}H_{49}N_3O_3$); sticky solid; TLC: $R_f$0.53 (10% MeOH/$CH_2Cl_2$).

Example 8

[S-(R*,R*)]-4-Methyl-2-[methyl-(3-methyl-butyl)-amino]-pentanoic acid [1-(4-benzyloxy-benzyl)-2-oxo-2-piperidin-1-yl-ethyl]-amide is made in accordance with the process of Example 1, except N-(3-methyl-butyl)-N-methyl-leucine (IIb) was used instead of N,N-dimethyl-L-leucine, and (S)-2-amino-3-(4-benzyloxy-phenyl)-N-(piperidin-1-yl)-propionamide (Ib) was used instead of (S)-2-amino-3-(4-benzyloxy-phenyl)-N-tert-butyl-propionamide.

MS: 537 (M+1 for $C_{33}H_{49}N_3O_3$); sticky solid; TLC: $R_f$0.53 (10% MeOH/$CH_2Cl_2$).

Example 9

[S-(R*,R*)]-4-Methyl-2-[methyl-(3-methyl-butyl)-amino]-pentanoic acid [2-(4-benzyloxy-phenyl)-1-(2-piperidin-1-yl-ethylcarbamoyl)-ethyl]-amide is made in accordance with the process of Example 1, except N-(3-methyl-butyl)-N-methyl-leucine (IIb) was used instead of N,N-dimethyl-L-leucine, and (S)-2-amino-3-(4-benzyloxy-phenyl)-N-(2-piperidin-1-yl-ethyl)-propionamide (Ic) was used instead of (S)-2-amino-3-(4-benzyloxy-phenyl)-N-tert-butyl-propionamide.

MS: 580 (M+1 for $C_{35}H_{54}N_4O_3$); sticky solid; TLC: $R_f$0.29 (10% MeOH/$CH_2Cl_2$).

Example 10

[S-(R*,R*)]4-Methyl-2-[methyl-(3-methyl-butyl)-amino]-pentanoic acid [1-(4-benzyloxy-benzyl)-2-(4-benzyl-piperazin-1-yl)-2-oxo-ethyl]-amide is made in accordance with the process of Example 1, except N-(3-methyl-butyl)-N-methyl-leucine (IIb) was used instead of N,N-dimethyl-L-leucine, and (S)-2-amino-3-(4-benzyloxy-phenyl)-1-(4-benzyl-piperazin-1-yl)-propan-1-one (Id) was used instead of (S)-2-amino-3-(4-benzyloxy-phenyl)-N-tert-butyl-propionamide.

MS: 628 (M+1 for $C_{39}H_{54}N_4O_3$); sticky solid; TLC: $R_f$0.52 (10% MeOH/$CH_2Cl_2$).

Example 11

[S-(R*,R*)]-4-Methyl-2-[methyl-(3-methyl-butyl)-amino]-pentanoic acid [2-(4-benzyloxy-phenyl)-1-(1-benzyl-piperidin-4-ylcarbamoyl)-ethyl]-amide is made in accordance with the process of Example 1, except N-(3-methyl-butyl)-N-methyl-leucine (IIb) was used instead of N,N-dimethyl-L-leucine, and (S)-2-amino-3-(4-benzyloxy-phenyl)-N-(1-benzyl-piperidin-4-yl)-propionamide (Ie) was used instead of (S)-2-amino-3-(4-benzyloxy-phenyl)-N-tert-butyl-propionamide.

MS: 642 (M+1 for $C_{40}H_{56}N_4O_3$); sticky solid; TLC: $R_f$0.45 (10% MeOH/$CH_2Cl_2$).

Example 12

[S-(R*,R*)]-4-Methyl-2-[methyl-(3-methyl-butyl)-amino]-pentanoic acid [1-(4-benzyloxy-benzyl)-2-(4-methylpiperazin-1-yl)-2-oxo-ethyl]-amide is made in accordance with the process of Example 1, except N-3-methylbutyl)-N-methyl-leucine (IIb) was used instead of N,N-dimethyl-L-leucine, and (S)-2-amino-3-(4-benzyloxyphenyl)-1-(4-methyl-piperazin-1-yl)-propan-1-one (If) was used instead of (S)-2-amino-3-(4-benzyloxy-phenyl)-N-tert-butyl-propionamide.

MS: 550 (M+1 for $C_{33}H_{50}N_4O_3$); sticky solid; TLC: $R_f$ 0.54 (10% MeOH/CH$_2$Cl$_2$).

Example 13

[S-(R*,R*)]-2-[(4-tert-Butyl-benzyl)-methyl-amino]-4-methyl-pentanoic acid [2-(4-benzyloxy-phenyl)-1-tert-butylcarbamoyl-ethyl]-amide Step 1: The preparation of (S)-2-(4-tert-butylbenzyl-methyl-amino)-4-methyl-pentanoic acid (IIc)

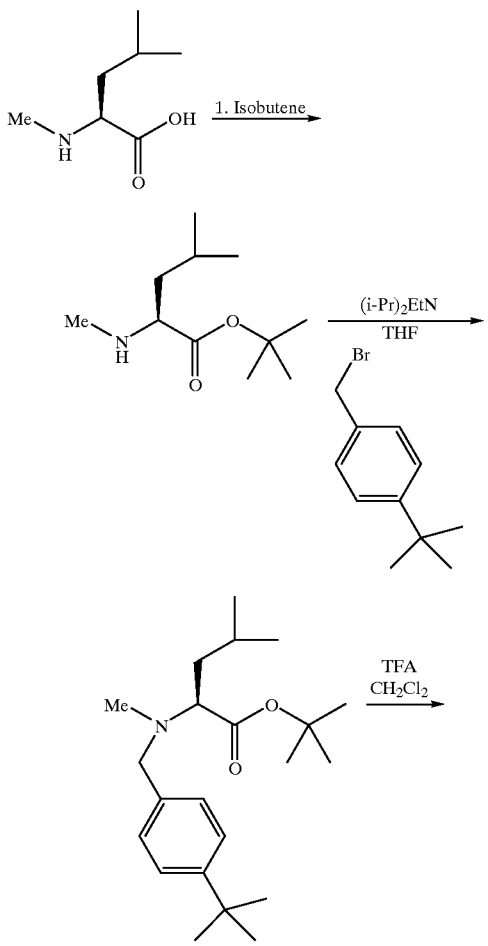

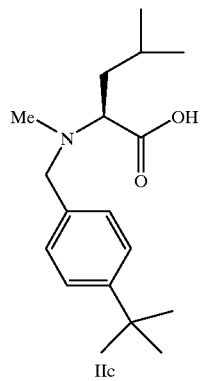

Step i: (S)-4-Methyl-2-methylamino-pentanoic acid (15 g, 103 mmol) was dissolved in dioxane (100 mL), cooled to 0° C., then treated with H$_2$SO$_4$ (10 mL) and isobutylene (100 mL). The mixture was stirred and allowed to come to room temperature over 1 hour. The reaction was vented and poured into a rapidly stirred mixture of KOH (20.7 g) in water, ice, and ether. The solution was filtered, and more ether was added. The organic layer was dried over Na$_2$SO$_4$ and concentrated to give 19.41 g (94%) of (S)4-methyl-2-methylamino-pentanoic acid tert-butyl ester.

MS: 202 (M+1 for $C_{11}H_{23}N_1O_2$); TLC SiO$_2$, $R_f$ 0.52 (10% MeOH/CH$_2$Cl$_2$).

Step ii: (S)-4-Methyl-2-methylamino-pentanoic acid tert-butyl ester (6 g, 29.8 mmol) was dissolved in THF (250 mL) and treated with diisopropylethylamine (7.8 mL, 44.7 mmol) and p-t-butyl-benzyl bromide (6.03 mL, 32.8 mL). The reaction was heated to 40° C. overnight, then filtered and concentrated. The residue was chromatographed on silica gel eluting with 5% EtOAc/hexanes to give 5.1 g (50%) of (S)-2-[(4-tert-Butyl-benzyl)-methyl-amino]-4-methyl-pentanoic acid tert-butyl ester.

MS: 349 (M+1 for $C_{32}H_{37}N_1O_2$); TLC SiO$_2$, $R_f$ 0.79 (25% EtOAc/hexanes).

Step, iii: (S)-2-[(4-tert-Butyl-benzyl)-methyl-amino]-4-methyl-pentanoic acid tert-butyl ester (0.5 g, 1.4 mmol) was dissolved in CH$_2$Cl$_2$ (10 mL) and treated with TFA (1mL). After 1 hour, 0.5 mL TFA was added, followed by another 1 mL TFA at 2.5 hours. The reaction was stirred overnight, then concentrated to give (S)-2-[(4-tert-butyl-benzyl)-methyl-amino]-4-methyl-pentanoic acid (IIc).

MS: 292 (M+1 for $C_{18}H_{27}N_1O_2$); mp: 110–112° C.; TLC SiO$_2$, $R_f$ 0.5 (12% MeOH/CH$_2$Cl$_2$).

Step 2: Example 11: [S-(R*,R*)]-2-[(4-tert-Butyl-benzyl)-methyl-amino]-4-methyl-pentanoic acid [2-(4-benzyloxy-phenyl)-1-tert-butylcarbamoyl-ethyl]-amide is made in accordance with the process of Example 1, except N-(4-tert-butylbenzyl)-N-methyl-leucine (IIc) was used instead of N,N-dimethyl-L-leucine.

MS: 601 (M+1 for $C_{38}H_{53}N_3O_3$); mp 98–99° C.; TLC: $R_f$ 0.70 (10% MeOH/CH$_2$Cl$_2$).

Example 14

[S-(R*,R*)]-2-[(4-tert-Butyl-benzyl)-methyl-amino]-4-methyl-pentanoic acid [2-(4-benzyloxy-phenyl)-1-(piperidine-1-carbonyl)-ethyl]-amide is made in accordance with the process of Example 1, except N-(4-tert-butylbenzyl)-N-methyl-leucine (IIc) was used instead of N,N-dimethyl-L-leucine, and (S)-2-amino-3-(4-benzyloxyphenyl)-N-(piperidin-1-yl)-propionamide (Ib) was used instead of (S)-2-amino-3-(4-benzyloxy-phenyl)-N-tert-butyl-propionamide.

MS: 613 (M+1 for $C_{39}H_{53}N_3O_3$); sticky solid; TLC: $R_f$ 0.60 (10% MeOH/$CH_2Cl_2$).

Example 15

[S-(R*,R*)]-2-[(4-tert-Butyl-benzyl)-methyl-amino]-4-methyl-pentanoic acid [2-(4-benzyloxy-phenyl)-1-(2-piperidin-1-yl-ethylcarbamoyl)-ethyl]-amide is made in accordance with the process of Example 1, except N-(4-tert-butylbenzyl)-N-methyl-leucine (IIc) was used instead of N,N-dimethyl-L-leucine, and (S)-2-amino-3-(4-benzyloxy-phenyl)-N-(2-piperidin-1-yl-ethyl)-propionamide (Ic) was used instead of (S)-2-amino-3-(4-benzyloxy-phenyl)-N-tert-butyl-propionamide.

MS: 656 (M+1 for $C_{41}H_{58}N_4O_3$); mp 95–96° C.; TLC: $R_f$ 0.17 (10% MeOH/$CH_2Cl_2$).

Example 16

[S-(R*,R*)-2-[(4-tert-Butyl-benzyl)-methyl-amino]-4-methyl-pentanoic acid [1-(4-benzyloxy-benzyl)-2-(4-benzyl-piperazin-1-yl)-2-oxo-ethyl]-amide is made in accordance with the process of Example 1, except N-(4-tert-butylbenzyl)-N-methyl-leucine (IIc) was used instead of N,N-dimethyl-L-leucine, and (S)-2-amino-3-(4-benzyloxy-phenyl)-1-(4-benzyl-piperazin-1-yl)-propan-1-one (Id) was used instead of (S)-2-amino-3-(4-benzyloxy-phenyl)-N-tert-butyl-propionamide.

MS: 704 (M+1 for $C_{45}H_{58}N_4O_3$); sticky solid; TLC: $R_f$ 0.57 (10% MeOH/$CH_2Cl_2$).

Example 17

S-(R*,R*)]-2-[(4-tert-Butyl-benzyl)-methyl-amino]-4-methyl-pentanoic acid [2-(4-benzyloxy-phenyl)-1-(1-benzyl-piperidin-4-yl-carbamoyl)-ethyl]-amide is made in accordance with the process of Example 1, except N-(4-tert-butylbenzyl)-N-methyl-leucine (IIc) was used instead of N,N-dimethyl-L-leucine, and (S)-2-amino-3-(4-benzyloxy-phenyl)-N-(1-benzyl-piperidin-4-yl)-propionamide (Ie) was used instead of (S)-2-amino-3-(4-benzyloxy-phenyl)-N-tert-butyl-propionamide.

MS: 718 (M+1 for $C_{46}H_{60}N_4O_3$); mp 93–95° C.; TLC: $R_f$ 0.43 (10% MeOH/$CH_2Cl_2$).

Example 18

[S-(R*,R*)]-2-[(4-tert-Butyl-benzyl)-methyl-amino]-4-methyl-pentanoic acid [1-(4-benzyloxy-benzyl)-2-(4-methyl-piperazin-1-yl)-2-oxo-ethyl]-amide is made in accordance with the process of Example 1, except N-(4-tert-butylbenzyl)-N-methyl-leucine (IIc) was used instead of N,N-dimethyl-L-leucine, and (S)-2-amino-3-(4-benzyloxy-phenyl)-1-(4-methyl-piperazin-1-yl)-propan-1-one (If) was used instead of (S)-2-amino-3-(4-benzyloxy-phenyl)-N-tert-butyl-propionamide.

MS: 615 (M+1 for $C_{38}H_{54}N_4O_3$); sticky solid; TLC: $R_f$ 0.58 (10% MeOH$CH_2Cl_2$).

Example 19

[S-(R*,R*)]-2-(Cyclohexyl-methyl-amino)-4-methyl-pentanoic acid [2-(4-benzyloxy-phenyl)-1-tert-butylcarbamoyl-ethyl]-amide Step 1: The Preparation (S)-2-(Cyclohexyl-methyl-amino)-4-methyl-pentanoic Acid (IId)

Scheme X

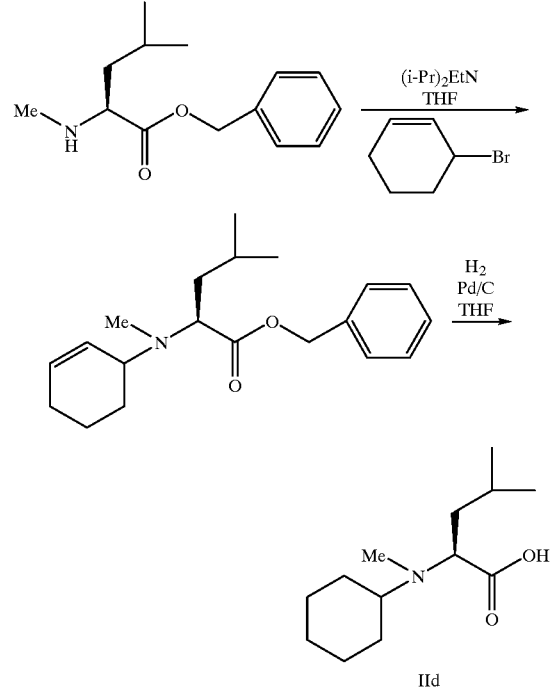

Step i: N-Me-O-Benzyl-L-Leucine (3.6 g, 15.3 mmol) was dissolved in THF (77 mL) and treated with diisopropyl-ethylamine (21 mL, 122 mmol) and 3-bromo-cyclohexene (3.5 mL, 30.6 mmol). The reaction was heated to 50° C. for 2 days. The reaction was filtered, and the solution was concentrated. The residue was chromatographed on silica gel eluting with 8% ethyl acetate/hexanes to give 2.75 g (57%) of (S)-2-(cyclohexenyl-methyl-amino)-4-methyl-pentanoic acid benzyl ester.

MS: 317 (M+1 for $C_{20}H_{29}N_1O_2$); TLC: $SiO_2$, $R_f$ 0.86 (10% MeOH/$CH_2Cl_2$).

Step ii: (S)-2-(Cyclohexenyl-methyl-amino)-4-methyl-pentanoic acid benzyl ester (2.87 g, 9.10 mmol) was dissolved in THF (50 mL) and shaken with 20% Pd/C (0.2 g) under an $H_2$ atmosphere for 4 hours. The catalyst was removed by filtration through a pad of Celite, and the solution was concentrated to give 1.44 g (70%/0) of IId as a white solid.

MS: 228 (M+1 for $C_{13}H_{25}N_1O_2$); TLC: $SiO_2$, $R_f$ 0.27 (10% MeOH/$CH_2Cl_2$).

Step 2: Example 19: [S-(R*,R*)]-2-(Cyclohexyl-methyl-amino)-4-methyl-pentanoic acid [2-(4-benzyloxy-phenyl)-1-tert-butylcarbamoyl-ethyl]-amide is made in accordance with the process of Example 1, except N-cyclohexyl-N-methyl-leucine (IId) was used instead of N,N-dimethyl-L-leucine.

MS: 537 (M+1 for $C_{33}H_{49}N_3O_3$); sticky solid; TLC: $R_f$ 0.57 (10% MeOH/$CH_2Cl_2$).

Example 20

[S-(R*,R*)]-2-(Cyclohexyl-methyl-amino)-4-methyl-pentanoic acid [2-(4-benzyloxy-phenyl)-1-(piperidine-1-carbonyl)-ethyl]-amide is made in accordance with the process of Example 1, except N-cyclohexyl-N-methyl-leucine (IId) was used instead of N,N-dimethyl-L-leucine, and (S)-2-amino-3-(4-benzyloxy-phenyl)-N-(piperidin-1-yl)-propionamide (Ib) was used instead of (S)-2-amino-3-(4-benzyloxy-phenyl)-N-tert-butyl-propionamide.

MS: 549 (M+1 for $C_{34}H_{49}N_3O_3$); sticky solid; TLC: $R_f$ 0.52 (10% MeOH/$CH_2Cl_2$).

Example 21

[S-(R*,R*)]-2-(Cyclohexyl-methyl-amino)4-methyl-pentanoic acid [2-(4-benzyloxy-phenyl)-1-(2-piperidin-1-yl-ethylcarbamoyl)-ethyl]-amide is made in accordance with the process of Example 1, except N-cyclohexyl-N-methyl-leucine (IId) was used instead of N,N-dimethyl-L-leucine, and (S)-2-amino-3-(4-benzyloxy-phenyl)-N-(2-piperidin-1-yl-ethyl)-propionamide (Ic) was used instead of (S)-2-amino-3-(4-benzyloxy-phenyl)-N-tert-butyl-propionamide.

MS: 592 (M+1 for $C_{36}H_{54}N_4O_3$); sticky solid; TLC: $R_f$ 0.29 (10% MeOH/$CH_2Cl_2$).

Example 22

[S-(R*,R*)]-2-(Cyclohexyl-methyl-amino)-4-methyl-pentanoic acid [1-(4-benzyloxy-benzyl)-2-(4-benzyl-piperazin-1-yl)-2-oxo-ethyl]-amide is made in accordance with the process of Example 1, except N-cyclohexyl-N-methyl-leucine (IId) was used instead of N,N-dimethyl-L-leucine, and (S)-2-amino-3-(4-benzyloxy-phenyl)-1-(4-benzyl-piperazin-1-yl)-propan-1-one (Id) was used instead of (S)-2-amino-3-(4-benzyloxy-phenyl)-N-tert-butyl-propionamide.

MS: 640 (M+1 for $C_{40}H_{54}N_4O_3$); sticky solid; TLC: $R_f$ 0.53 (10% MeOH/$CH_2Cl_2$).

Example 23

[S-(R*,R*)]-2-(Cyclohexyl-methyl-amino)-4-methyl-pentanoic acid [2-(4-benzyloxy-phenyl)-1-(1-benzyl-piperidin-4-ylcarbamoyl)-ethyl]-amide is made in accordance with the process of Example 1, except N-cyclohexyl-N-methyl-leucine (IId) was used instead of N,N-dimethyl-L-leucine, and (S)-2-amino-3-(4-benzyloxy-phenyl)-N-(1-benzyl-piperidin-4-yl)-propionamide (Ie) was used instead of (S)-2-amino-3-(4-benzyloxy-phenyl)-N-tert-butyl-propionamide.

MS: 654 (M+1 for $C_{41}H_{56}N_4O_3$); sticky solid; TLC: $R_f$ 0.49 (10% MeOH/$CH_2Cl_2$)

Example 24

[S-(R*,R*)]-2-(Cyclohexyl-methyl-amino)4-methyl-pentanoic acid [1-(4-benzyloxy-benzyl)-2-(4-methyl-piperazin-1-yl)-2-oxo-ethyl]-amide is made in accordance with the process of Example 1, except N-cyclohexyl-N-methyl-leucine (IId) was used instead of N,N-dimethyl-L-leucine, and (S)-2-amino-3-(4-benzyloxy-phenyl)-1-(4-methyl-piperazin-1-yl)-propan-1-one (If) was used instead of (S)2-amino-3-(4-benzyloxy-phenyl)-N-tert-butyl-propionamide.

MS: 563 (M+1 for $C_{34}H_{50}N_4O_3$); sticky solid; TLC: $R_f$ 0.53 (10% MeOH/$CH_2Cl_2$).

Example 25

[S-(R*,R*)]-2-(Cyclohexylmethyl-methyl-amino)-4-methyl-pentanoic acid [2-(4-benzyloxy-phenyl)-1-tert-butylcarbamoyl-ethyl]-amide Step 1: The preparation of (S)-2-(Cyclohexylmethyl-methyl-amino)-4-methyl-pentanoic acid (IIe): IIe is made in accordance with the process of IIb, except cyclohexanecarboxaldehyde was used instead of isovaleraldehyde.

Step 2: Example 25: [S-(R*,R*)]-2-(Cyclohexylmethyl-methyl-amino)-4-methyl-pentanoic acid [2-(4-benzyloxy-phenyl)-1-tert-butylcarbamoyl-ethyl]-amide is made in accordance with the process of Example 1, except (S)-2-(cyclohexylmethyl-methyl-amino)4-methyl-pentanoic acid (IIe) was used instead of N,N-dimethyl-L-leucine.

MS: 550 (M+1 for $C_{34}H_{51}N_3O_3$); sticky solid; TLC: $R_f$ 0.50 (10% MeOH/$CH_2Cl_2$).

Example 26

[S-(R*,R*)]-2-(Cyclohexylmethyl-methyl-amino)-4-methyl-pentanoic acid [$^2$-($^4$-benzyloxy-phenyl)-1-(piperidine-1-carbonyl)-ethyl]-amide is made in accordance with the process of Example 1, except (S)-2-(cyclohexylmethyl-methyl-amino)-4-methyl-pentanoic acid (IIe) was used instead of N,N-dimethyl-L-leucine, and (S)-2-amino-3-(4-benzyloxy-phenyl)-N-(piperidin-1-yl)-propionamide (Ib) was used instead of (S)-2-amino-3-(4-benzyloxy-phenyl)-N-tert-butyl-propionamide.

MS: 562 (M+1 for $C_{35}H_{51}N_3O_3$); sticky solid; TLC: $R_f$ 0.46 (10% MeOH/$CH_2Cl_2$).

Example 27

[S-(R*,R*)]-2-(Cyclohexylmethyl-methyl-amino)-4-methyl-pentanoic acid [2-(4-benzyloxy-phenyl)-1-(2-piperidin-1-yl-ethylcarbamoyl)-ethyl]-amide is made in accordance with the process of Example 1, except (S)-2-(cyclohexylmethyl-methyl-amino)-4-methyl-pentanoic acid (IIe) was used instead of N,N-dimethyl-L-leucine, and (S)-2-amino-3-(4-benzyloxy-phenyl)-N-(2-piperidin-1-yl-ethyl)-propionamide (Ic) was used instead of (S)-2-amino-3-(4-benzyloxy-phenyl)-N-tert-butyl-propionamide.

MS: 605 (M+1 for $C_{37}H_{56}N_4O_3$); sticky solid; TLC: $R_f$ 0.23 (10% MeOH/$CH_2Cl_2$).

Example 28

[S-(R*,R*)]-2-(Cyclohexylmethyl-methyl-amino)-4-methyl-pentanoic acid [1-(4-benzyloxy-benzyl)-2-(4-benzyl-piperazin-1-yl)-2-oxo-ethyl]-amide is made in accordance with the process of Example 1, except (S)-2-(cyclohexylmethyl-methyl-amino)-4-methyl-pentanoic acid (IIe) was used instead of N,N-dimethyl-L-leucine, and (S)-2-amino-3-(4-benzyloxy-phenyl)-1-(4-benzyl-piperazin-1-yl)-propan-1-one (Id) was used instead of (S)-2-amino-3-(4-benzyloxy-phenyl)-N-tert-butyl-propionamide.

MS: 653 (M+1 for $C_{41}H_{56}N_4O_3$); sticky solid; TLC: $R_f$ 0.49 (10% MeOH/$CH_2Cl_2$).

Example 29

[S-(R*,R*)]-2-(Cyclohexylmethyl-methyl-amino)-4-methyl-pentanoic acid [2-(4-benzyloxy-phenyl)-1-(1-benzyl-piperidin-4-ylcarbamoyl)-ethyl]-amide is made in accordance with the process of Example 1, except (S)-2-(cyclohexylmethyl-methyl-amino)-4-methyl-pentanoic acid (IIe) was used instead of N,N-dimethyl-L-leucine, and (S)-2-amino-3-(4-benzyloxy-phenyl)-N-(1-benzyl-piperidin-4-yl)-propionamide (Ie) was used instead of (S)-2-amino-3-(4-benzyloxy-phenyl)-N-tert-butyl-propionamide.

MS: 665 (M+1 for $C_{42}H_{56}N_4O_3$); sticky solid; TLC: $R_f$ 0.34 (10% MeOH/$CH_2Cl_2$).

Example 30

[S-(R*,R*)]-2-(Cyclohexylmethyl-methyl-amino)-4-methyl-pentanoic acid [1-(4-benzyloxy-benzyl)-2-(4- methyl-piperazin-1-yl)-2-oxo-ethyl]-amide is made in accordance with the process of Example 1, except (S)-2-(cyclohexylmethyl-methyl-amino)-4-methyl-pentanoic acid (IIe) was used instead of N,N-dimethyl-L-leucine, and (S)-2-amino-3-(4-benzyloxy-phenyl)-1-(4-methyl-piperazin-1-yl)-propan-1-one (If) was used instead of (S)-2-amino-3-(4-benzyloxy-phenyl)-N-tert-butyl-propionamide.

MS: 553 (M+1 for $C_{33}H_{52}N_4O_3$); sticky solid; TLC: $R_f$ 0.54 (10% MeOH/CH$_2$Cl$_2$).

General Procedure for the Preparation of Substituted Peptidylamines (IV)

Scheme XI

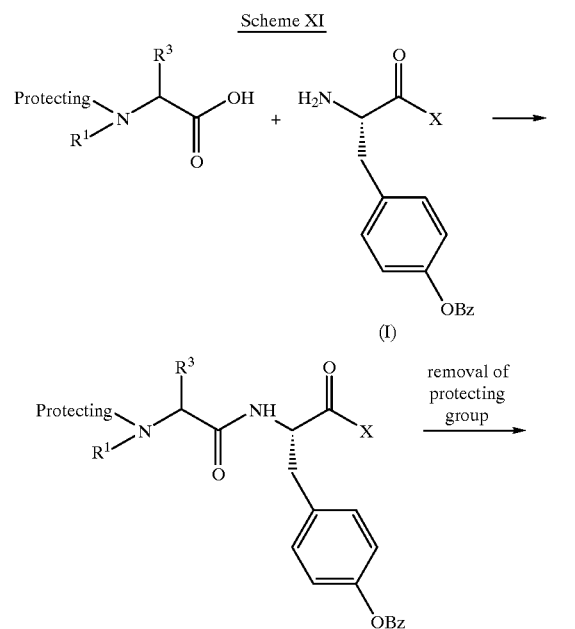

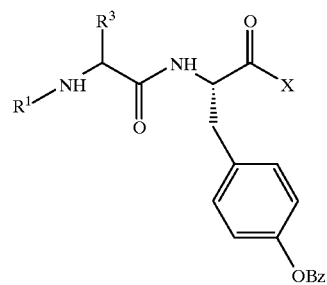

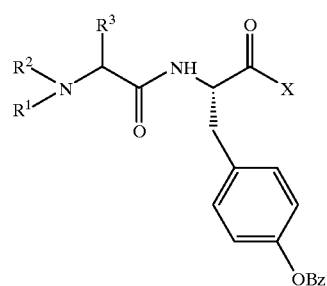

Example 31

[S-(R*,R*)]-3-(4-Benzyloxy-phenyl)-2-[4-methyl-2-(3-methyl-but-2-enylamino)-pentanoylamino]-propionic acid tert-butyl ester Scheme XII

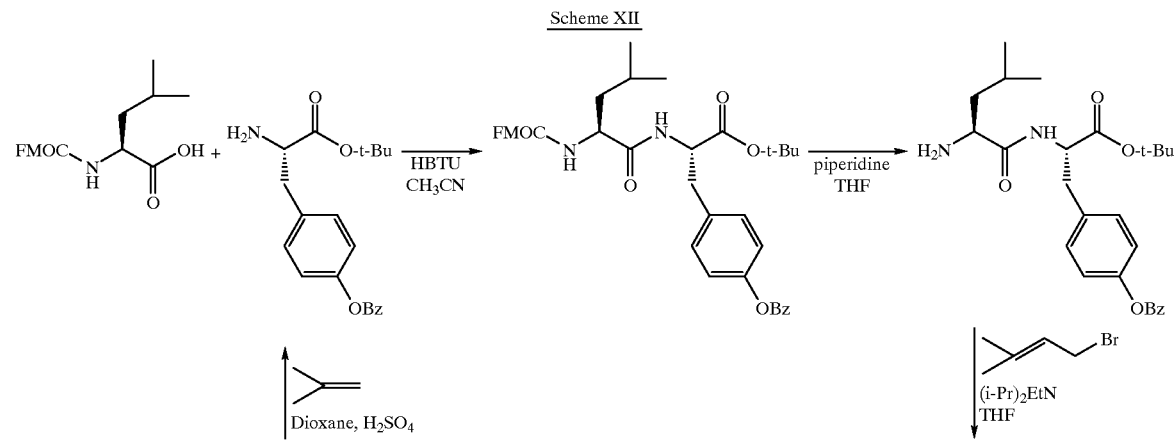

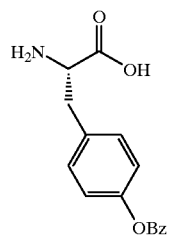

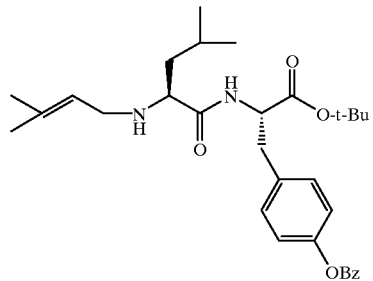

Example 31

Step 1: The Preparation of (S)-2-Amino-3-(4-benzyloxy-phenyl)-propionic acid tert-butyl ester A solution of L-tyrosine-OBn (50.0 g, 0.184 mol) was dissolved in dioxane (500 mL). The reaction vessel was charged with isobutylene (500 mL) and concentrated sulfuric acid (50 mL). The reaction vessel was sealed and shaken for 64 hours. The reaction mixture was vented and poured into a rapidly stirring mixture of KOH (104 g) in ice water 1000 mL. The resulting mixture was extracted into ether (5×200 mL), and the combined organic extracts were dried (MgSO$_4$), filtered, and concentrated. The residue was purified by chromatography (silica gel, 2:1 CHCl$_3$/EtOAc). The residue obtained from the chromatography solidified on standing to give the product as a tan solid (35.3 g, 59%).

Step 2: The Preparation of 3-(4-Benzyloxy-phenyl)-2-{2-1 (9H-fluoren-9-ylmethyl)-amino]-4-methyl-pentanoylamino}propionic acid tert-butyl ester A solution of FMOC-leucine (10.3 g, 29 mmol) in 300 mL of DMP was cooled to 0° C. and treated with diisopropylethyl amine (73 mL) and HBTU (11.1 g, 29.2 mmol). The resulting solution was stirred at 0° C. for 30 minutes and treated with (S)-amino-3-(4-benzyloxy-phenyl) propionic acid tert-butyl ester (110 g, 36.9 mmol). The resulting solution was stirred for 30 minutes at 0° C. and warmed to room temperature. The reaction mixture was poured into 500 mL of ether and washed sequentially with 1N aqueous HCl, saturated aqueous NaHCO$_3$ (100 mL), and brine (5×100 mL). The organic phase was collected, dried MgSO$_4$ and concentrated to near dryness. The residue was triturated with hexane. The product was collected by suction filtration and air dried to give the title compound as a white solid (12.16 g, 70%) mp 158–160° C.

Analysis Calculated for C$_{41}$H$_{46}$N$_2$O$_6$: C, 74.30; H, 7.00; N, 4.23. Found: C, 74.21; H, 7.25; N, 4.20.

Step 3: The Preparation of 2-{2-Amino-4-methyl-pentanoylamino}-3-(4-benzyloxy-phenyl)-propionic acid tert-butyl ester A solution of 3-(4-benzyloxy-phenyl)-2-{2-[(9H-fluoren-9-ylmethyl)-amino]-4-methyl pentanoylamino}-propionic acid tert-butyl ester (12.2 g, 20.0 mmol) in 500 mL of tetrahydrofuran was treated with piperidine (80 mL). The resulting solution was stirred at room temperature for 48 hours. The reaction mixture was concentrated and the residue purified by chromatography (SiO$_2$, gradient elution EtOAc - 15% EtOH/EtOAc). The resulting yellow solid was broken up in heptane to give the title compound as a white solid (6.77 g, 77%).

Step 4: Example 31: [S-(R*,R*)]-3-(4-Benzyloxy-ph enyl)-2-[4-methyl-2-(3-methyl-but-2-enylamino)-pentanoylamino]-propionic acid tert-butyl ester A mixture of 2-{2-amino-4-methyl-pentanoylamino}-3-(4-benzyloxy-phenyl)-propionic acid tert-butyl ester (2 nmmol), diisopropyl ethylamine (3 mmol), 1-bromo-3-methyl-2-butene (3 mmol) and anhydrous THF (30 mL) was stirred at 25° C. for 6 hours. The precipitate was filtered off. The reaction mixture was concentrated and purified by column chromatography on silica gel eluting with 25% EtOAc/hexanes to give the titled compound (600 mg, 60% yield)

MS: 510 (M+1 for C$_{31}$H$_{44}$N$_2$O$_4$); mp 70–71 ° C.; TLC: R$_f$0.3 (25% EtOAc/hexanes).

Example 32

[S-(R*,R*)]-3-(4-Benzyloxy-phenyl)-2-[2-(4-tert-butyl-benzylamino)-4-methyl-pentanoylamino]-propionic acid tert-butyl ester is made in accordance with the process of Example 31, except 4-tertbutylbenzylbromide was used instead of 1-bromo-3-methyl-2-butene.

MS: 588 (M+1 for C$_{37}$H$_{50}$N$_2$O$_4$); mp 89–90° C.; TLC: R$_f$0.3 (20% EtOAc/hexanes).

Example 33

[S-(R*,R*)]-2-(2-Benzylamino-4-methyl-pentanoylamino)-3-(4-benzyloxy-phenyl)-propionic acid tert-butyl ester is made in accordance with the process of Example 47, except benzylbromide was used instead of 1 -bromo-3-methyl-2-butene.

MS: 532 (M+1 for C$_{33}$H$_{42}$N$_2$O$_4$); mp 66–67° C.; TLC: R$_f$0.7 (33% EtOAc/hexanes).

Example 34

[S-(R*,R*)]-4-Methyl-2-[methyl-(3-methyl-butyl)-amino]-pentanoic acid [2-(4-benzyloxy-phenyl)-1-tert-butylcarbamoyl-ethyl]-amide

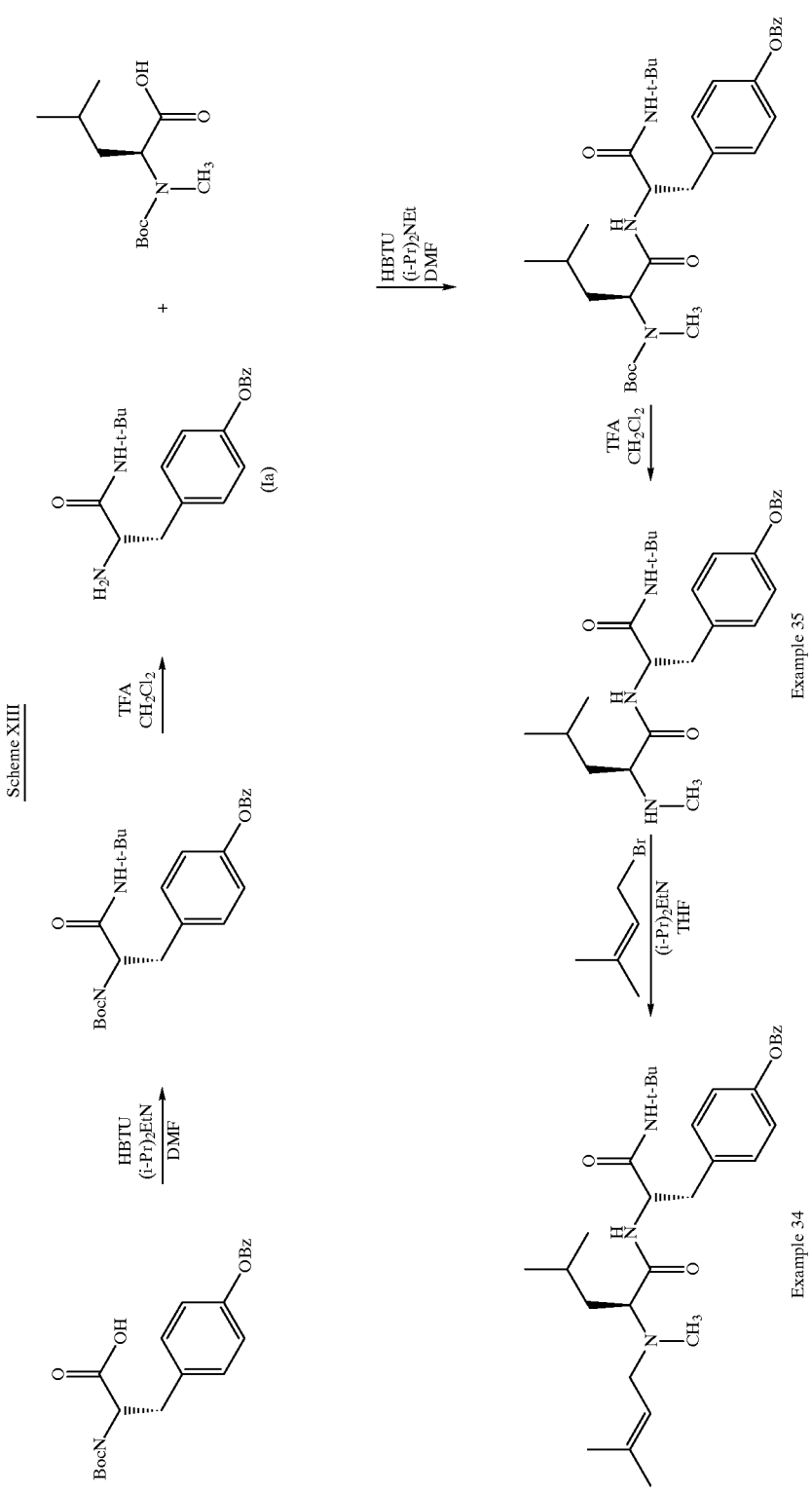

Step 1: Example 35: [S-(R*,R*)]-4-Methyl-2-methylamino-pentanoic acid [2-(4-benzyloxy-phenyl)-1-tert-butylcarbamoyl-ethyl]-amide Step i: (S)-2-Amino-3-(4-benzyloxy-phenyl)-N-tert-butyl-propionamide (7.0 g, 21.4 mmol) (Ia) was dissolved in $CH_3CN$ (75 mL) and treated with diisopropylethylamine (3.72 mL, 21.4 mmol), N-Boc-N-Me-L-leucine (3.51 g, 14.3 mmol), and HBTU (5.42 g, 14.3 mmol). The reaction was stirred for 30 minutes and then concentrated. The residue was dissolved in EtOAc (300 mL), washed with saturated bicarbonate solution (2×300 mL) and brine (300 mL), dried over $Na_2SO_4$, and concentrated. The crude material was chromatographed on silica gel eluting with 25% EtOAc/hexanes to give 7.0 g (88%) of {1-[2-(4-benzyloxy-phenyl)-1-tert-butylcarbamoyl-ethylcarbamoyl]-3-methyl-butyl}-methyl-carbamic acid tert-butyl ester.

MS: 554 (M+1 for $C_{32}H_{46}N_3O_5$); TLC: $SiO_2$, $R_f$0.26 (8% MeOH/$C_2Cl_2$).

Step ii: Example 35: [S-(R*,R*)]-4-Methyl-2-methylamino-pentanoic acid [2-(4-benzyloxy-phenyl)-1-tert-butylcarbamoyl-ethyl]-amide {1-[2-(4-Benzyloxy-phenyl)- 1-tert-butylcarbamoyl-ethylcarbamoyl]-3-methyl-butyl}-methyl-carbamic acid tert-butyl ester (4.0 g, 7.24 mmol) was dissolved in $CH_2Cl_2$ (24 mL) and treated with trifluoroacetic acid (16 mL). The reaction was stirred for 15 minutes, then concentrated, diluted with EtOAc (300 mL), washed with bicarbonate solution (3×300 mL) and brine (300 mL), dried over $Na_2SO_4$, and concentrated. The crude material was chromatographed on silica gel eluting with 8% MeOH/$CH_2Cl_2$ to give 2.8 g (85%) of Example 35. The hydrochloride salt of Example 34 was prepared by dissolving the free base in $Et_2O$, adding 1 M HCl in $Et_2O$, and concentrating the solution in vacuo.

MS: 454 (M+1 for $C_{27}H_{38}N_3O_3$); TLC: $SiO_2$, $R_f$0.19 (8% MeOH/$CH_2Cl_2$).

Step 2: Example 34: [S-(R*,R*)]-4-Methyl-2-[methyl-(3-methyl-butyl)-amino]-pentanoic acid [2-(4-benzyloxy-phenyl)-1-tert-butylcarbamoyl-ethyl]-amide The HCl salt of Example 35 (0.5 g, 1.0 mmol) was dissolved in $CH_2Cl_2$ (5 mL) and treated with isovaleraldehyde (0.11 mL, 1.0 mmol). The reaction was stirred for 30 minutes, then cooled to 0° C. and treated with sodium triacetoxyborohydride (0.32 g, 1.5 mmol). The reaction was allowed to warm to room temperature and stir overnight. The reaction was diluted with $CH_2Cl_2$ (100 mL), washed with saturated bicarbonate solution (2×100 mL) and brine (100 mL), dried over $Na_2SO_4$, and concentrated. The residue was chromatographed on silica gel eluting with 8% acetone/$CH_2Cl_2$ to give 0.27 g (52%) of the title compound.

MS: 525 (M+1 for $C_{32}H_{49}N_3O_3$); sticky solid; TLC: $SiO_2$, $R_f$0.53 (10% MeOH/$CH_2Cl_2$).

Example 36

[S-(R*,R*)]-2-[(3,3-Dimethyl-butyl)-methyl-amino]-4-methyl-pentanoic acid [2-(4-benzyloxy-phenyl)-1-tert-butylcarbamoyl-ethyl]-amide is made in accordance with the process of Example 34, except 3,3-dimethylbutyraldehyde was used instead of isovaleraldehyde.

MS: 539 (M+1 for $C_{33}H_{51}N_3O_3$); sticky solid; TLC: $R_f$0.55 (50% hexanes/EtOAc).

Example 37

[S-(R*,R*/S*)]-2-Diethylamino-4-methyl-pentanoic acid[2-(4-benzyloxy-phenyl)-1-tert-butylcarbamoyl-ethyl]-amide is made in accordance with the process of Example 34, except acetaldehyde was used instead of isovaleraldehyde and N-Boc-N-Methyl-(D,L)-Leucine was used instead of N-Boc-N-methyl-L-leucine for the intermediates preparation.

MS: 501 (M+1 for $C_{30}H_{45}N_3O_3$); sticky solid; TLC: $R_f$0.4 (50% hexanes/EtOAc).

Example 38

[S-(R*,R*)]-2-[(4-tert-Butyl-cyclohexyl)-methyl-amino]-4-methyl-pentanoic acid [2-(4-benzyloxy-phenyl)-1-tert-butylcarbamoyl-ethyl]-amide is made in accordance with the process of Example 34, except 4-tert-butyl-cyclohexanone was used instead of isovaleraldehyde.

MS: 473 (M+1 for $C_{27}H_{57}N_3O_3$); sticky solid; TLC: $R_f$0.7 (66% hexanes/EtOAc).

Example 39

[S-(R*,R*)]-4-Methyl-2-[methyl-(4-methyl-cyclohexyl)-amino]-pentanoic acid [2-(4-benzyloxy-phenyl)-1-tert-butylcarbamoyl-ethyl]-amide is made in accordance with the process of Example 34, except 4-methyl-cyclohexanone was used instead of isovaleraldehyde.

MS: 550 (M+1 for $C_{34}H_{51}N_3O_3$); sticky solid; TLC: $R_f$0.4 (66% hexanes/EtOAc).

Example 40

[S-(R*,R*)]-2-[(4-Dimethylamino-benzyl)-methyl-amino]-4-methyl-pentanoic acid [2-(4-benzyloxy-phenyl)-1-tert-butylcarbamoyl-ethyl]-amide is made in accordance with the process of Example 34, except 4-(dimethylamino)-benzaldehyde was used instead of isovaleraldehyde.

MS: 588 (M+1 for $C_{36}H_{50}N_4O_3$); sticky solid; TLC: $R_f$0.2 (66% hexanes/EtOAc).

Example 41

[S-(R*,R*)]-2-(Butyl-methyl-amino)-4-methyl-pentanoic acid [2-(4-benzyloxy-phenyl)-1-tert-butylcarbamoyl-ethyl]-amide is made in accordance with the process of Example 34, except n-butyraldehyde was used instead of isovaleraldehyde.

MS: 511 (M+1 for $C_{31}H_{47}N_3O_3$); sticky solid; TLC: $R_f$0.5 (50% hexanes/EtOAc).

Example 42

[S-(R*,R*)]-2-(Isobutyl-methyl-amino)-4-methyl-pentanoic acid [2-(4-benzyloxy-phenyl)-1-tert-butylcarbamoyl-ethyl]-amide is made in accordance with the process of Example 34, except iso-butyraldehyde was used instead of isovaleraldehyde.

MS: 515 (M+1 for $C_{31}H_{47}N_3O_3$); mp 75–76° C.; TLC: $R_f$0.8 (50% hexanes/EtOAc).

Example 43

[S-(R*,R*)]-4-Methyl-2-methylamino-pentanoic acid [1-(4-benzyloxy-benzyl)-2-(4-benzyl-piperazin-1-yl)-2-oxo-ethyl]-amide is made in accordance with the process of Example 35, except (S)-2-amino-3-(4-benzyloxy-phenyl)-1-(4-benzyl-piperazin-1-yl)-propan- 1-one (Id) was used instead of (S)-2-amino-3-(4-benzyloxy-phenyl)-N-tert-butyl-propionamide.

MS: 558 (M+1 for $C_{34}H_{44}N_4O_3$); sticky solid; TLC: $R_f$0.6 (10% MeOH/$CH_2Cl_2$).

Example 44

[S-(R*,R*)]-3-Methyl-2-[methyl-(3-methyl-butyl)-amino]-pentanoic acid [2-(4-benzyloxy-phenyl)-1-tertbutylcarbamoyl-ethyl]-amide is made in accordance with the process of Example 34, except N-Boc-N-methyl-isoleucine was used instead of except N-Boc-N-methyl-leucine.

MS: 524 (M+1 for $C_{32}H_{49}N_3O_3$); sticky solid; TLC: $R_f$ 0.63 (10% MeOH/$CH_2Cl_2$).

Example 45

[S-(R*,R*)]-4Methyl-2-[ethyl-(3-methyl-butyl)-amino]-pentanoic acid [2-(4-benzyloxy-phenyl)-1-tert-butylcarbamoyl-ethyl]-amide is made in accordance with the process of Example 34, except N-Boc-N-ethyl-leucine was used instead of N-Boc-N-methyl-leucine.

MS: 538 (M+1 for $C_{33}H_{51}N_3O_3$); sticky solid; TLC: $R_f$ 0.71 (10% MeOH/$CH_2Cl_2$).

Example 46

[S-(R*,R*)]-4-Methyl-2-[methyl-(3-methyl-butyl)-amino]-butyric acid [2-(4-benzyloxy-phenyl)-1-tert-butylcarbamoyl-ethyl]-amide is made in accordance with the process of Example 34, except N-Boc-N-methyl-valine was used instead of N-Boc-N-methyl-leucine.

MS: 510 (M+1 for $C_{31}H_{47}N_3O_3$); sticky solid; TLC: $R_f$ 0.59 (10% MeOH/$CH_2Cl_2$).

Example 47

[S-(R*,R*)]-2-(Cyclohex-2-enyl-methyl-amino)-4-methyl-pentanoic acid [2-(4-benzyloxy-phenyl)-1-tert-butylcarbamoyl-ethyl]-amide 4-Methyl-2-methylamino-pentanoic acid [2-(4-benzyloxy-phenyl)-1-tert-butylcarbamoyl-ethyl]-amide (Example 35) (1.0 mmol) was dissolved in THF (10 mL) and treated with 3-bromocyclohexene (1.5 mmol) and diisopropylethylamine (3 mmol). The reaction was stirred at 50° C. for 18 hours. Then the reaction mixture was allowed to cool to room temperature and concentrated to dryness. The residue was chromatographed on silica gel eluting with a gradient of 10–30% acetone/$CH_2Cl_2$ to give the title compound with the yields of 50%.

MS: 535 (M+1 for $C_{33}H_{47}N_3O_3$); sticky solid; TLC: $R_f$ 0.5 (50% hexanes/EtOAc).

Example 48

[S-(R*,R*)]-2-[(4-tert-Butyl-benzyl)-methyl-amino]-4-methyl-pentanoic acid [2-(4-benzyloxy-phenyl)-1-tert-butylcarbamoyl-ethyl]-amide 2-(Methyl-amino)-4-methyl-pentanoic acid [2-(4-benzyloxy-phenyl)-1-tert-butylcarbamoyl-ethyl]-amide (0.5 mmol) was dissolved in THF (10 mL) and treated with 4-tert-butyl-benzyl bromide (0.75 mmol) and diisopropylethylamine (1.5 mmol). The reaction was stirred at 50° C. for 15 hours. Then the reaction mixture was allowed to cool to room temperature and concentrated to dryness. The residue was chromatographed on silica gel eluting with a gradient of 25% EtOAc/Hexanes to give the title compound with the yield of 40%.

MS: 601 (M+1 for $C_{38}H_{53}N_3O_3$); mp 98–99° C.; TLC: $R_f$ 0.70 (10% MeOH/$CH_2Cl_2$).

Example 49

[S-(R*,R*)]-2-(Cyclohex-2-enylamino)-4-methyl-pentanoic acid [2-(4-benzyloxy-phenyl)-1-tert-butylcarbamoyl-ethyl]-amide Step 1: The preparation of 4-Methyl-2-amino-pentanoic acid [2-(4-benzyloxy-phenyl)-1-tert-butylcarbamoyl-ethyl]-amide (Va) is made in accordance with the process of Example 35, except N-Boc-leucine was used instead of N-Boc-N-methyl-leucine.

Step 2: Example 49: [S-(R*,R*)]-2-(Cyclohex-2-enylamino)-4-methyl-pentanoic acid [2-(4-benzyloxy-phenyl)-1-tert-butylcarbamoyl-ethyl]-amide is made in accordance with the process of Example 47, except 4-methyl-2-amino-pentanoic acid [2-(4-benzyloxy-phenyl)-1-tert-butylcarbamoyl-ethyl]-amide (Va) was used instead of 4-methyl-2-methylamino-pentanoic acid [2-(4-benzyloxy-phenyl)-1-tert-butylcarbamoyl-ethyl]-amide.

MS: 521 (M+1 for $C_{32}H_{45}N_3O_3$); sticky solid; TLC: $R_f$ 0.7 (50% hexanes/EtOAc).

Example 50

[S-(R*,R*)]-2-(4-tert-Butyl-benzylamino)-4-methyl-pentanoic acid [2-(4-benzyloxy-phenyl)-1-tert-butylcarbamoyl-ethyl]-amide is made in accordance with the process of Example 47 except 4-methyl-2-amino-pentanoic acid [2-(4-benzyloxy-phenyl)-1-tert-butylcarbamoyl-ethyl]-amide (Va) was used instead of 4-methyl-2-methylamino-pentanoic acid [2-(4-benzyloxy-phenyl)-1-tert-butylcarbamoyl-ethyl]-amide, and 4-tertbutylbenzylbromide was used instead of 3-bromocyclohexene.

MS: 586 (M+1 for $C_{37}H_{51}N_3O_3$); TLC: $R_f$ 0.8 (50% hexanes/EtOAc).

Example 51

[S-(R*,R*)]4-Methyl-2-[methyl-(3-methyl-but-2-enyl)-amino]-pentanoic acid [2-(4-benzyloxy-phenyl)-1-tert-butylcarbamoyl-ethyl]-amide is made in accordance with the process of Example 47 except 4-bromo-2-methyl-2-butene was used instead of 3-bromocyclohexene.

MS: 523 (M+1 for $C_{32}H_{47}N_3O_3$); mp 91–92° C.; TLC: $R_f$ 0.4 (EtOAc).

Example 52

[S-(R*,R*)]-2-(4-tert-Butyl-benzylamino)-4-methyl-pentanoic acid [1-(4-benzyloxy-benzyl)-2-(4-benzyl-piperazin-1-yl)-2-oxo-ethyl]-amide Step 1: The preparation of (S)-2-Amino-3-(4-benzyloxy-phenyl)-1-(4-benzyl-piperazin-1-yl)-propan-1-one (Id) (described in Example 4)

Step 2: The preparation of [S-(R*,R*)]-2-Amino-4-methyl-pentanoic acid [1-(4-benzyloxy-benzyl)-2-(4-benzyl-piperazin-1-yl)-2-oxo-ethyl]-amide (Vb) is made in accordance with the process of Example 35, except (S)-2-amino-3-(4-benzyloxy-phenyl)-1-(4-benzyl-piperazin-1-yl)-propan-1-one (Id) was used instead of (S)-2-amino-3-(4-benzyloxy-phenyl)-N-tert-butyl-propionamide, and N-Boc-leucine was used instead of N-Boc-N-methyl-leucine.

Step 3: Example 52: [S-(R*,R*)]-2-(4-tert-Butyl-benzylamino)-4-methyl-pentanoic acid [1-(4-benzyloxy-benzyl)-2-(4-benzyl-piperazin-1-yl)-2-oxo-ethyl]-amide is made in accordance with the process of Example 47, except 2-amino-4-methyl-pentanoic acid [1-(4-benzyloxy-benzyl)-2-(4-benzyl-piperazin-1-yl)-2-oxo-ethyl]-amide(Vb) was used instead of 4-methyl-2-methylamino-pentanoic acid [2-(4-benzyloxy-phenyl)-1-tert-butylcarbamoyl-ethyl]-amide, and 4-tert-butylbenzyl-bromide was used instead of 3-bromocyclohexene. MS: 699 (M+1 for $C_{44}H_{56}N_4O_3$); mp 56–57° C.; TLC: $R_f$ 0.7 (EtOAc).

Example 53

[S-(R*,R*)]-4-Methyl-2-(3-methyl-but-2-enylamino)-pentanoic acid [1-(4-benzyloxy-benzyl)-2-(4-benzyl-piperazin-1-yl)-2-oxo-ethyl]-amide is made in accordance with the process of Example 47, except 2-amino-4-methyl-pentanoic acid [1-(4-benzyloxy-benzyl)-2-(4-benzyl-piperazin-1-yl)-2-oxo-ethyl]-amide (Vb) was used instead of 4-Methyl-2-methylamino-pentanoic acid [2-(4-benzyloxy-phenyl)-1-tert-butylcarbamoyl-ethyl]-amide, and 4-bromo-2-methyl-2-butene was used instead of 3-bromocyclohexene.

MS: 616 (M+1 for $C_{38}H_{50}N_4O_3$); sticky solid; TLC: $R_f$ 0.4 (EtOAc).

Example 54

[S-(R*,R*)]-2-(Benzyl-methyl-amino)-4-methyl-pentanoic acid [2-(4-benzyloxy-phenyl)-1-tert-butylcarbamoyl-ethyl]-amide is made in accordance with the process of Example 47 except benzylbromide was used instead of 3-bromocyclohexene.

MS: 557 (M+1 for $C_{34}H_{45}N_3O_3$); mp 134–135° C.; TLC: $R_f$ 0.7 (33% hexanes/EtOAc).

Example 55

[S-(R*,R*)]-2-[(4-tert-Butyl-benzyl)-methyl-amino]-4-methyl-pentanoic acid [2-(4-benzylamino-phenyl)-1-tert-butylcarbamoyl-ethyl]-amide Scheme XIV

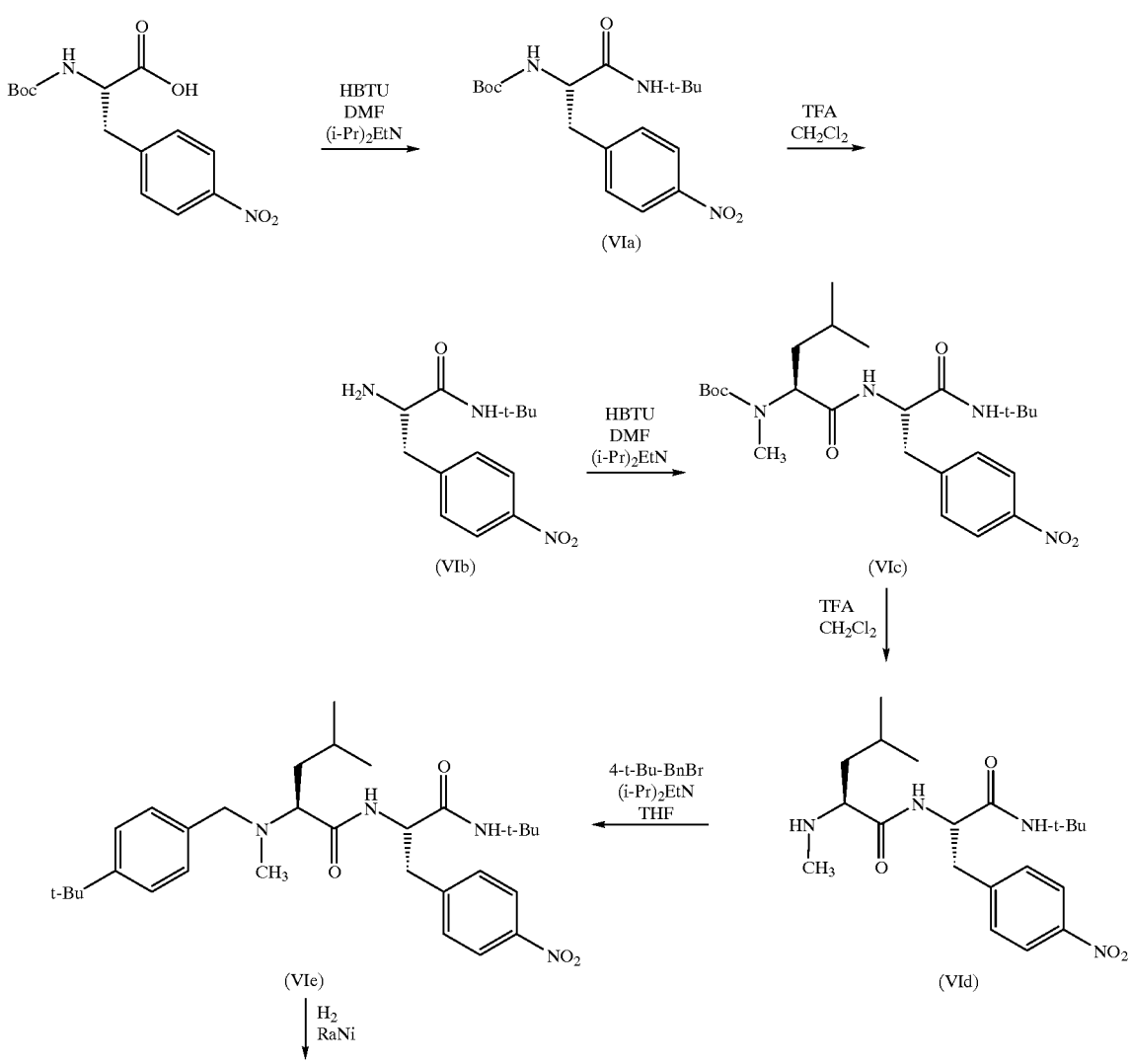

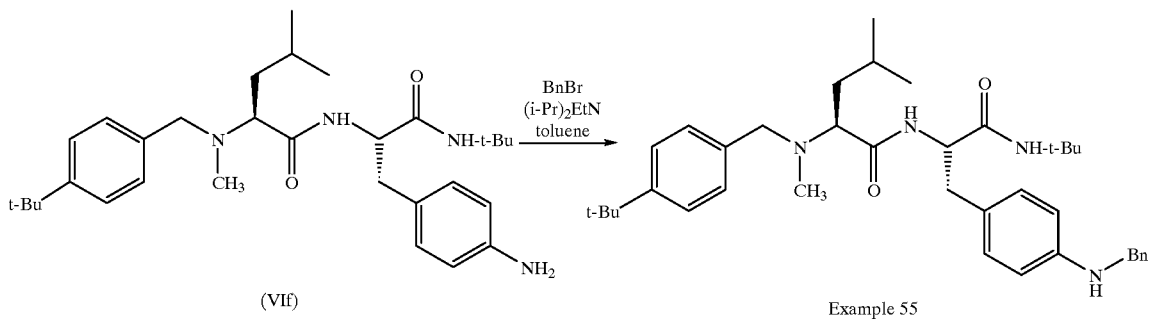

(VIf)    Example 55

Step 1: The Preparation of (S)-[1-tert-Butylcarbamoyl-2-(4-nitro-phenyl)-ethyl]-carbamic acid tert-butyl ester (VIa)

(S)-[1-tert-Butylcarbamoyl-2-(4-nitro-phenyl)-ethyl]-carbamic acid (16.0 g, 51.6 mmol) was dissolved in DMF (258 mL) and treated with diisopropylethylamine (13.5 mL, 77.3 mmol), tert-butylamine (5.4 mL, 51.6 mmol), and HBTU (19.57 g, 51.6 mmol). The reaction was stirred for 4 hours, then diluted with $CH_2Cl_2$ (500 mL), washed with saturated bicarbonate solution (2×500 mL) and brine (500 mL), dried over $Na_2SO_4$, and concentrated to give 18.3 g (97%) of VIa as a pale orange solid.

MS: 366 (M+1 for $C_{18}H_{27}N_3O_5$); TLC $SiO_2$, $R_f$ 0.62 (50% EtOAc/hexanes).

Step 2: The Preparation of (S)-2-Amino-N-tert-butyl-3-(4-nitro-phenyl)-propionamide (VIb)

(S)-[1-tert-Butylcarbamoyl-2-(4-nitro-phenyl)-ethyl]-carbamic acid tert-butyl ester (9.0 g, 24.6 mmol, VIa) was dissolved in $CH_2Cl_2$ (60 mnL) and treated with TFA (50 mL). The solution was stirred for 25 minutes, then concentrated in vacuo and pumped on briefly under high vacuum. The residue was dissolved in EtOAc (300 mL), washed with saturated bicarbonate solution (2×300 mL) and brine (300 mL), dried over $Na_2SO_4$, and concentrated. The crude product was chromatographed on silica gel eluting with 8% $MeOH/CH_2Cl_2$ to give 2.41 g (37%) of VIb.

MS: 266 (M+1 for $C_{13}H_{19}N_3O_3$); TLC $SiO_2$, $R_f$ 0.48 (8% $MeOH/CH_2Cl_2$).

Step 3: The Preparation of [S-(R*,R*)]-{1-[1-tert-Butylcarbamoyl-2-(4-nitro-phenyl)-ethylcarbamoyl]-3-methyl-butyl}-methyl-carbamic acid tert-butyl ester (VIc)

(S)-2-Amino-N-tert-butyl-3-(4-nitro-phenyl)-propionamide (2.41 g, 9.08 mmol, VIb) was dissolved in DMF (45 mL), and treated with diisopropylethylamine (3.15 mL, 18.16 mmol), N-Boc-N-Me-leucine (2.23 g, 9.08 mmol), and HBTU (3.44 g, 9.08 mmol). The reaction was stirred for 1.25 hours, then diluted with EtOAc (300 mL), washed with saturated bicarbonate solution (2×300 mL) and brine (300 mL), dried over $Na_2SO_4$, and concentrated to give 4.44 g (99%) of VIc.

MS: 494 (M+1 for $C_{25}H_{40}N_4O_6$); TLC SiO2, $R_f$ 0.8 (10% $MeOH/CH_2Cl_2$).

Step 4: The Preparation of [S-(R*,R*)]-4-Methyl-2-methylamino-pentanoic acid [1-tert-butylcarbamoyl-2-(4-nitro-phenyl)-ethyl]-amide (VId)

{1-[1-tert-Butylcarbamoyl-2-(4-nitro-phenyl)-ethylcarbamoyl]-3-methyl-butyl}-methyl-carbamic acid tert-butyl ester (4.43 g, 8.99 mmol,VIc) was dissolved in $CH_2Cl_2$ (30 mL) and treated with TFA (21 mL). The solution was stirred for 25 minutes, then concentrated in vacuo and pumped on briefly under high vacuum. The residue was diluted with EtOAc (300 mL), washed with saturated bicarbonate solution (3×300 mL) and brine (300 mL), dried over $Na_2SO_4$, and concentrated to give 3.51 g (99%) of VId.

MS: 394 (M+1 for $C_{20}H_{32}N_4O_4$); mp 162–164° C.

Step 5: [S-(R*,R*)]-2-(4-tert-Butyl-benzylamino)-4-methyl-pentanoic acid [1-tert-butylcarbamoyl-2-(4-nitro-phenyl)-ethyl]-amide (VIe)

4-Methyl-2-methylamino-pentanoic acid [1-tert-butylcarbamoyl-2-(4-nitro-phenyl)-ethyl]-amide (3.41 g, 8.69 mmol, VId) was dissolved in THF (170 mL), and treated with diisopropylamine (6.1 mL, 34.8 mmol), and 4-tert-butyl-benzyl bromide (1.76 mL, 9.56 mmol). The reaction was heated to 40° C. overnight, then the volume was reduced by one-half under reduced pressure and heated to 40° C. for 2 hours. The reaction was filtered, and the solution was concentrated in vacuo. The reside was purified by flash chromatography on silica gel eluting with 33% ethyl acetate/hexanes to give 3.95 g (84%) of VIe. MS: 540 (M+1 for $C_{31}H_{46}N_4O_4$); TLC $SiO_2$, $R_f$ 0.1 (33% EtOAc/hexanes).

Step 6: [S-(R*,R*)]-2-[(4-tert-Butyl-benzyl)-methyl-amino]-4-methyl-pentanoic acid [2-(4-amino-phenyl)-1-tert-butylcarbamoyl-ethyl]-amide (VIf)

[S-(R*,R*)]-2-(4-tert-Butyl-benzylamino)-4-methyl-pentanoic acid [1-tert-butylcarbamoyl-2-(4-nitro-phenyl)-ethyl]-amide (0.96 g, 1.78 mmol, VIe) was dissolved in MeOH (50 mL) and shaken under an $H_2$ atmosphere with Raney Nickel (0.2 g). The catalyst was filtered and the solution concentrated in vacuo to give 0.89 g (98%) of VIf as a white foam.

MS: 510 (M+1 for $C_{31}H_{48}N_4O_2$); mp 80–81° C.; TLC $R_f$ 0.36 (33% EtOAc/hexanes).

Step 7: Example 55: [S-(R*,R*)]-2-[(4-tert-Butyl-benzyl)-methyl-amino]-4-methyl-pentanoic acid [2-(4-benzylamino-phenyl)-1-tert-butylcarbamoyl-ethyl]-amide

[S-(R*,R*)]-2-[(4-tert-Butyl-benzyl)-methyl-amino]-4-methyl-pentanoic acid [2-(4-amino-phenyl)-1-tert-butylcarbamoyl-ethyl]-amide (0.89 g, 1.75 mmol) was dissolved in toluene (18 mL) and treated with diisopropylamine (0.61 mL, 3.5 mmol), and benzyl bromide (0.21 mL, 1.75 mmol). The reaction was stirred at room temperature overnight. After 24 hours, diisopropylamine (0.35 mL, 0.2 eq.) and benzyl bromide (0.021 mL, 0.2 eq.) were added, and the reaction was stirred for 5 hours. The reaction was concentrated and chromatographed on silica gel to give Example 55.

MS: 600 (M+1 for $C_{38}H_{54}N_4O_2$); mp 74–75° C.; TLC $SiO_2$, $R_f$ 0.66 (33% EtOAc/hexanes).

Example 56

[S-(R*,R*)]-2-(Cyclohexyl-methyl-amino)-4-methyl-pentanoic acid [2-(4-benzyloxy-phenyl)-1-tert-butylcarbamoyl-ethyl]-amide O-Benzyl-L-tyrosine-t-butyl-amide (Ia, 0.5 g, 1.53 mmol) was dissolved in DMF (8 mL) and treated with diisopropylethylamine (0.8 mL, 4.6 mmol), N-cyclohexyl-N-methyl-leucine (IId, 0.34 g, 1.53 mmol), and HBTU (0.58 g, 1.53 mmol). The reaction was stirred for 2 hours, then diluted with EtOAc (100 mL), washed with saturated bicarbonate solution (2×100 mL), brine (100 mL), dried over $Na_2SO_4$, and concentrated. The residue was chromatographed on silica gel eluting with 50% EtOAC/hexane. The resulting material was chromatographed again on silica gel eluting with 8% acetone/$CH_2Cl_2$ to give 0.11 g (14%) of the title compound. MS: 537 (M+1 for $C_{33}H_{49}N_3O_3$); TLC: $SiO_2$, $R_f$ 0.57 (10% MeOH/$CH_2Cl_2$).

Examples 57–105
Multiple Parallel Synthesis Using Kaiser Oxime Resin and Solid Phase Quenching Agent
Step 1: Synthesis of highly loaded Boc-Tyr(Bn)-OH resin (Ia)

In a 100-mL reaction vessel equipped with fritted glass filter, 10 g Kaiser oxime resin (0.91 mmol/g load) was washed sequentially with $CH_2Cl_2$ (3×) and DMF (3×). In a separate flask, a solution of 8.44 g Boc-Tyr(Bn)-OH (22.74 mmol) in 40 mL DMF was treated with 7.82 mL diisopropylethylamine (45.5 mmol), 8.62 g HBTU (22.74 mmol) and 3.48 g HOBt (22.74 mmol). The resulting solution was stirred for 10 minutes and was added to the reaction vessel containing the washed Kaiser oxime resin. The suspension was shaken overnight at room temperature, then washed five times with DMF. The entire procedure was repeated three times After the third coupling, the suspension was washed with DMF (3×) and DCM (3×) to give Ia.

Step 2: The Preparation of H-Tyr(OBn)-OH coupled to Kaiser oxime resin (Ib)

The resin (Ia, 10 g, loading between 0.6–0.8 mmol/g) was washed with dimethylformamide (3×) and $CH_2Cl_2$ (3×), and then treated with a solution of 25% trifluoroacetic acid in $CH_2Cl_2$ (v/v) for 30 minutes. The resin was then washed with $CH_2Cl_2$ (3×), 5% diisopropylamine in $CH_2Cl_2$ (v/v), $CH_2Cl_2$ (3×), and dimethylformamide (3×).

Step 3: The Preparation of N,N-Leucine-tyrosine(OBn)-Kaiser oxime resin (Ic)

A solution of N,N-disubstituted leucine (12 mmol) in 50% DMF/NMP (40 mL) was treated with diisopropylethylamine (4.18 mL), HBTU (12 mmol), and Ib (prepared from Step 2), and the resulting suspension was shaken for 1 hour. The resin (Ic) was washed with DMF (5×) and collected.

Step 4: The Preparation of the Polymer-supported Isocyanate (Id)

A suspension of aminomethyl resin (Fluka, 1.1 mmol N/g resin, 15 g, 16.5 mmol) in DCM (150 mL) was treated with $Et_3N$ (11.5 mL, 83 mmol) and triphosgene (3.25 g, 2 mmol equivalents of phosgene) and shaken 5 hours at room temperature. The resulting isocyanate resin was filtered and washed DCM (2×200 mL), $CHCl_3$ (2×200 mL), $Et_2O$ (1×200 mL), THF (1×200 mL), $Et_2O$ (1×200 mL), THF (1×200 mL), $Et_2O$ (1×200 mL). The resin was then dried at 35° C. to 40° C., 25 mmHg for 24 hours. Yield (15 g), IR (KBr) 2260 (N=C=O).

Step 5: Synthesis of the Substituted Peptidylamines
The resin (Ic) prepared from Step 3 was suspended in $CH2Cl_2$, and 1.5 equivalents of the appropriate amine was added. The suspension was shaken for 48 hours. After the reaction was completed, additional $CH_2Cl_2$ was added, with 1 equivalent of Polymer-supported Isocyanate (Id). After the suspension was shaken for 24 hours, the resin was filtered off, and the solvent was evaporated yielding the amorphous product. The purity of the product was analyzed by HPLC: A Model 1050 (Hewlett Packard, Palo Alto, Calif.) system was used for the analytical HPLC. Solvent A: 0.1% TFA/ water and solvent B: 0.09% TFA/acetonitrile, with a linear gradient of 2% B/min starting at 0%. Vydac (The Separations Group, Hesperia, Calif.) C18, 300 Å pore size, 5 µM particle size, 4.6×250 mm column was used, with a flow rate of I mL/min.

Example 57

[S-(R*,R*)]-4-Methyl-2-[methyl-(3-methyl-butyl)-amino]-pentanoic acid [2-(4-benzyloxy-phenyl)-1-(2-morpholin-4-yl-ethylcarbamoyl)-ethyl]-amide
Step 1: Method A of the synthesis of (S)-4-Methyl-2-[methyl-(3-methyl-butyl)-amino]-pentanoic acid (IIb)

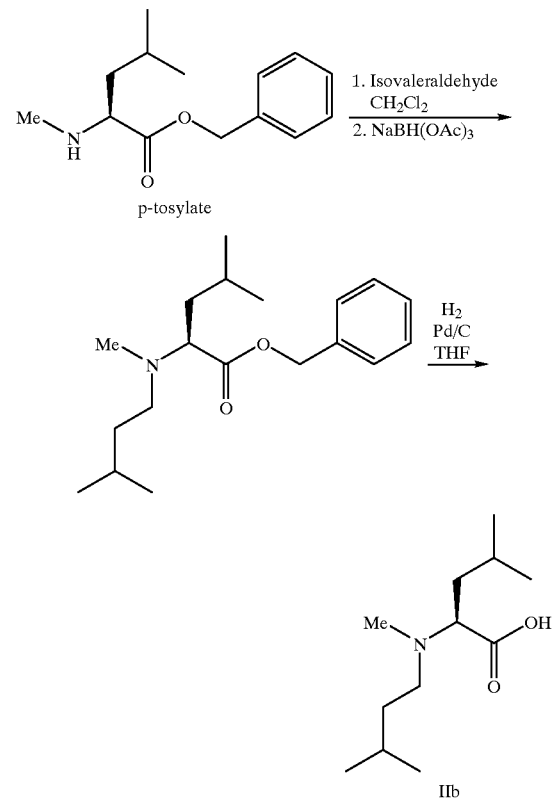

Scheme XV

Step i: N-Methyl-O-benizyl-L-leucine p-tosylate salt (4.01 g, 9.84 mmol) was dissolved in $CH_2Cl_2$ (50 mL) and treated with isovaleraldehyde (1.06 mL, 9.84 mmol). The reaction was stirred at room temperature for 30 minutes and then cooled to 0° C. Sodium triacetoxyborohydride (3.13 g, 14.8 mmol) was added, and the reaction was allowed to warm to room temperature and stir overnight. The reaction was diluted with $CH_2Cl_2$ (400 mL). The organic layer was washed twice with saturated bicarbonate solution (2×400 mL), once with brine (400 mL), and then dried over $Na_2SO_4$. The solution was filtered, concentrated, and the crude material chromatographed on silica gel eluting with 10% EtOAc/hexanes to give 2.86 g (90%) of (S)-4-methyl-2-[methyl-(3-methyl-butyl)-amino]-pentanoic acid benzyl ester as a pale oil.
MS: 306 (M+1 for $C_{19}H_{31}N_1O_2$); TLC: $SiO_2$, $R_f$ 0.33(10% EtOAc/hexanes).
Step ii: (S)-4-methyl-2-[methyl-(3-methyl-butyl)-amino]-pentanoic acid. The benzyl ester (0.89 g, 2.89 mmol) was dissolved in THF (75 mL) and shaken with 20% Pd/C (0.1 g) under an $H_2$ atmosphere (52 psi) for 30 minutes. The catalyst was removed by filtration through a pad of Celite, and the solution was concentrated to give 0.50 g (81%) of IIb as a white solid.

MS: 216 (M+1 for $C_{12}H_{25}N_1O_2$); TLC: $SiO_2$, $R_f$ 0.32 (10% MeOH/$CH_2Cl_2$).

Step 1: Method B of the synthesis of (S)-4-Methyl-2-[methyl-(3-methyl-butyl)-amino]-pentanoic acid (IIb)

Step i: A vessel containing 100 g of L-Leucine, 1600 mL of ethanol, 8 g of 2% Pd/C, and 131.5 g of isovaleraldehyde was shaken under hydrogen. After the reaction was finished, the ethanol solution was collected by filtration. Then 300 mL of concentrated HCl was added to the Pd/C-compound mixture, and the mixture was filtered again to give the second filtrate. The second filtration provided the product in concentrated HCl, and it was added NaOH to pH 6.5. The product precipitated out as a white solid, and it was collected by filtration. The crude product was washed with water (200 mL) and acetone (300 mL), then it was dried under vacuum to yield N-(2-methylbutyl)-leucine (50 g); mp 275° C. (dec.).

MS: 202 (M+1 for $C_{11}H_{23}N_1O_2$).

Analysis calculated for $C_{11}H_{23}N_1O_2$: C, 65.63; H, 11.52; N, 6.96. Found: C, 65.50; H, 11.40; N, 6.88.

Step ii: A vessel containing 48 g of N-(2-methylbutyl)-L-leucine, 1.5 L of ethanol, 50 mL of $CH_2O$ (37%, 3 eq.), and 3.0 g of 20% Pd/C was shaken under hydrogen. After the reaction was finished, the ethanol solution was collected by filtration. The ethanol solution was concentrated to dryness. Water (30 mL) was added to help removing $CH_2O$, then it was concentrated to dryness; this step was repeated three times. The crude product was stirred with hot acetone (200 mL) for 2 hours and continued stirring at 25° C. for another 18 hours. Then the product was collected by filtration and dried under vacuum to yield (S)4-methyl-2-[methyl-(3-methyl-butyl)-amino]-pentanoic acid (IIb) (40 g); mp 159–160° C. (dec.). MS: 216 (M+1 for $C_{12}H_{25}N_1O_2$).

Analysis calculated for $C_{12}H_{25}N_1O_2$: C, 66.93; H, 11.70; N, 6.50. Found: C, 66.72; H, 11.99; N, 6.45.

Step 2: The Preparation of N-(2-methylbutyl)-N-methyl-leucine-tyrosine(OBn)-Kaiser oxime resin (IIc)

A solution of IIb (4.55 mmol) in 30 mL of DMF was treated with diisopropylethylamine (9.1 mmol), HBTU (4.55 mmol), Ib, and HOBt (4.55 mmol), and the resulting suspension was shaken for 1 hour. The resin was washed with DMF (5×) and collected to yield IIc.

Step 3: The Preparation of [S-(R*,R*)]-4-Methyl-2-[methyl-(3-methyl-butyl)-amino]-pentanoic acid [2-(4-benzyloxy-phenyl)-1-(2-morpholin-4-yl-ethylcarbamoyl)-ethyl]-amide The resin (IIc) was suspended in $CH_2Cl_2$ and 1.5 equivalents of 2-morpholin-4-yl-ethylamine. The suspension was shaken for 48 hours. After the reaction was completed, additional amount of $CH_2Cl_2$ and 1 equivalent of Polymer-supported Isocyanate were added. After the suspension was shaken for 24 hours, the resin was filtered off, and the solvent was evaporated to yield the title product.

MS: 581 (M+1); HPLC retention Time: 22.44 minutes.

Example 58

[S-(R*,R*)]-4-Methyl-2-[methyl-(3-methyl-butyl)-amino]-pentanoic acid [2-(4-benzyloxy-phenyl)-1-(2-pyridin-2-yl-ethylcarbamoyl)-ethyl]-amide was prepared in accordance with the procedure of Example 57 (Step 3), except 2-(2-aminoethyl)pyridine was used instead of 2-morpholin-4-yl-ethylamine.

MS: 573.5 (M+1); HPLC retention Time: 22.69 minutes.

Example 59

[S-(R*,R*)]-4-Methyl-2-[methyl-(3-methyl-butyl)-amino]-pentanoic acid [2-(4-benzyloxy-phenyl)-1-(3-imidazol-1-yl-propylcarbamoyl)-ethyl]-amide was prepared in accordance with the procedure of Example 57 (Step 3), except histamine was used instead of 2-morpholin-4-yl-ethylamine.

MS: 576.5 (M+1); HPLC retention Time: 22.57 minutes.

Example 60

[S(R*,R*)]-4-Methyl-2-[methyl-(3-methyl-butyl)-amino]-pentanoic acid [1-(2-benzylamino-ethylcarbamoyl)-2-(4-benzyloxy-phenyl)-ethyl]-amide was prepared in accordance with the procedure of Example 57 (Step 3), except $N^1$-benzyl-ethane-1,2-diamine was used instead of 2-morpholin-4-yl-ethylamine.

MS: 601.3 (M+1); HPLC retention Time: 24.98 minutes.

Example 61

[S-(R*,R*)]-4-Methyl-2-[methyl-(3-methyl-butyl)-amino]-pentanoic acid [1-(4-benzyloxy-benzyl)-2-oxo-2-thiomorpholin-4-yl-ethyl]-amide was prepared in accordance with the procedure of Example 57 (Step 3), except thiomorpholine was used instead of 2-morpholin-4-yl-ethylamine.

MS: 554.5 (M+1); HPLC retention Time: 29.60 minutes.

Example 62

[S-(R*,R*)]-4-Methyl-2-[methyl-(3-methyl-butyl)-amino]-pentanoic acid [2-(4-benzyloxy-phenyl)-1-(2-hydroxy-1-hydroxymethyl-1-methyl-ethylcarbamoyl)-ethyl]-amide was prepared in accordance with the procedure of Example 57 (Step 3), except 2-amino-2-methyl-propane-1,3-diol was used instead of 2-morpholin-4-yl-ethylamine.

MS: 570.5 (M+1); HPLC retention Time: 25.62 minutes.

Example 63

[S-(R*,R*)]-4-Methyl-2-[methyl-(3-methyl-butyl)-amino]-pentanoic acid [2-(4-benzyloxy-phenyl)-1-(1-methoxymethyl-propylcarbamoyl)-ethyl]-amide was prepared in accordance with the procedure of Example 57 (Step 3), except 1-methoxymethyl-propylamine was used instead of 2-morpholin-4-yl-ethylamine.

MS: 554.5 (M+1); HPLC retention Time: 28.5,28.7 minutes.

Example 64

[S-(R*,R*)]-4-Methyl-2-[methyl-(3-methyl-butyl)-amino]-pentanoic acid [2-(4-benzyloxy-phenyl)-1 -(2-pyrrolidin-1-yl-ethylcarbamoyl)-ethyl]-amide was prepared in accordance with the procedure of Example 57 (Step 3), except 2-pyrrolidin-1-yl-ethylamine was used instead of 2-morpholin-4-yl-ethylamine.

MS: 565.5 (M+1); HPLC retention Time: 22.8 minutes.

Example 65

[S-(R*,R*)]-4-Methyl-2-[methyl-(3-methyl-butyl)-amino]-pentanoic acid [1-(4-benzyloxy-benzyl)-2-(4-hydroxy-piperidin-1-yl)-2-oxo-ethyl]-amide was prepared in accordance with the procedure of Example 57 (Step 3), except piperidin-4-ol was used instead of 2-morpholin-4-yl-ethylamine.

MS: 552.5 (M+1); HPLC retention Time: 25.1 minutes.

Example 66

[S-(R*,R*)]-4-Methyl-2-[methyl-(3-methyl-butyl)-amino]-pentanoic acid {2-(4-benzyloxy-phenyl)-1-[2-(2- hydroxy-ethylamino)-ethylcarbamoyl]-ethyl}-amide was prepared in accordance with the procedure of Example 57 (Step 3), except 2-(2-amino-ethylamino)-ethanol was used instead of 2-morpholin-4-yl-ethylamine.

MS: 555.5 (M+1); HPLC retention Time: 22.3 minutes.

Example 67

[S-(R*,R*)]-4-Methyl-2-[methyl-(3-methyl-butyl)-amino]-pentanoic acid [2-(4-benzyloxy-phenyl)-1-(1-benzyl-pyrrolidin-3-ylcarbamoyl)-ethyl]-amide was prepared in accordance with the procedure of Example 57 (Step 3), except 1-benzyl-pyrrolidin-3-ylamine was used instead of 2-morpholin-4-yl-ethylamine.

MS: 627.6 (M+1); HPLC retention Time: 25.3 minutes.

Example 68

[S-(R*,R*)]-4-Methyl-2-morpholin4-yl-pentanoic acid [1-(2-benzylamino-ethylcarbamoyl)-2-(4-benzyloxy-phenyl)-ethyl]-amide was prepared in accordance with the procedure of Example 57 (Step 3), except $N^1$-benzyl-ethane-1,2-diamine was used instead of 2-morpholin-4-yl-ethylamine, and [S-(R*,R*)]-4-methyl-2-morphlin-4-yl-pentanoic acid-tyrosine(OBn)-Kaiser oxime resin was used instead of IIc. (Step 3)

[S-(R*,R*)]-4-methyl-2-morphlin-4-yl-pentanoic acid-tyrosine(OBn)-Kaiser oxime resin was prepared in accordance with the procedure of Example 57 (Step 2), except (S)-4-methyl-2-morpholin-4-yl-pentanoic acid was used instead of (S)-4-Methyl-2-[methyl-(3-methyl-butyl)-amino]-pentanoic acid (IIb).

(S)-4-methyl-2-morpholin-4-yl-pentanoic acid was made in accordance with the literature procedure (Kwapiszewki W. and Bialasiewicz W., Acta Pol. Pharm., 1994;51(3):227–229).

MS: 587.3 (M+1); HPLC retention Time: 30.72 minutes.

Example 69

[S-(R*,R*)]-4-Methyl-2-morpholin-4-yl-pentanoic acid [2-(4-benzyloxy-phenyl)-1-(1-benzyl-pyrrolidin-3-ylcarbamoyl)-ethyl]-amide was prepared in accordance with the procedure of Example 68 (Step 3), except 1-benzyl-pyrrolidin-3-ylamine was used instead of $N^1$-benzyl-ethane-1,2-diamine.

MS: 613.3 (M+1); HPLC retention Time: 21.80 minutes.

Example 70

[S-(R*,R*)]-4-Methyl-2-morpholin-4-yl-pentanoic acid [1-(4-benzyloxy-benzyl)-2-oxo-2-piperidin-1-yl-ethyl]-amide was prepared in accordance with the procedure of Example 68 (Step 3), except piperidine was used instead of $N^1$-benzyl-ethane-1,2-diamine.

MS: 522.3 (M+1); HPLC retention Time: 26.21 minutes.

Example 71

[S-(R*,R*)]-4-Methyl-2-(tetrahydro-pyran-4-ylamino)-pentanoic acid [1-(2-benzylamino-ethylcarbamoyl)-2-(4-benzyloxy-phenyl)-ethyl]-amide was prepared was prepared in accordance with the procedure of Example 57 (Step 3), except $N^1$-benzyl-ethane-1,2-diamine was used instead of 2-morpholin4-yl-ethylamine and N-methyl-N-(tetrahydro-pyran-4-yl)-leucine-tyrosine(OBn)-Kaiser oxime resin was used instead of IIc. (Step 3)

N-methyl-N-(tetrahydro-pyran4-yl)-leucine-tyrosine (OBn)-Kaiser oxime resin was prepared in accordance with the procedure of Example 57 (Step 2), except 4-methyl-2-(tetrahydro-pyran-4-ylamino)-pentanoic acid was used instead of (S)-4-methyl-2-[methyl-(3-methyl-butyl)-amino]-pentanoic acid (IIb).

4-methyl-2-(tetrahydro-pyran-4-ylamino)-pentanoic acid was made in accordance with the procedure of Example 57 (Step 1), except tetrahydro-4H-pyran-4-one was used instead of isovaleraldehyde.

MS: 615.3 (M+I); HPLC retention Time: 21.96 minutes.

Example 72

[S-(R*,R*)]-4-Methyl-2-(tetrahydro-pyran-4-ylamino)-pentanoic acid [1-(4-benzyloxy-benzyl)-2-oxo-2-thiomorpholin-4-yl-ethyl]-amide was prepared in accordance with the procedure of Example 71 (Step 3), except thiomorpholine was used instead of $N^1$-benzyl-ethane-1,2-diamine.

MS: 568.3 (M+1); HPLC retention Time: 26. 1 minutes.

Example 73

[S-(R*,R*)]-4-Methyl-2-(tetrahydro-pyran4-ylamino)-pentanoic acid [2-(4-benzyloxy-phenyl)-1-(2-hydroxy-1,1-dimethyl-ethylcarbamoyl)-ethyl]-amide was prepared in accordance with the procedure of Example 71 (Step 3), except 2-amino-2-methyl-propan-1-ol was used instead of $N^1$-benzyl-ethane-1,2-diamine.

MS: 554.3 (M+1); HPLC retention Time: 23.0 minutes.

Example 74

[S-(R*,R*)]-4-Methyl-2-(tetrahydro-pyran-4-ylamino)-pentanoic acid [2-(4-benzyloxy-phenyl)-1-(1,1-bis-hydroxymethyl-propylcarbamoyl)-ethyl]-amide was prepared in accordance with the procedure of Example 71 (Step 3), except 2-amino-2-methyl-propane-1,3-diol was used instead of $N^1$-benzyl-ethane-1,2-diamine.

MS: 584.3 (M+1); HPLC retention Time: 21.8 minutes.

Example 75

[S-(R*,R*)]-4-Methyl-2-(tetrahydro-pyran-4-ylamino)-pentanoic acid [2-(4-benzyloxy-phenyl)-1-(1-methoxymethyl-propylcarbamoyl)-ethyl]-amide was prepared in accordance with the procedure of Example 71 (Step 3), except 1-methoxymethyl-propylamine was used instead of $N^1$-benzyl-ethane-1,2-diamine.

MS: 568.4 (M+1); HPLC retention Time: 25.1, 25.5 minutes.

Example 76

[S-(R*,R*)]-4-Methyl-2-(tetrahydro-pyran4-ylamino)-pentanoic acid [2-(4-benzyloxy-phenyl)-1-(1-benzyl-pyrrolidin-3-ylcarbamoyl)-ethyl]-amide was prepared in accordance with the procedure of Example 71 (Step 3), except 1-benzyl-pyrrolidin-3-ylamine was used instead of $N^1$-benzyl-ethane-1,2-diamine.

MS: 641.4 (M+1); HPLC retention Time: 22.1 minutes.

Example 77

[S-(R*,R*)]-4-Methyl-2-(tetrahydro-pyran-4-ylamino)-pentanoic acid [2-(4-benzyloxy-phenyl)-1-(2-piperidin-1-yl-ethylcarbamoyl)-ethyl]-amide was prepared in accordance with the procedure of Example 71 (Step 3), except 2-piperidin-1-yl-ethylamine was used instead of $N^1$-benzyl-ethane- 1,2-diamine.

MS: 593.4 (M+1); HPLC retention Time: 20.1 minutes.

Example 78

[S-(R*,R*)]-4-Methyl-2-(tetrahydro-pyran-4-ylamino)-pentanoic acid [2-(4-benzyloxy-phenyl)-1-tertbutylcarbamoyl-ethyl]-amide was prepared in accordance with the procedure of Example 71 (Step 3), except t-butylamine was used instead of $N^1$-benzyl-ethane-1,2-diamine.

MS: 538.3 (M+1); HPLC retention Time: 27.2 minutes.

Example 79

[S-(R*,R*)]-4-Methyl-2-(tetrahydro-pyran-4-ylamino)-pentanoic acid [1-(4-benzyloxy-benzyl)-2-oxo-2-piperidin-1-yl-ethyl]-amide was prepared in accordance with the procedure of Example 71 (Step 3), except piperidine was used instead of $N^1$-benzyl-ethane-1,2-diamine.

MS: 550.4 (M+1); HPLC retention Time: 26.5 minutes.

Example 80

[S-(R*,R*)]-2-[(4-Fluoro-benzyl)-methyl-amino]-4-methyl-pentanoic acid [2-(4-benzyloxy-phenyl)-1-tert-butylcarbamoyl-ethyl]-amide Step 1: The Preparation of (S)-2-Amino-3-(4-benzyloxy-phenyl)-N-tert-butyl-propionamide (Ia) was prepared as Example 1 (Step 1).

Step 2: The Preparation of [S-(R*,R*)]-4-Methyl-2-methylamino-pentanoic acid [2-(4benzyloxy-phenyl)-1-tert-butylcarbamoyl-ethyl]-amide Step i: (S)-2-Amino-3-(4-benzyloxy-phenyl)-N-tert-butyl-propionamide (7.0 g, 21.4 mmol) (Ia) was dissolved in $CH_3CN$ (75 mL) and treated with diisopropylethylamine (3.72 mL, 21.4 mmol), N-Boc-N-Me-L-leucine (3.51 g, 14.3 mmol), and HBTU (5.42 g, 14.3 mmol). The reaction was stirred for 30 minutes and then concentrated. The residue was dissolved in EtOAc (300 mL), washed with saturated bicarbonate solution (2×300 mL) and brine (300 mL), dried over $Na_2SO_4$, and concentrated. The crude material was chromatographed on silica gel eluting with 25% EtOAc/hexanes to give 7.0 g (88%) of [S-(R*,R*)]-{1-[2-(4-benzyloxy-phenyl)-1-tert-butylcarbamoyl-ethylcarbamoyl]-3-methyl-butyl}-methyl-carbamic acid tert-butyl ester.

MS: 554 (M+1 for $C_{32}H_{46}N_3O_5$); TLC: $SiO_2$, $R_f$ 0.26 (8% MeOH/$CH_2Cl_2$).

Step ii: [S-(R*,R*)]-{1-[2-(4-Benzyloxy-phenyl)-1-tert-butylcarbamoyl-ethylcarbamoyl]-3-methyl-butyl}-methyl-carbamic acid tert-butyl ester (4.0 g, 7.24 mmol) was dissolved in $CH_2Cl_2$ (24 mL) and treated with trifluoroacetic acid (16 mL). The reaction was stirred for 15 minutes, then concentrated, diluted with EtOAc (300 mL), washed with bicarbonate solution (3×300 mL) and brine (300 mL), dried over $Na_2SO_4$, and concentrated. The crude material was chromatographed on silica gel eluting with 8% MeOH/$CH_2Cl_2$ to give 2.8 g (85%) of [S-(R*,R*)]-4-methyl-2-methylamino-pentanoic acid [2-(4-benzyloxy-phenyl)-1-tert-butylcarbamoyl-ethyl]-amide.

MS: 454 (M+1 for $C_{27}H_{38}N_3O_3$); TLC: $SiO_2$, $R_f$ 0.19 (8% MeOH/$CH_2Cl_2$).

Step 3: Example 80: [S-(R*,R*)]-2-[(4-Fluoro-benzyl)-methyl-amino]-4-methyl-pentanoic acid [2-(4-benzyloxy-phenyl)-1-tert-butylcarbamoyl-ethyl]-amide

[S-(R*,R*)]-4-Methyl-2-methylamino-pentanoic acid [2-(4-benzyloxy-phenyl)-1-tert-butylcarbamoyl-ethyl]-amide (0.3 g, 0.66 mmol) was dissolved in $CH_2Cl_2$ (5 mL) and treated with 4-fluorobenzaldehyde (0.082 g, 0.66 mmol). The reaction was stirred for 30 minutes, then cooled to 0° C. and treated with sodium triacetoxyborohydride (0.21 g, 1 mmol). The reaction was allowed to warm to room temperature and stirred overnight. The reaction was diluted with EtOAc (100 mL), washed with saturated bicarbonate solution (2×100 mL) and brine (100 mL), dried over $Na_2SO_4$, and concentrated. The residue was chromatographed on silica gel eluting with 6% MeOH/$CH_2Cl_2$ to give 0.29 g (78%) of the title compound.

MS: 562 (M+1 for $C_{34}H_{44}N_3O_3F_1$); mp 125–126° C.; TLC: $R_f$ 0.56 (6% MeOH/$CH_2Cl_2$).

Example 81

[S-(R*,R*)]-2-[(4-Bromo-benzyl)-methyl-amino]4-methyl-pentanoic acid [2-(4-benzyloxy-phenyl)-1-tert-butylcarbamoyl-ethyl]-amide was made in accordance with the procedure of Example 80 (Step 3), except that 4-bromobenzaldehyde was used instead of 4-fluorobenzaldehyde.

MS: 623 (M+1 for $C_{34}H_{44}N_3O_3Br_1$); mp 122–123° C.; TLC: Rf 0.47 (6% MeOH/$CH_2Cl_2$).

Example 82

[S-(R*,R*)]-2-[(4-Hydroxy-benzyl)-methyl-amino]-4-methyl-pentanoic acid [2-(4-benzyloxy-phenyl)-1-tert-butylcarbamoyl-ethyl]-amide was made in accordance with the procedure of Example 80 (Step 3), except that 4-hydroxybenzaldehyde was used instead of 4-fluorobenzaldehyde.

MS: 560 (M+1 for $C_{34}H_{45}N_3O_4$); mp 123–124° C.; TLC: $R_f$ 0.39 (6% MeOH/$CH_2Cl_2$).

Example 83

[S-(R*,R*)]-4-Methyl-2-(methyl-pyridin4-ylmethyl-amino)-pentanoic acid [2-(4-benzyloxy-phenyl)-1-tert-butylcarbamoyl-ethyl]-amide was made in accordance with the procedure of Example 80 (Step 3), except that 4-pyridinecarboxaldehyde was used instead of 4-fluorobenzaldehyde.

MS: 545 (M+1 for $C_{33}H_{44}N_4O_3$); mp: 135–136° C.; TLC: $R_f$ 0.17 (5% MeOH/$CH_2Cl_2$).

Example 84

[S-(R*,S*)]-4-Methyl-2-[methyl-(3-methyl-butyl)-amino]-pentanoic acid [2-(4-benzyloxy-phenyl)-1-tert-butylcarbamoyl-ethyl]-amide was made in accordance with the procedure of Example 80, except that N-Boc-N-Me-D-leucine was used instead of N-Boc-N-Me-L-leucine in Step 2 (i), and isovaleraldehyde was used instead of 4-fluorobenzaldehyde in Step 3.

MS: 524 (M+1 for $C_{32}H_{49}N_3O_3$); sticky solid; TLC: $R_f$ 067 (10% MeOH/$CH_2Cl_2$).

Example 85

[S-(R*,R*)]-3-(4-Benzyloxy-phenyl)-2-[4-methyl-2-(tetrahydro-pyran-4-ylamino)-pentanoylamino]-propionic acid tert-butyl ester Step 1: The Preparation of (S)-2-Amino-3-(4-benzyloxy-phenyl)-propionic acid tert-butyl ester A solution of L-tyrosine-OBn (50.0 g, 0.184 mol) was dissolved in dioxane (500 mL). The reaction vessel was charged with isobutylene (500 mL) and concentrated sulfuric acid (50 mL). The reaction vessel was sealed and shaken for 64 hours. The reaction mixture was vented and poured into a rapidly stirring mixture of KOH (104 g) in ice water (1000 mL). The resulting mixture was extracted into ether (5×200 mL), and the combined organic extracts were dried ($MgSO_4$), filtered and concentrated. The residue was purified by chromatography (silica gel, 2:1 $CHCl_3$/EtOAc). The residue obtained from the chromatography solidified on standing to give the product as a tan solid (35.3 g, 59%).

Step 2: The Preparation of [S-(R*,R*)]-3-(4-Benzyloxy-phenyl)-2-{2-[(9H-fluoren-9-ylmethyl)-amino]-4-methyl-pentanoylamino}-propionic acid tert-butyl ester A solution of FMOC-leucine (10.3 g, 29 mmol) in 300 mL of DMF was cooled to 0° C. and treated with diisopropyl-ethyl amine (73 mL) and HBTU (11.1 g, 29.2 mmol). The resulting solution was stirred at 0° C. for 30 minutes and treated with (S)-2-amino-3-(4-benzyloxy-phenyl)-propionic acid tert-butyl ester (110 g, 36.9 mmol). The resulting solution was stirred for 30 minutes at 0° C. and warmed to room temperature. The reaction mixture was poured into 500 mL of ether and washed sequentially with IN aqueous HCl, saturated aqueous $NaHCO_3$ (100 mL) and brine (5×100 mL). The organic phase was collected, dried over $MgSO_4$ and concentrated to near dryness. The residue was triturated with hexane. The product was collected by suction filtration and air dried to give the title compound as a white solid (12.16 g, 70%); mp 158–160° C.

Analysis calculated $C_{41}H_{46}N_2O_6$:
C, 74.30; H, 7.00; N, 4.23.
Found: C, 74.21; H, 7.25; N, 4.20.

Step 3: The Preparation of [S-(R*,R*)]-2-{2-Amino-4-methyl-pentanoylamino}-3-(4-benzyloxy-phenyl)-propionic acid tert-butyl ester A solution of [S-(R*,R*)]-3-(4-benzyloxy-phenyl)-2-{2-[(9H-fluoren-9-ylmethyl)-amino]-4-methyl pentanoylamino}-propionic acid tert-butyl ester (12.2 g, 20.0 mmol) in 500 mL of tetrahydrofuran was treated with piperidine (80 mL). The resulting solution was stirred at room temperature for 48 hours. The reaction mixture was concentrated and the residue purified by chromatography (SiO2, gradient elution EtOAc - 15% EtOH/EtOAc). The resulting yellow solid was broken up in heptane to give the title compound as a white solid (6.77 g, 77%).

Step 4: Example 85: [S-(R*,R*)]-3-(4-Benzyloxy-phenyl)-2-[4-methyl-2-(tetrahydro-pyran-4-ylamino)-pentanoylamino]-propionic acid tert-butyl ester was made in accordance with the procedure of Example 80 (Step 3), except that [S-(R*,R*)]-2-{2-amino4-methyl-pentanoylamino}-3-(4-benzyloxy-phenyl)-propionic acid tert-butyl ester was used instead of [S-(R*,R*)]-4-methyl-2-methylamino-pentanoic acid [2-(4-benzyloxy-phenyl)-1-tert-butylcarbamoyl-ethyl]-amide, and tetrahydropyran-4-one was used instead of 4-fluorobenzaldehyde.

MS: 525 (M+1 for $C_{31}H_{45}N_3O_4$); sticky solid; TLC: $R_f$0.56 (7% MeOH/$CH_2Cl_2$).

Example 86

[S-(R*,R*)]-2-(Isopropyl-methyl-amino)-4-methyl-pentanoic acid [2-(4-benzyloxy-phenyl)-1-tert-butylcarbamoyl-ethyl]-amide was made in accordance with the procedure of Example 80 (Step 3), except that acetone was used instead of 4-fluorobenzaldehyde.

MS: 497 (M+1 for $C_{30}H_{45}N_3O_3$); TLC: $R_f$0.32 (20% acetone/$CH_2Cl_2$).

Example 87

[S-(R*,R*)]-4-Methyl-2-[methyl-(tetrahydro-pyran-4-yl)-amino]-pentanoic acid [2-(4-benzyloxy-phenyl)-1-tert-butylcarbamoyl-ethyl]-amide as made in accordance with the procedure of Example 80 (Step 3), except that tetrahydropyran-4-one was used instead of 4-fluorobenzaldehyde.

MS: 539 (M+1 for $C_{32}H_{47}N_3O_4$); sticky solid; TLC: Rf 0.54 (5% MeOH/CH2Cl$_2$).

Example 88

[S-[R*,R*,(RS)]]-2-[(2-Hydroxy-1-methyl-ethyl)-methyl-amino]-4-methyl-pentanoic acid [2-(4-benzyloxy-phenyl)-1-tert-butylcarbamoyl-ethyl]-amide was made in accordance with the procedure of Example 80 (Step 3), except that 1-hydroxy-propan-2-one was used instead of 4-fluorobenzaldehyde.

MS: 512 (M+1 for $C_{30}H_{45}N_3O_4$); TLC: $R_f$0.39 (5% MeOH/$CH_2Cl_2$).

Example 89

[S-(R*,R*)]-4-Methyl-2-[methyl-(1H-pyrrol-2-ylmethyl)-amino]-pentanoic acid [2-(4-benzyloxy-phenyl)-1-tert-butylcarbamoyl-ethyl]-amide was made in accordance with the procedure of Example 80 (Step 3), except that pyrrole-2-carboxaldehyde was used instead of 4-fluorobenzaldehyde.

MS: 533 (M+1 for $C_{32}H_{44}N_4O_3$); mp 60–62° C.; TLC $R_f$0.47 (5% MeOH/$CH_2Cl_2$).

Example 90

[S-(R*,R*)]-2-(Furan-2-ylmethyl-methyl-amino)-4-methyl-pentanoic acid [2-(4-benzyloxy-phenyl)-1-tert-butylcarbamoyl-ethyl]-amide was made in accordance with the procedure of Example 80 (Step 3), except that furan-2-carboxaldehyde was used instead of 4-fluorobenzaldehyde.

MS: 534 (M+1 for $C_{32}H_{43}N_3O_4$); sticky solid; TLC $R_f$0.53 (5% MeOH/$CH_2Cl_2$).

Example 91

[S-(R*,R*)]-3-(4Benzyloxy-phenyl)-2-[2-(cyclohexylmethyl-amino)-4-methyl-pentanoylamino]-propionic acid tert-butyl ester was made in accordance with the procedure of Example 80 (Step 3), except that [S-(R*,R*)]-2-{2-amino-4-methyl-pentanoylamino}-3-(4-benzyloxy-phenyl)-propionic acid tert-butyl ester was used instead of [S-(R*,R*)]-4-methyl-2-methylamino-pentanoic acid [2-(4-benzyloxy-phenyl)-1-tert-butylcarbamoyl-ethyl]-amide and cyclohexanecarboxaldehyde was used instead of 4-fluorobenzaldehyde.

MS: 537 (M+1 for $C_{33}H_{49}N_3O_3$); sticky solid; TLC: Rf 0.46 (5% MeOH/$CH_2Cl_2$).

Example 92

[S-(R*,R*)]-3-(4-Benzyloxy-phenyl)-2-(2-isopropylamino4-methyl-pentanoylamino)-propionic acid tert-butyl ester was made in accordance with the procedure of Example 80 (Step 3), except that [S-(R*, R*)]-2-{2-amino-4-methyl-pentanoylamino}-3-(4-benzyloxy-phenyl)-propionic acid tert-butyl ester was used instead of [S-(R*,R*)]-4-methyl-2-methylamino-pentanoic acid [2-(4-benzyloxy-phenyl)-1-tert-butylcarbamoyl-ethyl]-amide,and acetone was used instead of 4-fluorobenzaldehyde.

MS: 483 (M+1 for $C_{29}H_{43}N_3O_3$); TLC: $R_f$0.36 (5% MeOH/$CH_2Cl_2$).

Example 93

[S-(R*,R*)]-3-(4-Benzyloxy-phenyl)-2-(2-cyclohexylamino-4-methyl-pentanoylamino)-propionic acid tert-butyl ester was made in accordance with the procedure of Example 80 (Step 3), except that [S-(R*, R*)]-2-{2-amino-4-methyl-pentanoylamino}-3-(4-benzyloxy-phenyl)-propionic acid tert-butyl ester was used instead of [S-(R*,R*)]-4-methyl-2-methylamino-pentanoic acid [2-(4-benzyloxy-phenyl)-1-tert-butylcarbamoyl-ethyl]-amide, and cyclohexanone was used instead of 4-fluorobenzaldehyde.

MS: 523 (M+1 for $C_{32}H_{47}N_3O_3$); sticky solid; TLC: $R_f$0.36 (5% MeOH/$CH_2Cl_2$).

Example 94

[S-(R*,R*)]-4-Methyl-2-morpholin-4-yl-pentanoic acid [2-(4-benzyloxy-phenyl)-1-tert-butylcarbamoyl-ethyl]-amide Step 1: (S)-4-Methyl-2-morpholin4-yl-pentanoic acid was synthesized according to the procedure described in *Acta Poloniae Pharmaceutica—Drug Research,* 1994;51:227–229.

Step 2: (S)-4-Methyl-2-morpholin-4-yl-pentanoic acid (0.161 g, 0.800 mmol) was dissolved in dry DMF (4 mL) under nitrogen atmosphere and cooled to 0° C. in an ice-water bath. To this solution were added in succession N,N-diisopropyl-ethylamine (0.420 mL, 2.41 mmol) and solid O-benzotriazol-1-yl-N,N,N',N'-tetramethyluronium hexafluorophosphate (0.303 g, 0.799 mmol). The resulting reaction mixture was stirred at that temperature for 30 minutes, solid (S)-2-amino-3-(4-benzyloxy-phenyl)-N-tert-butyl-propionamide monohydrochloride (0.290 g, 0.800 mmol) was then added. After stirring for, sequentially, 10 minutes at 0° C. and 45 minutes at ambient temperature, reaction mixture was mixed with 60 mL of diethyl ether. The resulting mixture was successively washed with saturated aqueous $NaHCO_3$ solution (2×60 mL), brine (2×60 mL), and was dried over $Na_2SO_4$. The solution was concentrated in vacuo affording a viscous oil. The crude product was further purified by flash chromatography (60% EtOAc in hexane) and treated with ethereal HCl. Subsequent concentration in vacuo, trituration with ether and drying under vacuum provided 0.27 g (62%) of the pure titled compound as a white solid.

MS: 546 (M+for $C_{30}H_{43}N_3O_4$); mp: 261–263° C.

Example 95

[S-(R*,R*)]-3-(4-Benzyloxy-phenyl)2-[4-methyl-2-(3-methyl-butylamino)-pentanoylamino]-propionic acid tert-butyl ester was made in accordance with the procedure of Example 80 (Step 3), except that [S-(R*,R*)]-2-{2-amino-4-methyl-pentanoylamino}-3-(4-benzyloxy-phenyl)-propionic acid tert-butyl ester was used instead of [S-(R*,R*)]-4-methyl-2-methylamino-pentanoic acid [2-(4-benzyloxy-phenyl)-1-tert-butylcarbamoyl-ethyl]-amide and isovaleraldehyde was used instead of 4-fluorobenzaldehyde.

MS: 511 (M+1 for $C_{31}H_{47}N_3O_3$); sticky solid; TLC: $R_f$0.42 (5% MeOH/$CH_2Cl_2$).

Example 96

[S-(R*,R*)]-({1-[2-(4-Benzyloxy-phenyl)-1-tert-butylcarbamoyl-ethylcarbamoyl]-3-methyl-butyl}-methyl-amino)-acetic acid ethyl ester A mixture of [S-(R*,R*)]-4-methyl-2-methylamino-pentanoic acid [2-(4-benzyloxy-phenyl)-1-tert-butylcarbamoyl-ethyl]-amide (0.55 mmol), diisopropyl ethylamine (1.65 mmol), 2-bromoethyl acetate (0.8 mmol), and anhydrous THF (6 mL) was stirred at 25° C. for 6 hours. The precipitate was filtered off. The reaction mixture was concentrated and purified by column chromatography on silica gel eluting with 10% acetone/methylene chloride to give the titled compound (84% yield).

MS: 540 (M+1 for $C_{31}H_{45}N_3O_5$); sticky solid; TLC: $R_f$0.45 (10% acetone/$CH_2Cl_2$).

Example 97

[S-(R*,R*)]-2-[(3-Hydroxy-butyl)-methyl-amino]-4-methyl-pentanoic acid [2-(4-benzyloxy-phenyl)-1-tert-butylcarbamoyl-ethyl]-amide was made in accordance with the procedure of Example 80 (Step 3), except that 3-hydroxybutyraldehyde was used instead of 4-fluorobenzaldehyde.

MS: 511 (M+1 for $C_{31}H_{47}N_3O_4$); TLC: $R_f$0.25 (5% MeOH/$CH_2Cl_2$).

Example 98

[S-(R*,R*)]-2-[(4-Methoxy-benzyl)-methyl-amino]-4-methyl-pentanoic acid [2-(4-benzyloxy-phenyl)-1-tert-butylcarbamoyl-ethyl]-amide is made in accordance with the procedure of Example 80 (Step 3), except that 4-methoxybenzaldehyde was used instead of 4-fluorobenzaldehyde.

MS: 574 (M+1for $C_{35}H_{47}N_3O_4$); mp 82–84° C.; TLC: $R_f$0.39 (5% MeOH/$CH_2Cl_2$).

Example 99

[S-(R*,R*)]-4-Methyl-2-piperidin-1-yl-pentanoic acid [2-(4-benzyloxy-phenyl)-1-tert-butylcarbamoyl-ethyl]-amide Step 1: (S-4-Methyl-2-piperidin-1-yl-pentanoic acid monohydrobromide was synthesized according to the procedure described in *Acta Poloniae Pharmaceutica—Drug Research,* 1994;51:227–229, which is hereby incorporated by reference in its entirety.

Step 2: (S)-2-Amino-3-(4-benzyloxy-phenyl)-N-tert-butyl-propionamide monohydrochloride (S)-4-Methyl-2-piperidin-1-yl-pentanoic acid monohydrobromide (0.493 g, 1.76 mmol) was mixed with dry DMF (4 mL) under nitrogen atmosphere and cooled to 0° C. in an ice-water bath. To this mixture were added in succession N,N-diisopropylethylamine (1.23 mL, 7.05 mmol ) and solid O-benzotriazol-1-yl-N,N,N',N'-tetramethyluronium hexafluorophosphate (0.667 g, 1.76 mmol ). The resulting reaction mixture was stirred at that temperature for 30 minutes, solid (S)-2-amino-3-(4-benzyloxy-phenyl)-N-tert-butyl-propionamide monohydrochloride (0.639 g, 1.76 mmol) was then added. After stirring for, sequentially, 10 minutes at 0° C. and 45 minutes at ambient temperature, reaction mixture was mixed with 60 mL of diethyl ether; the resulting mixture was successively washed with saturated aqueous $NaHCO_3$ solution (2×60 mL), brine (2×60 mL), and was dried over $Na_2SO_4$. The solution was concentrated in vacuo affording an viscous oil. The crude product was further purified by flash chromatography (40% EtOAc in hexane). Recrystallization from EtOAC/hexanes and subsequent drying under vacuum provided 0.4 g (45%) of the pure titled compound as a white crystalline solid.

MS: 510 (M+ for $C_{31}H_{45}N_3O_3$); mp 109–111° C.

Example 100

[S-(R*,R*)]-2-Ethylamino-4-methyl-pentanoic acid [2-(4-benzyloxy-phenyl)-1-tert-butylcarbamoyl-ethyl]-amide was made in accordance with the procedure of Example 80, except that N-Boc-L-leucine was used instead of N-Boc-N-Me-L-leucine in Step 2 (i), and acetaldehyde was used instead of 4-fluorobenzaldehyde in Step 3.

MS: 469 (M+1 for $C_{28}H_{41}N_3O_3$); sticky solid; TLC: $R_f$ 0.3 (EtOAc).

Example 101

[S-(R*,R*)]-4-Methyl-2-(methyl-pyridin-3-ylmethyl-amino)-pentanoic acid [2-(4-benzyloxy-phenyl)-1-tert-butylcarbamoyl-ethyl]-amide was made in accordance with the procedure of Example 80 (Step 3), except that 3-pyridinecarboxaldehyde was used instead of 4-fluorobenzaldehyde.

MS: 545 (M+1 for $C_{33}H_{44}N_4O_3$); mp 119–120° C.; TLC: $R_f$ 0.30 (5% MeOH/$CH_2Cl_2$).

Example 102

[S-(R*,R*)]-3-(4-Benzyloxy-phenyl)-N-tert-butyl-2-{2-[methyl-(3-methyl-butyl)-amino]-acetylamino}-propionamide was made in accordance with the procedure of Example 80, except that N-Boc-N-methyl-glycine was used instead of N-Boc-N-Me-L-leucine in Step 2 (i), and isovaleraldehyde was used instead of 4-fluorobenzaldehyde in Step 3.

MS: 468 (M+1 for $C_{28}H_{41}N_3O_3$); sticky solid; TLC: $R_f$ 0.57 (10% MeOH/$CH_2Cl_2$).

Example 103

[S-[R*,R*,(RS)]]-2-(sec-Butyl-methyl-amino)-4-methyl-pentanoic acid [2-(4-benzyloxy-phenyl)-1-tert-butylcarbamoyl-ethyl]-amide was made in accordance with the procedure of Example 80 (Step 3), except that 2-butanone was used instead of 4-fluorobenzaldehyde.

MS: 511 (M+1 for $C_{31}H_{47}N_3O_3$); sticky solid, TLC: $R_f$ 0.3 (10% MeOH/$CH_2Cl_2$).

Example 104

(S)-N-[2-(4-Benzyloxy-phenyl)-1-tert-butylcarbamoyl-ethyl]-2-(3-methyl-butylamino)-isobutyramide was made in accordance with the procedure of Example 80, except that N-Boc-alpha-aminoisobutyric acid was used instead of N-Boc-N-Me-L-leucine in Step 2 (i), and isovaleraldehyde was used instead of 4-fluorobenzaldehyde in Step 3.

MS: 483 (M+1 for $C_{29}H_{43}N_3O_3$); sticky solid; TLC: $R_f$ 0.50 (8% MeOH/$CH_2Cl_2$).

Example 105

[S-(R*,R*)]-4-Methyl-2-(3-methyl-butylamino)-pentanoic acid [2-(4-benzyloxy-phenyl)-1-tert-butylcarbamoyl-ethyl]-amide is made in accordance with the procedure of Example 80, except that N-Boc-L-leucine was used instead of N-Boc-N-Me-L-leucine in Step 2 (i) and isovaleraldehyde was used instead of 4-fluorobenzaldehyde in Step 3.

MS: 511 (M+1 for $C_{31}H_{47}N_3O_3$); sticky solid; TLC: $R_f$ 0.18 (1:1 hexane/EtOAc).

Example 106

4-Methyl-2-[methyl-(tetrahydro-pyran-4-yl)-amino]-pentanoic acid [2-(4-benzyloxyphenyl)-1-(1-methoxymethyl-propylcarbamoyl)-ethyl]-amide Step 1: The Preparation of (S)-2-Amino-3-(4-benzyloxyphenyl)-N-(1-methoxymethyl)propyl propionamide Step i: To a mixture of BOC-(OBn)tyrosine (5.0 g, 13.5 mmol), DMF (25 mL), HBTU (5.15 g, 13.5 mmol), and diisopropylethylamine (8.7 g, 67.5 mmol) was added. The resulting solution was treated with 2-amino-1-methoxybutane (1.5 g, 14 mmol), and stirred for 2 hours. The reaction mixture was diluted with 40 mL of ethyl acetate and washed with 1N HCl (2×25 mL), saturated $NaHCO_3$ (2×25 mL) and saturated solution of brine (2×25 mL). The organic layer was collected, dried with $Na_2SO_4$ and evaporated to dryness. The crude residue was crystallized from petroleum ether and toluene to give the title compound (5.98 g, 97%) as a cream-colored solid.

APCI-MS 457.2 [M+1 for $C_{27}H_{38}N_2O_5$].

Step ii: A solution of the product from Step i above (1.0 g, 2.8 mmol) was stirred in a solution of TFA/$CH_2Cl_2$=1/1 (10 mL) for 30 minutes and concentrated to dryness. This crude reaction product was dissolved in $CH_2Cl_2$ (30 mL) and washed sequentially with saturated solution of $NaHCO_3$ and brine. The $CH_2Cl_2$ solution was dried over $NaHCO_3$ and concentrated to dryness to give (S)-2-amino-3-(4-benzyloxyphenyl)-N-(1-methoxymethyl) propyl propionamide (0.98 g, 98%) as a cream-colored solid.

APCI-MS 357.2 [M+1 for $C_{22}H_{30}N_2O_3$].

Step 2: The Preparation of 4-Methyl-2-[methyl-(tetrahydro-pyran-4-yl)-amino]-pentanoic acid [2-(4-benzyloxyphenyl)-1-(1-methoxymethyl-propylcarbamoyl)-ethyl]-amide A solution of (S)-4-methyl-2-[methyl-(tetrahydro-pyran-4-yl)-amino]-pentanoic acid (0.13 g, 0.56 mmol) in 10 mL of DMF at 0° C. was treated with HBTU (0.21 g, 0.56 mmol) and diisopropylethylamine (0.36 g, 2.80 mmol). The reaction mixture was stirred for 30 minutes at 0° C. A solution of (S)-2-amino-3-(4-benzyloxyphenyl)-N-(1-methoxymethyl)propyl propionamide (0.21 g, 0.56 mmol) in 10 mL of DMF was added to the reaction mixture. The reaction mixture was allowed to reach the room temperature and was stirred for another 30 minutes. The reaction mixture was diluted with 20 mL of ethyl acetate, washed sequentially with 1N HCl (2×10 mL), saturated aqueous $NaHCO_3$ (2×10 mL) and brine (2×10 mL). The organic layer was separated, dried with $Na_2SO_4$ and evaporated to dryness. The crude residue was purified by chromatography ($SiO_2$, 1:1 ethyl acetate/hexane). The purified product was then dissolved in minimum volume of diethylether and ethereal solution of HCl was added dropwise. The solid HCl-salt separated out, washed several times with diethylether to get 0.21 g (62%) of fine cream powder; mp 106–109° C.

Analysis calculated for $C_{33}H_{49}N_3O_5 \cdot 0.58H_2O$ HCl:
C, 64.48; H, 8.39; N, 6.84; $H_2O$, 1.70.
Found: C, 64.86; H, 8.51; N, 6.82; $H_2O$, 1.80.

Example 107

4-Methyl-2-[methyl-(3-methylbutyl)-amino]-pentanoic acid [2-(4-benzyloxyphenyl)-1-(1-methoxymethyl-propylcarbamoyl)-ethyl]-amide To a solution of (S)-4-methyl-2-[methyl-(3-methylbutyl)-amino]-pentanoic acid (0.12 g, 0.56 mmol) in 10 mL of DMF was added HBTU (0.21 g, 0.56 mmol) and diisopropylethylamine (0.36 g, 2.80 mmol). The mixture was stirred for 30 minutes at 0° C. A solution of (S)-2-amino-3-(4-benzyloxyphenyl)-N-(1-methoxymethyl)propyl propionamide (0.21 g, 0.56 mmol) in 10 mL of DMF was added to the reaction mixture. The reaction mixture was allowed to reach the room temperature and was stirred for another 30 minutes. The mixture was diluted with 20 mL of ethylacetate, washed with 1N HCl (2×10 mL), saturated NaHCO$_3$ (2×10 mL) and saturated solution of brine (2×10 mL). The organic layer was separated, dried with Na$_2$SO$_4$ and evaporated to dryness. The crude was purified by chromatography (SiO$_2$1:1 hexane/ethyl acetate). The purified product was then dissolved in minimum volume of diethylether, and ethereal solution of HCl was added dropwise. The solid which formed was collected and washed several times with diethylether to give the title compound (0.25 g, 76%) as a cream-colored powder; mp 83–85° C.

Analysis calculated for C$_{33}$H$_{51}$N$_3$O$_4$0.32H$_2$O HCl:
C, 66.50; H, 8.90; N, 7.05; H$_2$O, 0.97.
Found: C, 66.32; H, 9.01; N, 6.93; H$_2$O, 0.99.

Example 108

2-(Isopropyl-methyl-amino)4-methyl-pentanioc acid [2-(4-benzyloxyphenyl)-1-(1-methoxymethyl-propylcarbamoyl)-ethyl]-amide A solution of (S)-2-(isopropyl-methyl-amino)-4-methyl-pentanioc acid (0.11 g, 0.56 mmol) in 10 mL of DMF was treated with HBTU (0.21 g, 0.56 mmol) and diisopropylethylamine (0.36 g, 2.80 mmol). The mixture was stirred for 30 minutes at 0° C. A solution of (S)-2-amino-3-(4-benzyloxyphenyl)-N-(1-methoxymethyl)propyl propionamide (0.21 g, 0.56 mmol) in 10 mL of DMF was added to the reaction mixture. The reaction mixture was allowed to reach the room temperature and was stirred for another 30 minutes. The reaction mixture was diluted with 20 mL of ethyl acetate, washed with 1N HCl (2×10 mL), saturated NaHCO$_3$ (2×10 mL) and saturated solution of brine(2×10 mL). The organic layer was separated, dried with Na$_2$SO$_4$ and evaporated to dryness. The crude was purified by chromatography (silica gel, 1:1 hexane/ethyl acetate). The purified product was then dissolved in minimum volume of diethylether and an ethereal solution of HCl was added dropwise. The solid which formed was washed several times with diethylether. The solid was dissolved in methanol and treated with activated charcoal, filtered and concentrated. The solid was crystallized from methanol-ether to give the title compound (0.13 g, 40%) as a white powder mp 101–105° C.

APCI MS 526.3 [M+1 for C$_{31}$H$_{47}$N$_3$O$_4$].

Example 109

2-[(4-tert-butyl-benzyl)-methyl-amino]-4-methyl-pentanoic acid [2-(4-benzyloxyphenyl)-1-(1-methoxymethyl-propylcarbamoyl)-ethyl]-amide To a solution of (S)-2-[(4-tert-butyl-benzyl)-methyl-amino]-4-methyl-pentanoic acid (0.33 g, 1.12 mmol) in 15 mL of DMF was added HBTU (0.43 g, 1.12 mmol) and diisopropylethylamine (0.72 g, 5.6 mmol). The mixture was stirred for 30 minutes at 0° C. A solution of (S)-2-amino-3-(4-benzyloxyphenyl)-N-(1-methoxymethyl)propyl propionamide (0.4 g, 1.12 mmol) in 15 mL of DMF was added to the reaction mixture. The reaction mixture was allowed to reach the room temperature and was stirred for another 30 minutes. The mixture was diluted with 40 mL of ethylacetate, washed with 1N HCl (2×10 mL), saturated NaHCO$_3$ (2×10 mL) and saturated solution of brine (2×10 mL). The organic layer was separated, dried with Na$_2$SO$_4$ and evaporated to dryness. The crude was purified by chromatography (SiO$_2$, 8:2 hexane/ethyl acetate). The purified product was dissolved in minimum volume of diethylether and an ethereal solution of HCl was added dropwise. The solid which formed was washed several times with diethylether to give the title compound (0.28 g, 37%) as a cream-colored powder mp 118–120° C.

Analysis calculated for C$_{39}$H$_{55}$N$_3$O$_4$.HCl:
C, 70.30; H, 8.47; N, 6.31; Cl$^-$, 5.32.
Found: C, 69.94; H, 8.46; N, 6.16; Cl$^-$, 5.55.

Example 110

2[(4-Dimethylamino-benzyl)-methyl-amino]-4-methyl-pentanoic acid [2-(4-benzyloxyphenyl)-1-(1-methoxymethyl-propylcarbamoyl)-ethyl]-amide Step 1: The Preparation of 2-[(4-Dimethylamino-benzyl)-methyl-amino]-4-methyl-pentanoic-acid To a solution of N-methyl leucine (8.0 g, 55.1 mmol) and 4-N,N-dimethyl-benzaldehyde (8.4 g, 56.0 mmol) in 80 mL of dry THF was added titanium (IV) isopropoxide (15.7 g, 55.1 mmol). The mixture was stirred at room temperature for 4 hours and was diluted with 20 mL of absolute ethanol. NaBH$_4$ (3.0 g, 80.0 mmol) was added slowly to the mixture. The resulting mixture was stirred overnight. The reaction mixture was quenched with 40 mL of water and was filtered to remove an inorganic precipitate. Evaporation of the crude filtrate gave a slurry which was dissolved in minimum volume of MeOH and was filtered to remove the last traces of inorganic salt. The filtrated was evaporated to dryness, dissolved in minimum volume of 0.1N NaOH and washed with diethyl ether (4×40 mL) followed by ethyl acetate (2×40 mL). The aqueous phase was acidified to pH 6 with 1N HCl, saturated with NaCl, and extracted with ethyl acetate (6×40 mL). The combined organic extracts were dried over anhydrous Na$_2$SO$_4$ and concentrated to give the product (7.6 g, 49%) as a white solid; mp 176–180° C.

APCI MS 277.3 [M+1 for C$_{16}$H$_{26}$N$_2$O$_2$].

Step 2:2-[(4-Dimethylamino-benzyl)-methyl-amino]-4-methyl-pentanoic acid [2-(4-benzyloxyphenyl)-1-(1-methoxymethyl-propylcarbamoyl)-ethyl]-amide A solution of (S)-2-[(4-dimethylamino-benzyl)-methyl-amino]-4-methyl-pentanoic acid (0.31 g, 1.12 mmol) in 15 mL of DMF was treated with HBTU (0.425 g, 1.12 mmol) and diisopropylethylamine (0.723 g, 5.6 mmol). The reaction mixture was stirred for 30 minutes at 0° C. A solution of (S)-2-amino-3-(4-benzyloxyphenyl)-N-(1-methoxymethyl)propyl propionamide (0.40 g, 1.12 mmol) in 15 mL of DMF was added to the reaction mixture. The reaction mixture was allowed to reach the room temperature and was stirred for another 30 minutes. The reaction mixture was diluted with 40 mL of ethyl acetate, washed with 1N HCl (2×10 mL), saturated NaHCO$_3$ (2×10 mL) and brine (2×10 mL). The organic layer was collected, dried with Na$_2$SO$_4$ and evaporated to dryness. The crude residue was purified by chromatography (silica gel, 6:4 hexane/ethyl acetate). The purified product was crystallized from diethyl ether and petroleum ether to give the title compound (0.22 g, 30%) as a white powder; mp 109–112° C.

Analysis calculated for C$_{37}$H$_{52}$N$_4$O$_4$:
C, 72.05; H, 8.50; N, 9.08.
Found: C, 71.59; H, 8.44; N, 8.94.

Example 111

4-Methyl-2-[methyl-tetrahydropyran-4-yl)-amino]-pentanoic acid [2-(4-benzyoxyphenyl)-1-(1-propyl-piperidin-3-ylcarbamoyl)-ethyl]-amide Step 1: A mixture of BOC-(OBn)tyrosine (5 g, 13.5 mmol), DMF (25 mL), HBTU (5.15 g, 13.5 mmol), and diisopropylethylamine (8.7 g, 67.5 mmol) was treated with 3-1-propyl-piperidinamine, (2.0 g, 14.0 mmol), and was stirred for 2 hours. The mixture was diluted with 40 mL of ethyl acetate, washed with 1N HCl (2×25 mL), saturated NaHCO$_3$ (2×25 mL), and saturated solution of brine (2×25 mL). The organic layer was separated, dried with Na$_2$SO$_4$ and evaporated to dryness. The crude residue was crystallized from petroleum ether and toluene to give the product (5.98 g, 89%) as a brown solid.

APCI MS 496.4 [M+1 for C$_{29}$H$_{41}$N$_3$O$_4$].

Step 2: 2-Amino-3-(4-benzyloxyphenyl)-N-(1-propyl-piperidin-3-yl)propionamide

A solution of the product from Step 1 above (0.625 g, 1.26 mmol) was stirred in a solution of TFA/CH$_2$Cl$_2$1:1 (10 mL) for 30 minutes and concentrated to dryness. The crude reaction product was dissolved in CH$_2$Cl$_2$ (30 mL) then washed with saturated solution of NaHCO$_3$ and brine. The organic phase was further dried over Na$_2$SO$_4$ and concentrated to dryness to yield the product (0.50 g, 99%) as a brown solid.

APCI MS 396.4 [M+1 or C$_{24}$H$_{33}$N$_3$O$_2$].

Step 3: 4-Methyl-2-[methyl-tetrahydropyran-4-yl)-amino]-pentanoic acid [2-(4-benzyloxyphenyl)-1-(1-propyl-piperidin-3-ylcarbamoyl)-ethyl]-amide To a solution of the product from Step 2 above (0.3 g, 1.26 mmol) in 15 mL of DMF was added HBTU (0.478 g, 1.26 mmol) and diisopropylethylamine (0.815 g, 6.3 mmol). The mixture was stirred for 30 minutes at 0° C. A solution of (S)-4-methyl-2-[methyl-(tetrahydro-pyran-4-yl)-amino]-pentanoic acid (0.50 g, 1.26 mmol) in 15 mL of DMF was added to the reaction mixture. The reaction mixture was allowed to reach the room temperature and was stirred for another 30 minutes. The mixture was diluted with 20 mL of ethyl acetate, washed with 1N HCl (2×0 mL), saturated NaHCO$_3$ (2×10 mL) and saturated solution of brine (2×10 mL). The organic layer was collected, dried with Na$_2$SO$_4$ and evaporated to dryness. The crude was purified by chromatography (silica gel, 1:1 hexane/ethyl with 1% methanol and 1% NH$_4$OH). The purified product was then dissolved in minimum volume of diethylether and ethereal solution of HCl was added dropwise. The solid which formed was collected and washed several times with diethylether. The solid was dissolved in methanol and treated with activated charcoal, filtered, and evaporated. The residue was crystallized from methanol-ether to give the title compound (0.21 g, 26%) as a cream-colored powder; mp 135–136° C.

APCI MS 607.4 [M+1 for C$_{36}$H$_{54}$N$_4$O$_4$].

Example 112

4-Methyl-2-[methyl-(3-methyl-butyl-amino]-pentanoic acid [2-(4-benzyloxyphenyl)-1-(1-propyl-piperidin-3-ylcarbamoyl)-ethyl]-amide To a solution of (S)-4-methyl-2-[methyl-(3-methylbutyl)-amino]-pentanoic acid (0.27 g, 1.26 mmol) in 15 mL of DMF was added HBTU (0.48 g, 1.26 mmol) and diisopropylethylamine (0.82 g, 6.3 mmol). The mixture was stirred for 30 minutes at 0° C. A solution of 2-amino-3-(4-benzyloxyphenyl)-N-(1-propyl-piperidin-3-yl) propionamide (0.50 g, 1.26 mmol) in 15 mL of DMF was added to the reaction mixture. The reaction mixture was allowed to reach the room temperature and was stirred for another 30 minutes. The mixture was diluted with 20 mL of ethyl acetate, washed with 1N HCl (2×10 mL), saturated NaHCO$_3$ (2×10 mL) and saturated solution of brine (2×10 mL). The organic layer was separated, dried with Na$_2$SO$_4$ and evaporated to dryness. The crude residue was purified by chromatography (silica gel, hexane/ethyl acetate containing 1% methanol and 1% NH$_4$OH). The purified product was then dissolved in minimum volume of diethylether, and an ethereal solution of HCl was added dropwise. The solid which formed was washed with diethylether. The solid was dissolved in methanol and treated with activated charcoal, filtered, and evaporated. The solid was crystallized from methanol-ether to give the title compound (0.31 g, 39%) as a white powder; mp 120–124° C.

APCI MS 593.5 [M+1 for C$_{45}$H$_{59}$N$_5$O$_4$].

Example 113

2-(Isopropyl-methyl-amino)-methyl-pentanoic acid [2-(4-benzyloxyphenyl) -1-(1-propyl-piperidin-3-ylcarbamoyl)-ethyl]-amide:

To a solution of (S)-2-(Isopropyl-methyl-amino)4-methyl-pentanioc acid (0.24 g, 1.26 mmol) in 15 mL of DMF was added HBTU (0.48 g, 1.26 mmol) and diisopropylethylamine (0.82 g, 6.3 mmol). The mixture was stirred for 30 minutes at 0° C. A solution of 2-amino-3-(4-benzyloxyphenyl)-N-(1-propyl-piperidin-3-yl) propionamide (0.50 g, 1.26 mmol) in 15 mL of DMF was added to the reaction mixture. The reaction mixture was allowed to reach the room temperature and was stirred for another 30 minutes. The mixture was diluted with 20 mL of ethyl acetate, washed with 1N HCl (2×10 mL), saturated NaHCO$_3$ (2×10 mL) and saturated solution of brine (2×10 mL). The organic layer was separated, dried with Na$_2$SO$_4$ and evaporated to dryness. The crude residue was purified by chromatography (silica gel, 1:1 hexane/ethyl acetate containing 1% methanol and 1% NH$_4$OH). The purified product was then dissolved in minimum volume of diethylether and ethereal solution of HCl was added dropwise. The solid which formed was washed several times with diethylether. The solid was dissolved in methanol and treated with activated charcoal, filtered, and evaporated. The residue was crystallized from methanol-ether to give the title compound (0.3 g, 40%) as a white powder; mp 118–122° C.

APCI MS 565.5 [M+1 for C$_{34}$H$_{52}$N$_4$O$_3$].

Example 114

2-[(4-tertButyl-benzyl-)-methyl-amino]-4-methyl-pentanoic acid [2-(4-benzyloxyphenyl)-1-(1-propyl-piperidin-3-ylcarbamoyl)-ethyl]-amide To a solution of (S)-2-[(4-tert-butyl-benzyl)-methyl-amino]-4-methyl-pentanoic acid (0.3 g, 1.01 mmol) in 15 mL of DMF was added HBTU (0.38 g, 1.01 mmol) and diisopropylethylamine (0.65 g, 5.05 mmol). The mixture was stirred for 30 minutes at 0° C. A solution of 2-amino-3-(4-benzyloxyphenyl)-N-(1-propyl-piperidin-3-yl) propionamide (0.4 g, 1.01 mmol) in 15 mL of DMF was added to the reaction mixture. The reaction mixture was allowed to warm to room temperature and was stirred for another 30 minutes. The mixture was diluted with 20 mL of ethyl acetate, washed with 1N HCl (2×10 mL), saturated NaHCO$_3$ (2×10 mL) and saturated solution of brine (2×10 mL). The organic layer was separated, dried with Na$_2$SO$_4$ and evaporated to dryness. The crude residue was purified by chromatography (silica gel, 7:3 hexane/ethyl acetate). The purified product was dissolved in minimum volume of diethylether and an ethereal solution of HCl was added dropwise. The solid which formed was washed several times with diethylether. The solid was dissolved in methanol and treated with activated charcoal, filtered, and evaporated. The

Example 115

2-[(4-Dimethylamino-benzyl)-methyl-amino]-4-methyl-pentanoic acid [2-(4-benzyloxy phenyl)-1-(1-propyl-piperidin-3-ylcarbamoyl)-ethyl]-amide To a solution of (S)-2-[(4-dimethylamino-benzyl)-methyl-amino]-4-methyl-pentanoic acid (0.28 g, 1.01 mmol) in 15 mL of DMF was added HBTU (0.38 g, 1.01 mmol) and diisopropylethylamine (0.65 g, 5.05 mmol). The mixture was stirred for 30 minutes at 0° C. A solution of 2-amino-3-(4-benzyloxyphenyl)-N-(1-propyl-piperidin-3-yl)propionamide (0.40 g, 1.01 mmol) in 15 mL of DMF was added to the reaction mixture. The reaction mixture was allowed to reach the room temperature and was stirred for another 30 minutes. The mixture was diluted with 40 mL of ethyl acetate, washed with 1N HCl (2×10 mL), saturated $NaHCO_3$ (2×10 mL) and saturated solution of brine (2×10 mL). The organic layer was separated, dried with $Na_2SO_4$ and evaporated to dryness. The crude residue was purified by chromatography (silica gel, 6:4 hexane/ethyl acetate). The purified product was crystallized from methylene chloride and petroleum ether to give the title compound (0.34 g, 49%) as a white powder; mp 131–133° C.

Analysis calculated for $C_{40}H_{57}N_5O_3$:
C, 73.25; H, 8.76; N, 10.68.
Found: C, 73.08; H, 8.85; N, 10.59.

Example 116

[S-(R*,R*)]4-Methyl-2-[methyl-(3-methylbutyl)-amino]-pentanoic acid [2-(4-benzyloxy-phenyl)-1-(2-hydroxy-1,1-dimethyl-ethylcarbamoyl)-ethyl]-amide A suspension of N-(2-methylbutyl)-N-methyl-leucine-tyrosine(OBn)-Kaiser oxime resin (Example 57, IIc) in $CH_2Cl_2$ was treated with 1.5 equivalents of 2-hydroxy-1,1-dimethylethylamine. The suspension was shaken for 48 hours. After the reaction was completed, additional $CH_2Cl_2$ and 1 equivalent of polymer supported isocyanate was added. After the suspension was shaken for 48 hours, the resin was filtered off, and the solvent was evaporated to yield the title product.

APCI MS 538.5 (M+1); HPLC retention time: 26.65 minutes.

Example 117

[S-(R*,R*)]-4-Methyl-2-[methyl-(3-methylbutyl)-amino]-pentanoic acid [2-(4-benzyloxy-phenyl)-1-(2-piperidin-1-yl-ethylcarbamoyl)-ethyl]-amide A suspension of N-(2-methylbutyl)-N-methyl-leucine-tyrosine(OBn)-Kaiser oxime resin (Example 57, IIc) in $CH_2Cl_2$ was treated with 1.5 equivalents of 2-piperdin-1-ylethylamine. The suspension was shaken for 48 hours. After the reaction was completed, additional $CH_2Cl_2$ and 1 equivalent of polymer supported isocyanate was added. After the suspension was shaken for 48 hours, the resin was filtered off, and the solvent was evaporated to yield the title product.

APCI MS 579.3 (M+1); HPLC retention time: 19.62 minutes.

Example 118

[S-(R*,R*)]-4-Methyl-2-[methyl-(3-methyl-butyl)-amino]-pentanoic acid {2-(4-benzyloxy-phenyl)-1-[3-(2-oxo-pyrrolidin-1-yl)-propylcarbamoyl]-ethyl}-amide A suspension of N-(2-methylbutyl)-N-methyl-leucine-tyrosine(OBn)-Kaiser oxime resin (Example 57, IIc) in $CH_2Cl_2$ was treated with 1.5 equivalents of 1-(3-aminopropylamino)-pyrrolidinone. The suspension was shaken for 48 hours. After the reaction was completed, additional $CH_2Cl_2$ and 1 equivalent of polymer supported isocyanate was added. After the suspension was shaken for 48 hours, the resin was filtered off, and the solvent was evaporated to yield the title product.

APCI MS 593.3 (M+1); HPLC retention time: 25.61 minutes.

Example 119

[S-(R*,R*)]-4-Methyl-2-morpholin-4-yl-pentanoic acid [2-(4-benzyloxy-phenyl)-1-(2-morpholin-4-yl-ethylcarbamoyl)-ethyl]-amide was prepared in accordance with the procedure of Example 68 (Step 3), except 2-morpholin4-yl-ethylamine was used instead of $N^1$-benzyl-ethane-1,2-diamine.

APCI MS 567.3 (M+1); HPLC retention time: 19.00 minutes.

Example 120

[S-(R*,R*)]-4-Methyl-2-morpholin-4yl-pentanoic acid [2-(4-benzyloxy-phenyl)-1-(2-pyridin-2-yl-ethylcarbamoyl)-ethyl]-amide was prepared in accordance with the procedure of Example 68 (Step 3), except 2-(2-aminoethyl)pyridine was used instead of $N^1$-benzyl-ethane-1,2-diamine.

APCI MS 559.3 (M+1); HPLC retention time: 19.00 minutes.

Example 121

[S-(R*,R*)]-4-Methyl-2-morpholin-4-yl-pentanoic acid [2-(4-benzyloxy-phenyl)-1-(3-imidazol-1-yl-propylcarbamoyl)-ethyl]-amide was prepared in accordance with the procedure of Example 68 (Step 3), except histamine was used instead of $N^1$-benzyl-ethane-1,2-diamine.

APCI MS 562.3 (M+1); HPLC retention time: 18.90minutes.

Example 122

[S-(R*,R*)]-4-Methyl-2-morpholin-4-yl-pentanoic acid [2-(4-benzyloxy-phenyl)-1-(2-thiomorpholin-4-yl-ethylcarbamoyl)-ethyl]-amide was prepared in accordance with the procedure of Example 68 (Step 3), except thiomorpholine was used instead of $N^1$-benzyl-ethane-1,2-diamine.

APCI MS 540.2 (M+1); HPLC retention time: 25.65 minutes

Example 123

[S-(R*,R*)]-4-Methyl-2-morpholin-4-yl-pentanoic acid [2-(4-benzyloxy-phenyl)-1-(2-hydroxy-1,1-dimethyl-ethylcarbamoyl)-ethyl]-amide was prepared in accordance with the procedure of Example 68 (Step 3), except 1,1-dimethyl-2-hydroxy-ethylamine was used instead of $N^1$-benzyl-ethane-1,2-diamine.

APCI MS 526.3 (M+1); HPLC retention time: 22.65 minutes.

Example 124

[S-(R*,R*)]-4-Methyl-2-morpholin-4-yl-pentanoic acid [2-(4-benzyloxy-phenyl)-1-(1,1-bis-hydroxymethyl-propylcarbamoyl)-ethyl]-amide was prepared in accordance with the procedure of Example 68 (Step 3), except 2-amino-2-methyl-propane-1,3-diol was used instead of N$^1$-benzyl-ethane-1,2-diamine.

APCI MS 556.3 (M+1); HPLC retention time: 21.55 minutes.

Example 125

[S-(R*,R*)]-4-Methyl-2-morpholin-4-yl-pentanoic acid [2-(4-benzyloxy-phenyl)-1-(2-pyrrolidin-1-yl-ethylcarbamoyl)-ethyl]-amide was prepared in accordance with the procedure of Example 68 (Step 3), except 2-pyrrolidin-1-yl-ethylamine was used instead of N$^1$-benzyl-ethane-1,2-diamine.

APCI MS 551.3 (M+1); HPLC retention time: 19.34 minutes.

Example 126

[S-(R*,R*)]4-Methyl-2-morpholin-4-yl-pentanoic acid [2-(4-benzyloxy-phenyl)-1-(4-hydroxypiperidinylcarbamoyl)-ethyl]-amide was prepared in accordance with the procedure of Example 68 (Step 3), except piperidine-4-ol was used instead of N$^1$-benzyl-ethane-1,2-diamine.

APCI MS 538.3 (M+1); HPLC retention time: 20.96 minutes.

Example 127

[S-(R*,R*)]-4-Methyl-2-(tetrahydropyran-4-yl-amino)-pentanoic acid [2-(4-benzyloxy-phenyl)-1-(2-morpholin4-yl-ethylcarbamoyl)-ethyl]-amide was prepared in accordance with the procedure of Example 71 (Step 3), except 2-morpholin-4-yl-ethylamine was used instead of N$^1$-benzyl-ethane-1,2-diamine.

APCI MS 595.3 (M+1); HPLC retention time: 19.40 minutes.

Example 128

[S-(R*,R*)]-4-Methyl-2-(tetrahydropyran-4-yl-amino)-pentanoic acid [2-(4-benzyloxy-phenyl)-1-(-(2-pyridin-2-yl-ethylcarbamoyl)-ethyl]-amide was prepared in accordance with the procedure of Example 71 (Step 3), except 2-(2-aminoethyl)pyridine was used instead of N$^1$-benzyl-ethane-1,2-diamine.

APCI MS 587.3 (M+1); HPLC retention time: 19.36 minutes.

Example 129

[S-(R*,R*)]-4-Methyl-2-(tetrahydropyran-4-yl-amino)-pentanoic acid [2-(4-benzyloxy-phenyl)-1-(3-imidazol-1-yl-propylcarbamoyl)-ethyl]-amide was prepared in accordance with the procedure of Example 71 (Step 3), except histamine was used instead of N$^1$-benzyl-ethane-1,2-diamine.

APCI MS 590.3 (M+1); HPLC retention time: 19.16 minutes.

Example 130

[S-(R*,R*)]-4-Methyl-2-(tetrahydropyran-4-yl-amino)-pentanoic acid [2-(4-benzyloxy-phenyl)-1-(2-pyrrolidine-1-yl-ethylcarbamoyl]-amide was prepared in accordance with the procedure of Example 71 (Step 3), except 2-pyrrolidine-1-yl-ethylamine was used instead of N$^1$-benzyl-ethane-1,2-diamine.

APCI MS 579.4 (M+1); HPLC retention time: 19.62 minutes.

Example 131

[S-(R*,R*)]-4-Methyl-2-(tetrahydropyran-4-yl-amino)-pentanoic acid [2-(4-benzyloxy-phenyl)-1-(4-hydroxy-piperinylcarbamoyl)-amide was prepared in accordance with the procedure of Example 71 (Step 3), except 2-4-hydroxypiperidine was used instead of N$^1$-benzyl-ethane-1,2-diamine APCI MS 566.3 (M+1); HPLC retention time: 21.35 minutes.

Example 132

[S-(R*,R*)]-2-Dimethylamino-4-methyl-pentanoic acid [2-(4-benzyloxy-phenyl)-1-(2-morpholin-4-yl-ethylcarbamoyl)-ethyl]-amide was prepared in accordance with Example 57 (Step 3) except [S-(R*,R*)]-2-{2-dimethylamino-4-methyl-penanoylamino}-3-(4-benzyloxy-phenyl)-propionic acid Kaiser oxime resin ester was used instead of IIc (Step 3).

APCI MS 525.4 (M+1): HPLC retention time: 18.83 minutes.

Example 133

[S-(R*,R*)]-2-Dimethylamino-4-methyl-pentanoic acid [2-(4-benzyloxy-phenyl)-1-(2-(2-aminoethyl)pyridine carbamoyl)-ethyl]-amide was prepared in accordance with the procedure of Example 132 (Step 3), except 2-(2-aminoethyl)pyridine was used instead of 2-morpholin-4-yl-ethylamine.

HPLC retention time: 18.81 minutes.

Example 134

[S-(R*,R*)]-2-Dimethylamino-4-methyl-pentanoic acid [2-(4-benzyloxy-phenyl)-1-(3-imidazol-1-yl-propylcarbamoyl)-ethyl]-amide was prepared in accordance with the procedure of Example 132 (Step 3), except histamine was used instead of 2-morpholin-4-yl-ethylamine.

APCI MS 520.4 (M+1); HPLC retention time: 18.62 minutes.

Example 135

[S-(R*,R*)]-2-Dimethylamino-4-methyl-pentanoic acid [2-(4-benzyloxy-phenyl)-1-(thiomorpholinecarbamoyl)-ethyl]-amide was prepared in accordance with the procedure of Example 132 (Step 3), except thiomorpholine was used instead of 2-morpholin-4-yl-ethylamine.

APCI MS 498.3 (M+1); HPLC retention time: 25.61 minutes.

Example 136

[S-(R*,R*)]-2-Dimethylamino-4-methyl-pentanoic acid [2-(4-benzyloxy-phenyl)-1-(2-aminopropan-1-ol carbamoyl)-ethyl]-amide was prepared in accordance with the procedure of Example 133 (Step 3), except 2-aminopropan-1-ol was used instead of 2-morpholin-4-yl-ethylamine.

APCI MS 484.4 (M+1); HPLC retention time: 22.62 minutes.

Example 137

[S-(R*,R*)]-2-Dimethylamino-4-methyl-pentanoic acid [2-(4-benzyloxy-phenyl)-1-(2-hydroxymethylbutan-1-ol)-ethyl]-amide was prepared in accordance with the procedure of Example 132 (Step 3), except 2-hydroxymethylbutan-1-ol was used instead of 2-morpholin-4-yl-ethylamine.

APCI MS 498.4 (M+1); HPLC retention time: 21.38 minutes.

Example 138

[S-(R*,R*)]-2-Dimethylamino-4-methyl-pentanoic acid [2-(4-benzyloxy-phenyl)-1-(1-methoxymethyl-propylcarbamoyl)-ethyl]-amide was prepared in accordance with the procedure of Example 132 (Step 3), except 1-methoxymethyl-propylamine was used instead of 2-morpholin-4-yl-ethylamine.

APCI MS 498.4 (M+1); HPLC retention time: 24.88 minutes.

Example 139

[S-(R*,R*)]-2-Dimethylamino-4-methyl-pentanoic acid [2-(4-benzyloxy-phenyl)-1-(2-pyrrolidin-1-yl-ethylcarbamoyl)-ethyl]-amide was prepared in accordance with the procedure of Example 132 (Step 3), except 2-pyrrolidin-1-yl-ethylamine was used instead of 2-morpholin-4-yl-ethylamine.

APCI MS 509.4 (M+1); HPLC retention time: 19.14 minutes.

Example 140

[S-(R*,R*)]-2-Dimethylamino-4-methyl-pentanoic acid {2-(4-benzyloxy-phenyl)-1-[2-(2-hydroxy-ethylamino)-ethylcarbamoyl]-ethyl}-amide was prepared in accordance with the procedure of Example 132 (Step 3), except 2-(2-aminoethylamino)-ethanol was used instead of 2-morpholin-4-yl-ethylamine.

APCI MS 499.3 (M+1); HPLC retention time: 18.44 minutes.

Biological Activity

The compounds of the present invention exhibit valuable biological properties because of their ability to block calcium flux through N-type voltage-gated calcium channels. To measure interaction at the N-type $Ca^{2+}$ channel and calcium flux inhibition, the effects of the compounds of the present invention were measured in the assays described below.

Measurement of N-type $Ca^{2+}$ Channel Blocking Potencies of Compounds in IMR-32 Cells Using the Fluorescent $Ca^{2+}$ Indicator Indo-1

IMR-32 cells are a human tumoral cell line of neural origin. The IMR-32 cell line has been shown to contain both N- and L-type voltage sensitive calcium channels. Calcium flux into these cells may be induced by stimulation with elevated potassium concentrations. The L-channel component of calcium flux may be blocked by adding 5 $\mu$M nitrendipine. The remaining component of calcium entry into the IMR-32 cells is due to calcium flux through N-type calcium channels. Intracellular calcium concentrations are measured using the fluorescent calcium indicator Indo-1. The effect of drug concentration on calcium uptake is studied.

Methods

The IMR-32 cell line was obtained from the American Type Culture Collection (Rockville, Md.). Cells were grown in Eagle's Minimum Essential Medium with Earle's salts supplemented with 10% fetal bovine serum, 2 mM L-Gln and antibiotic/antimycotic mixture (Gibco). At approximately 80% confluency, differentiation was induced by the addition of 1 mM dibutyryl cAMP and 2.5 $\mu$M bromodeoxyuridine to the medium. After 7 to 13 days of differentiation, cells were detached using 0.5 mM EDTA and loaded with 5 $\mu$M Indo-1 acetoxymethyl ester (Molecular Probes, Eugene, Oreg.) at 30° C. for 45 minutes. Loaded cells were washed twice, resuspended (~$10^7$ cells/mL) in assay buffer (10 mM HEPES/Tris pH 7.4 in Hank's Balanced Salt Solution without bicarbonate or phenol red containing 0.5% bovine serum albumin) and kept on ice until use. Fluorescence measurements were carried out in a Photon Technology International (PTI, South Brunswick, N.J.) Model RF-F3004 spectrofluorometer with dual emission monochromators using excitation at 350 nm and emission at 400 and 490 nm. The instrument was equipped with a thermostated cuvette holder with stirring capabilities as well as with a computer-controlled pump which allowed for reagent addition during measurement. Instrument control and data collection was done by PTI's OSCAR software running on an IBM compatible computer. Different concentrations of the test compounds (60 $\mu$L in dimethyl sulfoxide) were added to 5.94 mL of assay buffer containing approximately 3×$10^6$ loaded cells, and 5 $\mu$M nitrendipine (in 30 $\mu$L EtOH) to block L-type $Ca^{2+}$ channels. Samples were incubated for 10 minutes at 30° C. and then aliquoted into three 10×10 mm disposable acrylic cuvettes. Emission signals at 400 and 490 nm were acquired from each cuvette at 30° C. for 50 seconds. At 20 seconds after the start of reading, cells were depolarized by the addition of 160 $\mu$L of stimulation solution (1 M KCl, 68 mM $CaCl_2$) to the cuvette via the computer-controlled pump. Ratio of dual emission signals (400 nm/ 490 nm), which is proportional to intracellular $Ca^{2+}$ concentration, was plotted against time, and the difference between maximal response after stimulation and basal value (before stimulation) was determined. Values obtained in this way were plotted as a function of drug concentration. $IC_{50}$ values of test compounds were calculated by fitting a four-parameter logistic function to the data using the least squares method.

In Vivo Biological Protocol

A compound of the present invention was dissolved in water using 10% (weight/volume) Emulphor (GAF Corp., Wayne, N.J.) surfactant. Substances were administered by intravenous injection into the retro-orbital venous sinus. All testing was performed 15 minutes or 45 minutes after drug injection. All the male mice, 3–4 weeks old were obtained from Jackson Laboratories Bar Harbour, Me. Immediately before anticonvulsant testing, mice were placed upon a wire mesh, 4 inches square suspended from a steel rod. The square was slowly inverted through 180 degrees and mice observed for 30 seconds. Any mouse falling from the wire mesh was scored as ataxia.

Mice were placed into an enclosed acrylic plastic chamber (21 cm height, approximately 30 cm diameter) with a high-frequency speaker (4 cm diameter) in the center of the top lid. An audio signal generator (Protek model B-810) was used to produce a continuous sinusoidal tone that was swept linearly in frequency between 8 kHz and 16 kHz once each 10 msec. The average sound pressure level (SPL) during stimulation was approximately 100 dB at the floor of the chamber. Mice were placed within the chamber and allowed to acclimatize for 1 minute. DBA/2 mice in the vehicle-treated group responded to the sound stimulus (applied until tonic extension occurred, or for a maximum of 60 sec) with a characteristic seizure sequence consisting of wild running followed by clonic seizures, and later by tonic extension, and finally by respiratory arrest and death in 80% or more of the mice. In vehicle-treated mice, the entire sequence of seizures to respiratory arrest lasts approximately 15–20 seconds.

The incidence of all the seizure phases in the drug-treated and vehicle-treated mice was recorded, and the occurrence of tonic seizures were used for calculating anticonvulsant $ED_{50}$ values by probit analysis. Mice were used only once for testing at each time and dose point. Results of this assay are shown below in Table 2.

TABLE 1

| Example | IMR 32% of Blockade @ $\mu M$ |
| --- | --- |
| 1 | $IC_{50}$ = 2.3 $\mu M$ |
| 2 | 92% @ 10, 36% @ 1 |
| 3 | 70% @ 10, 21% @ 1 |
| 4 | 94% @ 10, 50% @ 1 |
| 5 | 81% @ 10, 24% @ 1 |
| 6 | 31% @ 10, 16% @ 1 |
| 7, 34 | $IC_{50}$ = 0.32 $\mu M$ |
| 8 | 87% @ 10, 70% @ 1 |
| 9 | 89% @ 10, 60% @ 1 |
| 10 | 80% @ 10, 61% @ 1 |
| 11 | 89% @ 10, 70% @ 1 |
| 12 | 88% @ 10, 39% @ 1 |
| 13, 48 | $IC_{50}$ = 0.04 $\mu M$ |
| 14 | 85% @ 10, 80% @ 1 |
| 15 | 80% @ 10, 56% @ 1 |
| 16 | 66% @ 10, 41% @ 1 |
| 17 | $IC_{50}$ = 0.44 $\mu M$ |
| 18 | 95% @ 10, 52% @ 1 |
| 19, 56 | $IC_{50}$ = 0.2 $\mu M$ |
| 20 | 87% @ 10, 65% @ 1 |
| 21 | $IC_{50}$ = 0.88 $\mu M$ |
| 22 | 87% @ 10, 57% @ 1 |
| 23 | 80% @ 3, 53% @ 1 |
| 24 | 84% @ 10, 32% @ 1 |
| 25 | $IC_{50}$ = 0.67 $\mu M$ |
| 26 | $IC_{50}$ = 0.6 $\mu M$ |
| 27 | $IC_{50}$ = 1.3 $\mu M$ |
| 28 | $IC_{50}$ = 0.5 $\mu M$ |
| 29 | $IC_{50}$ = 0.6 $\mu M$ |
| 30 | $IC_{50}$ = 1.2 $\mu M$ |
| 31 | $IC_{50}$ = 0.32 $\mu M$ |
| 32 | $IC_{50}$ = 0.25 $\mu M$ |
| 33 | 95% @ 10, 52% @ 1 |
| 35 | $IC_{50}$ = 2.3 $\mu M$ |
| 36 | $IC_{50}$ = 0.4 $\mu M$ |
| 37 | $IC_{50}$ = 1.0 $\mu M$ |
| 38 | 23% @ 1 |
| 39 | $IC_{50}$ = 0.39 $\mu M$ |
| 40 | $IC_{50}$ = 0.28 $\mu M$ |
| 41 | $IC_{50}$ = 0.28 $\mu M$ |
| 42 | $IC_{50}$ = 0.38 $\mu M$ |
| 43 | 96% @ 10, 51% @ 1 |
| 44 | 74% @ 3, 35% @ 0.3 |
| 45 | 77% @ 3, 45% @ 0.3 |
| 46 | 74% @ 3, 36% @ 0.3 |
| 47 | $IC_{50}$ = 0.28 $\mu M$ |
| 49 | $IC_{50}$ = 0.66 $\mu M$ |
| 50 | $IC_{50}$ = 0.42 $\mu M$ |
| 51 | $IC_{50}$ = 1.3 $\mu M$ |
| 52 | $IC_{50}$ = 0.77 $\mu M$ |
| 53 | $IC_{50}$ = 0.7 $\mu M$ |
| 54 | $IC_{50}$ = 0.36 $\mu M$ |
| 55 | $IC_{50}$ = 0.1 $\mu M$ |
| 57 | $IC_{50}$ = 2.1 $\mu M$ |
| 58 | $IC_{50}$ = 1.0 $\mu M$ |
| 59 | $IC_{50}$ = 1.6 $\mu M$ |
| 60 | $IC_{50}$ = 0.2 $\mu M$ |
| 61 | $IC_{50}$ = 0.4 $\mu M$ |
| 62 | $IC_{50}$ = 1.1 $\mu M$ |
| 63 | $IC_{50}$ = 0.8 $\mu M$ |
| 64 | $IC_{50}$ = 2.4 $\mu M$ |
| 65 | $IC_{50}$ = 1.1 $\mu M$ |

TABLE 1-continued

| Example | IMR 32% of Blockade @ $\mu M$ |
| --- | --- |
| 66 | $IC_{50}$ = 1.9 $\mu M$ |
| 67 | $IC_{50}$ = 0.4 $\mu M$ |
| 68 | $IC_{50}$ = 1.1 $\mu M$ |
| 69 | $IC_{50}$ = 1.3 $\mu M$ |
| 70 | $IC_{50}$ = 2.3 $\mu M$ |
| 71 | $IC_{50}$ = 0.7 $\mu M$ |
| 72 | $IC_{50}$ = 1.2 $\mu M$ |
| 73 | $IC_{50}$ = 2.7 $\mu M$ |
| 74 | $IC_{50}$ = 2.6 $\mu M$ |
| 75 | $IC_{50}$ = 2.4 $\mu M$ |
| 76 | $IC_{50}$ = 0.6 $\mu M$ |
| 77 | $IC_{50}$ = 2.6 $\mu M$ |
| 78 | $IC_{50}$ = 1.6 $\mu M$ |
| 79 | $IC_{50}$ = 2.1 $\mu M$ |
| 80 | $IC_{50}$ = 0.3 $\mu M$ |
| 81 | $IC_{50}$ = 0.16 $\mu M$ |
| 82 | $IC_{50}$ = 1.3 $\mu M$ |
| 83 | $IC_{50}$ = 1.3 $\mu M$ |
| 84 | $IC_{50}$ = 0.37 $\mu M$ |
| 85 | $IC_{50}$ = 0.32 $\mu M$ |
| 86 | $IC_{50}$ = 2.8 $\mu M$ |
| 87 | $IC_{50}$ = 3.1 $\mu M$ |
| 88 | 30% blockade @ 1 $\mu M$ |
| 89 | $IC_{50}$ = 1.0 $\mu M$ |
| 90 | $IC_{50}$ = 0.9 $\mu M$ |
| 91 | $IC_{50}$ = 0.3 $\mu M$ |
| 92 | $IC_{50}$ = 0.8 $\mu M$ |
| 93 | $IC_{50}$ = 0.2 $\mu M$ |
| 94 | 24% @ 1 $\mu M$ |
| 95 | $IC_{50}$ = 0.46 $\mu M$ |
| 96 | $IC_{50}$ = 4.4 $\mu M$ |
| 97 | $IC_{50}$ = 2.2 $\mu M$ |
| 98 | $IC_{50}$ = 0.4 $\mu M$ |
| 99 | $IC_{50}$ = 1.4 $\mu M$ |
| 100 | $IC_{50}$ = 2.0 $\mu M$ |
| 101 | 26% @ 1 $\mu M$ |
| 102 | $IC_{50}$ = 1.6 $\mu M$ |
| 103 | $IC_{50}$ = 1.5 $\mu M$ |
| 104 | $IC_{50}$ = 1.3 $\mu M$ |
| 105 | $IC_{30}$ = 0.24 $\mu M$ |
| 103 | 100%(10 mg/kg) |
| 104 | $IC_{50}$ = 1.3 $\mu M$ |
| 105 | $IC_{50}$ = 0.24 $\mu M$ |
| 116 | 1.4 $\mu M$ |
| 117 | 0.64 $\mu M$ |
| 118 | 1.9 $\mu M$ |
| 119 | 18 $\mu M$ |
| 120 | 6 $\mu M$ |
| 121 | 14 $\mu M$ |
| 122 | 3.1 $\mu M$ |
| 123 | 13 $\mu M$ |
| 124 | 7.2 $\mu M$ |
| 125 | 9.7 $\mu M$ |
| 126 | 6.4 $\mu M$ |
| 127 | 7.5 $\mu M$ |
| 128 | 3.9 $\mu M$ |
| 129 | 6.3 $\mu M$ |
| 130 | 6.5 $\mu M$ |
| 131 | 10 $\mu M$ |
| 132 | 12 $\mu M$ |
| 133 | 5.9 $\mu M$ |
| 134 | 1.6 $\mu M$ |
| 135 | 1.4 $\mu M$ |
| 136 | 3.6 $\mu M$ |
| 137 | 6.2 $\mu M$ |
| 138 | 3.0 $\mu M$ |
| 139 | 38.8 $\mu M$ |
| 140 | 5.1 $\mu M$ |

TABLE 2

In Vivo anticonvulsory Activity in Mico

| Example Number | DBA/2 mice % Protection dose @ 30 mg/kg |
|---|---|
| 7 | 100% |
| 13 | 60% |
| 25 | 100% |
| 31 | 100% |
| 47 | 100% |
| 84 | 100% (10 mg/kg) |
| 90 | 60% (30 mg/kg) |
| 92 | 100% (30 mg/kg) |
| 93 | 80% (30 mg/kg) |
| 97 | 40% (30 mg/kg) |
| 103 | 100% (10 mg/kg) |

What is claimed is:

1. A compound having Formula I

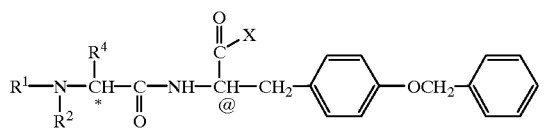

I wherein:

* is a first chiral center;

@ is a second chiral center;

$R^1$ and $R^2$ independently are:

(a) $C_1$–$C_8$ alkyl, unsubstituted or substituted with one or two of halo, hydroxy, amino, alkylamino or dialkylamino;

(b) $C_2$–$C_8$ alkenyl, unsubstituted or substituted with one or two of halo, hydroxy, amino, $C_1$–$C_4$-alkylamino or di(C1–C4)-alkylamino;

(c) $(CH_2)_n$—$C_3$–$C_7$ cycloalkenyl, unsubstituted or substituted by one or two of halo, hydroxy, $C_1$–$C_4$ alkyl, amino, $C_1$–$C_4$-alkylamino or di($C_1$–$C_4$)-alkylamino;

(d) $(CH_2)_n$—$C_3$–$C_7$ cycloalkyl, unsubstituted or substituted with one or two of halo hydroxy, $C_1$–$C_4$ alkyl, amino, $C_1$–$C_4$-alkylamino or di($C_1$–$C_4$)-alkylamino;

(e) $(CH_2)_n$ phenyl, unsubstituted or substituted with one or two of $C_1$–$C_4$ alkyl, benzyloxy, amino, $C_1$–$C_4$ alkylamino, di($C_1$–$C_4$)-alkylamino, halo, $C_1$–$C_4$ alkoxy;

(f) $(CH_2)_n$-pyridyl

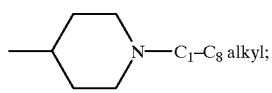

(g)

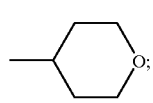

(h)

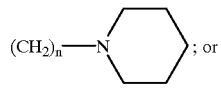

; or (i)

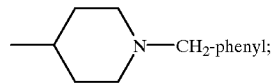

(j)

$R^3$, $R^5$ and $R^6$ independently are hydrogen or $C_1$–$C_8$ alkyl;

$R^4$ is:

(a) $C_1$–$C_8$ alkyl;

(b) $(CH_2)_n$—$C_3$–$C_7$ cycloalkyl, unsubstituted or substituted with one or two of halo, hydroxy, $C_1$–$C_4$ alkyl, amino, $C_1$–$C_4$ alkylamino or di-$C_1$–$C_4$ alkylamino; or (c) $(CH_2)_n$phenyl;

X is:

(a) —$NHR^3$;

(b) —$NR^3R^5$;

(c) —$NH(CH_2)_nNR^3R^5$;

(d) —$NH(CH_2)_nNH(CH_2)_n$phenyl;

(e) —NH $(CH_2)_nNH(CH_2)_n$—OH;

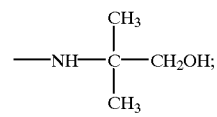

(f)

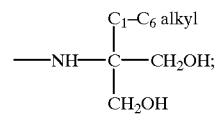

(g)

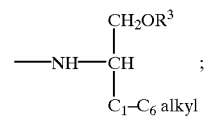

(h)

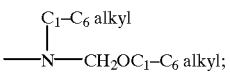

(i)

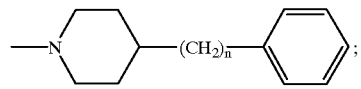

(j)

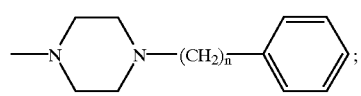

(k)

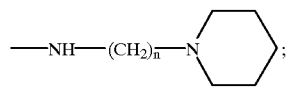

(l)

—NH—$(CH_2)_n$—

(m)

-continued

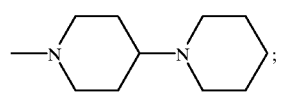 (n)

 (o)

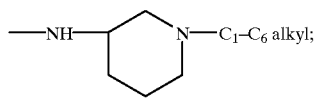 (p)

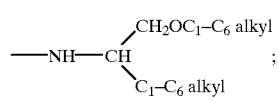 (q)

n is 0 to 5; and the pharmaceutically acceptable salts thereof.

2. A compound according to claim 1 wherein $R^1$ is methyl.

3. A compound according to claim 1 wherein

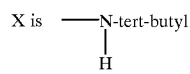

or —O-tert-butyl.

4. A compound according to claim 1 wherein $R^2$ is $C_1$–$C_8$ alkyl, substituted cyclohexyl, cyclohexyl, cyclohexenyl, —$CH_2$-phenyl, —$CH_2$-substituted phenyl, —$CH_2$-cyclohexyl, alkenyl,

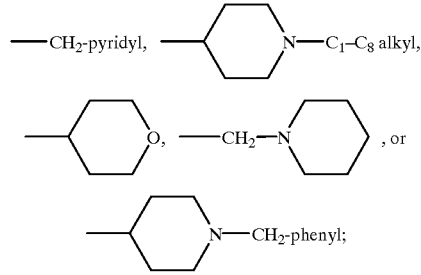

5. A compound according to claim 1 wherein $R^2$ is $C_1$–$C_8$alkyl, cyclohexyl, substituted cyclohexyl, —$CH_2$-phenyl, or $CH_2$-substituted phenyl.

6. A compound according to claim 1 wherein

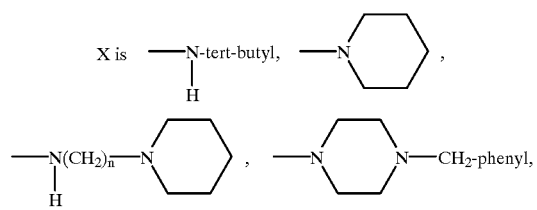

-continued

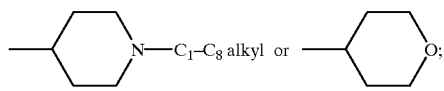

7. A compound according to claim 1 wherein $R^2$ is $C_1$–$C_8$alkenyl.

8. A compound according to claim 1 wherein $R^1$ is methyl;

$R^2$ is $C_1$–$C_8$alkyl, substituted cyclohexyl, cyclohexyl, cyclohexenyl, —$CH_2$-phenyl, —$CH_2$-substituted phenyl, —$CH_2$-cyclohexyl, $C_1$–$C_8$alkenyl, —$CH_2$-pyridyl,

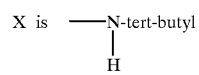

$R^4$ is isobutyl;

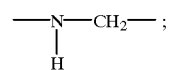

9. A compound according to claim 1 wherein

Y is —O—$CH_2$— or

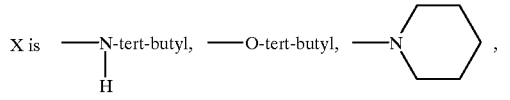

Z is phenyl;

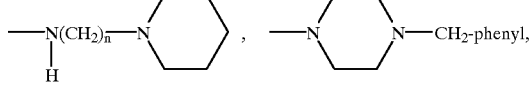

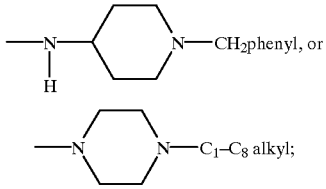

$R^4$ and $R^5$ are hydrogen;

$R^3$ is isobutyl;

$R^1$ is methyl; and $R^2$ is $C_1$–$C_8$alkyl, —$(CH_2)_n$substituted phenyl, or cyclohexyl.

10. A compound selected from:

2-Dimethylamino-4-methyl-pentanoic acid [2-(4-benzyloxy-phenyl)-1-tert-butylcarbamoyl-ethyl]-amide;

2-Dimethylamino-4-methyl-pentanoic acid [2-(4-benzyloxy-phenyl)-1-(piperidine-1-carbonyl)-ethyl]-amide;

2-Dimethylamino-4-methyl-pentanoic acid [2-(4-benzyloxy-phenyl)-1-(2-piperidin-1-yl-ethylcarbamoyl)-ethyl]-amide;

2-Dimethylamino-4-methyl-pentanoic acid [1-(4-benzyloxy-benzyl)-2-(4-benzyl-piperazin-1-yl)-2-oxo-ethyl]-amide;

2-Dimethylamino-4-methyl-pentanoic acid [2-(4-benzyloxy-benzyl)-1-(1-benzyl-piperidin-4-yl-carbamoyl)-ethyl]-amide;

2-Dimethylamino-4-methyl-pentanoic acid [1-(4-benzyloxy-benzyl)-2-(4-methyl-piperazin-1-yl)-2-oxo-ethyl]-amide;

4-Methyl-2-[methyl-(3-methyl-butyl)-amino]-pentanoic acid [2-(4-benzyloxy-phenyl)-1-tert-butylcarbamoyl-ethyl]-amide;

4-Methyl-2-[methyl-(3-methyl-butyl)-amino]-pentanoic acid [1-(4-benzyloxy-benzyl)-2-oxo-2-piperidin-1-yl-ethyl]-amide;

4-Methyl-2-[methyl-(3-methyl-butyl)-amino]-pentanoic acid [2-(4-benzyloxy-phenyl)-1-(2-piperidin-1-yl-ethylcarbamoyl)-ethyl]-amide;

4-Methyl-2-[methyl-(3-methyl-butyl)-amino]-pentanoic acid [1-(4-benzyloxy-benzyl)-2-(4-benzyl-piperazin-1-yl)-2-oxo-ethyl]-amide;

4-Methyl-2-[methyl-(3-methyl-butyl)-amino]-pentanoic acid [2-(4-benzyloxy-phenyl)-1-(1-benzyl-piperidin-4-ylcarbamoyl)-ethyl]-amide;

4-Methyl-2-[methyl-(3-methyl-butyl)-amino]-pentanoic acid [1-(4-benzyloxy-benzyl)-2-(4-methyl-piperazin-1-yl)-2-oxo-ethyl]-amide;

2-[(4-tert-Butyl-benzyl)-methyl-amino]-4-methyl-pentanoic acid [2-(4-benzyloxy-phenyl)-1-tert-butylcarbamoyl-ethyl]-amide;

2-[(4-tert-Butyl-benzyl)-methyl-amino]-4-methyl-pentanoic acid [2-(4-benzyloxy-phenyl)-1-(piperidine-1-carbonyl)-ethyl]-amide;

2-[(4-tert-Butyl-benzyl)-methyl-amino]-4-methyl-pentanoic acid [2-(4-benzyloxy-phenyl)-1-(2-piperidin-1-yl-ethylcarbamoyl)-ethyl]-amide;

2-[(4-tert-Butyl-benzyl)-methyl-amino]-4-methyl-pentanoic acid [1-(4-benzyloxy-benzyl)-2-(4-benzyl-piperazin-1-yl)-2-oxo-ethyl]-amide;

2-[(4-tert-Butyl-benzyl)-methyl-amino]-4-methyl-pentanoic acid [2-(4-benzyloxy-phenyl)-1-(1-benzyl-piperidin-4-yl-carbamoyl)-ethyl]-amide;

2-[(4-tert-Butyl-benzyl)-methyl-amino]-4-methyl-pentanoic acid [1-(4-benzyloxy-benzyl)-2-(4-methyl-piperazin-1-yl)-2-oxo-ethyl]-amide;

2-(Cyclohexyl-methyl-amino)-4-methyl-pentanoic acid [2-(4-benzyloxy-phenyl)-1-tert-butylcarbamoyl-ethyl]-amide;

2-(Cyclohexyl-methyl-amino)-4-methyl-pentanoic acid [2-(4-benzyloxy-phenyl)-1-(piperidine-1-carbonyl)-ethyl]-amide;

2-(Cyclohexyl-methyl-amino)-4-methyl-pentanoic acid [2-(4-benzyloxy-phenyl)-1-(2-piperidin-1-yl-ethylcarbamoyl)-ethyl]-amide;

2-(Cyclohexyl-methyl-amino)-4-methyl-pentanoic acid [1-(4-benzyloxy-benzyl)-2-(4-benzyl-piperazin-1-yl)-2-oxo-ethyl]-amide;

2-(Cyclohexyl-methyl-amino)-4-methyl-pentanoic acid [2-(4-benzyloxy-phenyl)-1-(1-benzyl-piperidin-4-ylcarbamoyl)-ethyl]-amide;

2-(Cyclohexyl-methyl-amino)-4-methyl-pentanoic acid [1-(4-benzyloxy-benzyl)-2-(4-methyl-piperazin-1-yl)-2-oxo-ethyl]-amide;

2-(Cyclohexylmethyl-methyl-amino)-4-methyl-pentanoic acid [2-(4-benzyloxy-phenyl)-1-tert-butylcarbamoyl-ethyl]-amide;

2-(Cyclohexylmethyl-methyl-amino)-4-methyl-pentanoic acid [2-(4-benzyloxy-phenyl)-1-(piperidine-1-carbonyl)-ethyl]-amide;

2-(Cyclohexylmethyl-methyl-amino)-4-methyl-pentanoic acid [2-(4-benzyloxy-phenyl)-1-(2-piperidin-1-yl-ethylcarbamoyl)-ethyl]-amide;

2-(Cyclohexylmethyl-methyl-amino)-4-methyl-pentanoic acid [1-(4-benzyloxy-benzyl)-2-(4-benzyl-piperazin-1-yl)-2-oxo-ethyl]-amide;

2-(Cyclohexylmethyl-methyl-amino)-4-methyl-pentanoic acid [2-(4-benzyloxy-phenyl)-1-(1-benzyl-piperidin-4-ylcarbamoyl)-ethyl]-amide;

2-(Cyclohexylmethyl-methyl-amino)-4-methyl-pentanoic acid [1-(4-benzyloxy-benzyl)-2-(4-methyl-piperazin-1-yl)-2-oxo-ethyl]-amide;

3-(4-Benzyloxy-phenyl)-2-[4-methyl-2-(3-methyl-but-2-enylamino)-pentanoylamino]-propionic acid tert-butyl ester;

3-(4-Benzyloxy-phenyl)-2-[2-(4-tert-butyl-benzylamino)-4-methyl-pentanoylamino]-propionic acid tert-butyl ester;

2-(2-Benzylamino-4-methyl-pentanoylamino)-3-(4-benzyloxy-phenyl)-propionic acid tert-butyl ester;

4-Methyl-2-[methyl-(3-methyl-butyl)-amino]-pentanoic acid [2-(4-benzyloxy-phenyl)-1-tert-butylcarbamoyl-ethyl]-amide;

4-Methyl-2-methylamino-pentanoic acid [2-(4-benzyloxy-phenyl)-1-tert-butylcarbamoyl-ethyl]-amide;

2-[(3,3-Dimethyl-butyl)-methyl-amino]-4-methyl-pentanoic acid [2-(4-benzyloxy-phenyl)-1-tert-butylcarbamoyl-ethyl]-amide;

2-Diethylamino-4-methyl-pentanoic acid [2-(4-benzyloxy-phenyl)-1-tert-butylcarbamoyl-ethyl-]-amide;

2-[(4-tert-Butyl-cyclohexyl)-methyl-amino]-4-methyl-pentanoic acid [2-(4-benzyloxy-phenyl)-1-tert-butylcarbamoyl-ethyl]-amide;

4-Methyl-2-[methyl-(4-methyl-cyclohexyl)-amino]-pentanoic acid [2-(4-benzyloxy-phenyl)-1-tert-butylcarbamoyl-ethyl]-amide;

2-[(4-Dimethylamino-benzyl)-methyl-amino]-4-methyl-pentanoic acid [2-(4-benzyloxy-phenyl)-1-tert-butylcarbarnoyl-ethyl]-amide;

2-(Butyl-methyl-amino)-4-methyl-pentanoic acid [2-(4-benzyloxy-phenyl)-1-tert-butylcarbamoyl-ethyl]-amide;

2-(Isobutyl-methyl-amino)-4-methyl-pentanoic acid [2-(4-benzyloxy-phenyl)-1-tert-butylcarbamoyl-ethyl]-amide;

4-Methyl-2-methylamino-pentanoic acid [1-(4-benzyloxy-benzyl)-2-(4-benzyl-piperazin-1-yl)-2-oxo-ethyl]-amide;

3-Methyl-2-[methyl-(3-methyl-butyl)-amino]-pentanoic acid [2-(4-benzyloxy-phenyl)-1-tert-butylcarbamoyl-ethyl]-amide;

4-Methyl-2-[ethyl-(3-methyl-butyl)-amino]-pentanoic acid [2-(4-benzyloxy-phenyl)-1-tert-butylcarbamoyl-ethyl]-amide;

4-Methyl-2-[methyl-(3-methyl-butyl)-amino]-butyric acid [2-(4-benzyloxy-phenyl)-1-tert-butylcarbamoyl-ethyl]-amide;

2-(Cyclohex-2-enyl-methyl-amino)-4-methyl-pentanoic acid [2-(4-benzyloxy-phenyl)-1-tert-butylcarbamoyl-ethyl]-amide;

2-[(4-tert-Butyl-benzyl)-methyl-amino]-4-methyl-pentanoic acid [2-(4-benzyloxy-phenyl)-1-tert-butylcarbamoyl-ethyl]-amide;

2-(Cyclohex-2-enylamino)-4-methyl-pentanoic acid [2-(4-benzyloxy-phenyl)-1-tert-butylcarbamoyl-ethyl]-amide;

2-(4-tert-Butyl-benzylamino)-4-methyl-pentanoic acid [2-(4-benzyloxy-phenyl)-1-tert-butylcarbamoyl-ethyl]-amide;

4-Methyl-2-[methyl-(3-methyl-but-2-enyl)-amino]-pentanoic acid [2-(4-benzyloxy-phenyl)-1-tert-butylcarbamoyl-ethyl]-amide;

2-(4-tert-Butyl-benzylamino)-4-methyl-pentanoic acid [1-(4-benzyloxy-benzyl)-2-(4-benzyl-piperazin-1-yl)-2-oxo-ethyl]-amide;

4-Methyl-2-(3-methyl-but-2-enylamino)-pentanoic acid [1-(4-benzyloxy-benzyl)-2-(4-benzyl-piperazin-1-yl)-2-oxo-ethyl]-amide;

2-(Benzyl-methyl-amino)-4-methyl-pentanoic acid [2-(4-benzyloxy-phenyl)-1-tert-butylcarbamoyl-ethyl]-amide;

2-[(4-tert-Butyl-benzyl)-methyl-amino]-4-methyl-pentanoic acid [2-(4-benzylamino-phenyl)-1-tert-butylcarbamoyl-ethyl]-amide; and 2-(Cyclohexyl-methyl-amino)-4-methyl-pentanoic acid [2-(4-benzyloxy-phenyl)-1-tert-butylcarbamoyl-ethyl]-amide.

11. A compound selected from:

2-[(4-Chloro-benzyl)-methyl-amino]-4-methyl-pentanoic acid [2-(4-benzyloxy-phenyl)-1-tert-butylcarbamoyl-ethyl]-amide;

2-[(2-Chloro-benzyl)-methyl-amino]-4-methyl-pentanoic acid [2-(4-benzyloxy-phenyl)-1-tert-butylcarbamoyl-ethyl]-amide;

2-[(3-Chloro-benzyl)-methyl-amino]-4-methyl-pentanoic acid [2-(4-benzyloxy-phenyl)-1-tert-butylcarbamoyl-ethyl]-amide;

2-[(4-Methoxybenzyl)-methyl-amino]-4-methyl-pentanoic acid [2-(4-benzyloxy-phenyl)-1-tert-butylcarbamoyl-ethyl]-amide;

2-[(4-Ethoxybenzyl)-methyl-amino]-4-methyl-pentanoic acid [2-(4-benzyloxy-phenyl)-1-tert-butylcarbamoyl-ethyl]-amide;

2-[(3-Methoxybenzyl)-methyl-amino]-4-methyl-pentanoic acid [2-(4-benzyloxy-phenyl)-1-tert-butylcarbamoyl-ethyl]-amide;

2-[(2-Methoxybenzyl)-methyl-amino]-4-methyl-pentanoic acid [2-(4-benzyloxy-phenyl)-1-tert-butylcarbamoyl-ethyl]-amide;

2-[(4-Pyridyl)-methyl-amino]-4-methyl-pentanoic acid [2-(4-benzyloxy-phenyl)-1-tert-butylcarbamoyl-ethyl]-amide;

2-(2-Hydroxycyclohexyl-methyl-amino)-4-methyl-pentanoic acid [2-(4-benzyloxy-phenyl)-1-tert-butylcarbamoyl-ethyl]-amide;

4-Methyl-2-[methyl-(N,N-dimethyl-3-amino-propyl)-amino]-pentanoic acid [2-(4-benzyloxy-phenyl)-1-tert-butylcarbamoyl-ethyl]-amide;

2-(Cyclohexyl-amino)-4-methyl-pentanoic acid [2-(4-benzyloxy-phenyl)-1-tert-butylcarbamoyl-ethyl]-amide;

2-[(Isoprop-2-yl)-amino]-4-methyl-pentanoic acid [2-(4-benzyloxy-phenyl)-1-tert-butylcarbamoyl-ethyl]-amide;

2-[(Isoprop-2-yl)-methyl-amino]-4-methyl-pentanoic acid [2-(4-benzyloxy-phenyl)-1-tert-butylcarbamoyl-ethyl]-amide;

2-[(N-methyl-piperidin-4-yl)-methyl-amino]-4-methyl-pentanoic acid [2-(4-benzyloxy-phenyl)-1-tert-butylcarbamoyl-ethyl]-amide;

2-[(N-methyl-piperidin-4-yl)-amino]-4-methyl-pentanoic acid [2-(4-benzyloxy-phenyl)-1-tert-butylcarbamoyl-ethyl]-amide;

2-[(Pyran-4-yl)-methyl-amino]-4-methyl-pentanoic acid [2-(4-benzyloxy-phenyl)-1-tert-butylcarbamoyl-ethyl]-amide;

2-[(Pyran-4-yl)-amino]-4-methyl-pentanoic acid [2-(4-benzyloxy-phenyl)-1-tert-butylcarbamoyl-ethyl]-amide;

2-Pyrrolidine-4-methyl-pentanoic acid [2-(4-benzyloxy-phenyl)-1-tert-butylcarbamoyl-ethyl]-amide;

2-Piperidine-4-methyl-pentanoic acid [2-(4-benzyloxy-phenyl)-1-tert-butylcarbamoyl-ethyl]-amide;

2-Hexamethyleneimine-4-methyl-pentanoic acid [2-(4-benzyloxy-phenyl)-1-tert-butylcarbamoyl-ethyl]-amide;

2-[(4-Fluoro-benzyl)-methyl-amino]-4-methyl-pentanoic acid [2-(4-benzyloxy-phenyl)-1-(piperidine-1-carbamoyl-ethyl]-amide;

2-[(4-Chloro-benzyl)-methyl-amino]-4-methyl-pentanoic acid [2-(4-benzyloxy-phenyl)-1-(piperidine-1-carbamoyl-ethyl]-amide;

2-[(4-Bromo-benzyl)-methyl-amino]-4-methyl-pentanoic acid [2-(4-benzyloxy-phenyl)-1-(piperidine-1-carbamoyl-ethyl]-amide;

2-[(2-Chloro-benzyl)-methyl-amino]-4-methyl-pentanoic acid [2-(4-benzyloxy-phenyl)-1-(piperidine-1-carbamoyl-ethyl]-amide;

2-[(3-Chloro-benzyl)-methyl-amino-4-methyl-pentanoic acid [2-(4-benzyloxy-phenyl)-1-(piperidine-1-carbamoyl-ethyl]-amide;

2-[(4-Hydroxybenzyl)-methyl-amino]-4-methyl-pentanoic acid [2-(4-benzyloxy-phenyl)-1-(piperidine-1-carbamoyl-ethyl]-amide;

2-[(4-Methoxybenzyl)-methyl-amino]-4-methyl-pentanoic acid [2-(4-benzyloxy-phenyl)-1-(piperidine-1-carbamoyl-ethyl]-amide;

2-[(4-Ethoxybenzyl)-methyl-amino]-4-methyl-pentanoic acid [2-(4-benzyloxy-phenyl)-1-tert-(piperidine-1-carbamoyl-ethyl]-amide;

2-[(3-Methoxybenzyl)-methyl-amino]-4-methyl-pentanoic acid [2-(4-benzyloxy-phenyl)-1-(piperidine-1-carbamoyl-ethyl]-amide;

2-[(2-Methoxybenzyl)-methyl-amino]-4-methyl-pentanoic acid [2-(4-benzyloxy-phenyl)-1-(piperidine-1-carbamoyl-ethyl]-amide;

2-[(4-Pyridyl)-methyl-amino]-4-methyl-pentanoic acid [2-(4-benzyloxy-phenyl)-1-(piperidine-1-carbamoyl-ethyl]-amide;

2-[(2-Hydroxycyclohexyl-methyl-amino]-4-methyl-pentanoic acid [2-(4-benzyloxy-phenyl)-1-(piperidine-1-carbamoyl-ethyl]-amide;

4-Methyl-2-[methyl-(N,N-dimethyl-3-amino-propyl)-amino]-pentanoic acid [2-(4-benzyloxy-phenyl)-1-(piperidine-1-carbamoyl-ethyl]-amide;

2-(Cyclohexyl-amino)-4-methyl-pentanoic acid [2-(4-benzyloxy-phenyl)-1-(piperidine-1-carbamoyl-ethyl]-amide;

2-(Isoprop-2-yl)-amino]-4-methyl-pentanoic acid [2-(4-benzyloxy-phenyl)-1-(piperidine-1-carbamoyl-ethyl]-amide;

2-(Isoprop-2-yl)-methyl-amino)-4-methyl-pentanoic acid [2-(4-benzyloxy-phenyl)-1-(piperidine-1-carbamoyl-ethyl]-amide;

2-[N-methyl-piperidin-4-yl)-methyl-amino]-4-methyl-pentanoic acid [2-(4-benzyloxy-phenyl)-1-(piperidine-1-carbamoyl-ethyl]-amide;

2-[(N-methyl-piperidin-4-yl)-methyl-pentanoic acid [2-(4-benzyloxy-phenyl)-1-(piperidine-1-carbamoyl-ethyl]-amide;

2-[(Pyran-4-yl)-methyl-amino]4-methyl-pentanoic acid [2-(4-benzyloxy-phenyl)-1-(piperidine-1-carbamoyl-ethyl]-amide;

2-[(Pyran-4-yl)-amino]-4-methyl-pentanoic acid [2-(4-benzyloxy-phenyl)-1-(piperidine-1-carbamoyl-ethyl]-amide;

2-Pyrrolidine-4-methyl-pentanoic acid [2-(4-benzyloxy-phenyl)-1-(piperidine-1-carbamoyl-ethyl]-amide;

2-Piperidine-4-methyl-pentanoic acid [2-(4-benzyloxy-phenyl-1-(piperidine-1-carbamoyl-ethyl]-amide;

2-Hexamethyleneimine-4-methyl-pentanoic acid [2-(4-benzyloxy-phenyl)-1-(piperidine-1-carbamoyl-ethyl]-amide;

2-[(4-Fluoro-benzyl)-methyl-amino]-4-methyl-pentanoic acid [2-(4-benzyloxy-phenyl)-1-tert-butylcarbamoyl-ethyl]-amide;

2-[(4-Chloro-benzyl)-methyl-amino]-4-methyl-pentanoic acid [2-(4-benzyloxy-phenyl)-1-tert-butylcarbamoyl-ethyl]-amide;

2-[(4-Bromo-benzyl)-methyl-amino]4-methyl-pentanoic acid [2-(4-benzyloxy-phenyl)-1-tert-butylcarbamoyl-ethyl]-amide;

2-[(2-Chloro-benzyl)-methyl-amino]-4-methyl-pentanoic acid [2-(4-benzyloxy-phenyl)-1-tert-butylcarbamoyl-ethyl]-amide;

2-[(3-Chloro-benzyl)-methyl-amino]-4-methyl-pentanoic acid [2-(4-benzyloxy-phenyl)-1-tert-butylcarbamoyl-ethyl]-amide;

2-[(4-Hydroxybenzyl)-methyl-amino]-4-methyl-pentanoic acid [2-(4-benzyloxy-phenyl)-1-tert-butylcarbamoyl-ethyl]-amide;

2-[(4-Methoxybenzyl)-methyl-amino]-4-methyl-pentanoic acid [2-(4-benzyloxy-phenyl)-1-tert-butylcarbamoyl-ethyl]-amide;

2-[(4-Ethoxybenzyl)-methyl-amino]-4-methyl-pentanoic acid [2-(4-benzyloxy-phenyl)-1-tert-butylcarbamoyl-ethyl]-amide;

2-[(3-Methoxybenzyl)-methyl-amino]-4-methyl-pentanoic acid [2-(4-benzyloxy-phenyl)-1-tert-butylcarbamoyl-ethyl]-amide;

2-[(2-Methoxybenzyl)-methyl-amino]-4-methyl-pentanoic acid [2-(4-benzyloxy-phenyl)-1-tert-butylcarbamoyl-ethyl]-amide;

2-[(4-Pyridyl)-methyl-amino]-4-methyl-pentanoic acid [2-(4-benzyloxy-phenyl)-1-tert-butylcarbamoyl-ethyl]-amide;

2-(2-Hydroxycyclohexyl-methyl-amino)-4-methyl-pentanoic acid [2-(4-benzyloxy-phenyl)-1-tert-butylcarbamoyl-ethyl]-amide;

4-Methyl-2-[methyl-(N,N-dimethyl-3-amino-propyl)-amino]-pentanoic acid [2-(4-benzyloxy-phenyl)-1-tert-butylcarbamoyl-ethyl]-amide;

2-(Cyclohexyl-amino)-4-methyl-pentanoic acid [2-(4-benzyloxy-phenyl)-2-(4-methyl-piperazin-1-yl)-2-oxo-ethyl]-amide;

2-[(Isoprop-2-yl)-amino]-4-methyl-pentanoic acid [2-(4-benzyloxy-phenyl)-2-(4-methyl-piperazin-1-yl)-2-oxo-ethyl]-amide;

2-[(Isoprop-2-yl)-methyl-amino]-4-methyl-pentanoic acid [2-(4-benzyloxy-phenyl)-2-(4-methyl-piperazin-1-yl)-2-oxo-ethyl]-amide;

2-Pyrrolidine-4-methyl-pentanoic acid [2-(4-benzyloxy-phenyl)-2-(4-methyl-piperazin-1-yl)-2-oxo-ethyl]-amide;

2-Piperidine-4-methyl-pentanoic acid [2-(4-benzyloxy-phenyl)-2-(4-methyl-piperazin-1-yl)-2-oxo-ethyl]-amide; and 2-Hexamethyleneimine-4-methyl-pentanoic acid [2-(4-benzyloxy-phenyl)-2-(4-methyl-piperazin-1-yl)-2-oxo-ethyl]-amide.

12. A pharmaceutical composition comprising a compound of claim 1.

13. A method of treating epilepsy, the method comprising administering to a patient having epilepsy a therapeutically effective amount of a compound of claim 1.

14. A method of treating pain, the method comprising administering to a patient having pain a therapeutically effective amount of a compound of claim 1.

15. The compounds:

[S-(R*,R*)]-4-Methyl-2-[methyl-(3-methyl-butyl)-amino]-pentanoic acid [2-(4-benzyloxy-phenyl)-1-(2-morpholin-4-yl-ethylcarbamoyl)-ethyl]-amide;

[S-(R*,R* )]-4-Methyl-2-[methyl-(3-methyl-butyl)-amino]-pentanoic acid [2-(4-benzyloxy-phenyl)-1-(2-pyridin-2-yl-ethylcarbamoyl)-ethyl]-amide;

[S-(R*,R*)]-4-Methyl-2-[methyl-(3-methyl-butyl)-amino]-pentanoic acid [2-(4-benzyloxy-phenyl)-1-(3-imidazol-1-yl-propylcarbamoyl)-ethyl]-amide;

[S-(R*,R*)]-4-Methyl-2-[methyl-(3-methyl-butyl)-amino]-pentanoic acid [1-(2-benzylamino-ethylcarbamoyl)-2-(4-benzyloxy-phenyl)-ethyl]-amide;

[S-(R*,R*)]-4-Methyl-2-[methyl-(3-methyl-butyl)-amino]-pentanoic acid [1-(4-benzyloxy-benzyl)-2-oxo-2-thiomorpholin-4-yl-ethyl]-amide;

[S-(R* ,R*)]-4-Methyl-2-[methyl-(3-methyl-butyl)-amino]-pentanoic acid [2-(4-benzyloxy-phenyl)-1-(2-hydroxy-1-hydroxymethyl-1-methyl-ethylcarbamoyl)-ethyl]-amide;

[S-(R*,R*)]-4-Methyl-2-[methyl-(3-methyl-butyl)-amino]-pentanoic acid [2-(4-benzyloxy-phenyl)-1-(1-methoxymethyl-propylcarbamoyl)-ethyl]-amide;

[S-(R*,R*)]-4-Methyl-2-[methyl-(3-methyl-butyl)-amino]-pentanoic acid [2-(4-benzyloxy-phenyl)-1-(2-pyrrolidin-1-yl-ethylcarbamoyl)-ethyl]-amide;

[S-(R*,R*)]-4-Methyl-2-[methyl-(3-methyl-butyl)-amino]-pentanoic acid [1-(4-benzyloxy-benzyl)-2-(4-hydroxy-piperidin-1-yl)-2-oxo-ethyl]-amide; and

[S-(R*,R*)]-4-Methyl-2-[methyl-(3-methyl-butyl)-amino]-pentanoic acid {2-(4-benzyloxy-phenyl)-1-[2-(2-hydroxy-ethylamino)-ethylcarbamoyl]-ethyl}-amide.

16. The compounds:

[S-(R*,R*)]-4-Methyl-2-[methyl-(3-methyl-butyl)-amino]-pentanoic acid [2-(4-benzyloxy-phenyl)-1-(1-benzyl-pyrrolidin-3-ylcarbamoyl)-ethyl]-amide;

[S-(R*,R*)]-4-Methyl-2-morpholin-4-yl-pentanoic acid [1-(2-benzylamino-ethylcarbamoyl)-2-(4-benzyloxy-phenyl)-ethyl]-amide;

[S-(R*,R*)]-4-Methyl-2-morpholin-4-yl-pentanoic acid [2-(4-benzyloxy-phenyl)-1-(1-benzyl-pyrrolidin-3-ylcarbamoyl)-ethyl]-amide;

[S-(R*,R*)]-4-Methyl-2-morpholin-4-yl-pentanoic acid [1-(4-benzyloxy-benzyl)-2-oxo-2-piperidin-1-yl-ethyl]-amide;

[S-(R*,R*)]-4-Methyl-2-(tetrahydro-pyran-4-ylamino)-pentanoic acid [1-(2-benzylamino-ethylcarbamoyl)-2-(4-benzyloxy-phenyl)-ethyl]-amide;

[S-(R*,R*)]-4-Methyl-2-(tetrahydro-pyran-4-ylamino)-pentanoic acid [1-(4-benzyloxy-benzyl)-2-oxo-2-thiomorpholin-4-yl-ethyl]-amide;

[S-(R*,R*)]-4-Methyl-2-(tetrahydro-pyran-4-ylamino)-pentanoic acid [2-(4-benzyloxy-phenyl)-1-(2-hydroxy-1,1-dimethyl-ethylcarbamoyl)-ethyl]-amide;

[S-(R*,R*)]-4-Methyl-2-(tetrahydro-pyran-4-ylamino)-pentanoic acid [2-(4-benzyloxy-phenyl)-1-(1,1-bis-hydroxymethyl-propylcarbamoyl)-ethyl]-amide;

[S-(R*,R*)]-4-Methyl-2-(tetrahydro-pyran-4-ylamino)-pentanoic acid [2-(4-benzyloxy-phenyl)-1-(1-methoxymethyl-propylcarbamoyl)-ethyl]-amide; and

[S-(R*,R*)]-4-Methyl-2-(tetrahydro-pyran-4-ylamino)-pentanoic acid [2-(4-benzyloxy-phenyl)-1-(1-benzyl-pyrrolidin-3-ylcarbamoyl)-ethyl]-amide.

17. The compounds:

[S-(R*,R*)]-4-Methyl-2-(tetrahydro-pyran-4-ylamino)-pentanoic acid [2-(4-benzyloxy-phenyl)-1-(2-piperidin-1-yl-ethylcarbamoyl)-ethyl]-amide;

[S-(R*,R*)]-4-Methyl-2-(tetrahydro-pyran-4-ylamino)-pentanoic acid [2-(4-benzyloxy-phenyl)-1-tert-butylcarbamoyl-ethyl]-amide;

[S-(R*,R*)]-4-Methyl-2-(tetrahydro-pyran-4-ylamino)-pentanoic acid [1-(4-benzyloxy-benzyl)-2-oxo-2-piperidin-1-yl-ethyl]-amide;

[S-(R*,R*)]-2-[(4-Fluoro-benzyl)-methyl-amino]-4-methyl-pentanoic acid [2-(4-benzyloxy-phenyl)-1-tert-butylcarbamoyl-ethyl]-amide;

[S-(R*,R*)]-2-[(4-Bromo-benzyl)-methyl-amino]-4-methyl-pentanoic acid [2-(4-benzyloxy-phenyl)-1-tert-butylcarbamoyl-ethyl]-amide;

[S-(R*,R*)]-2-[(4-Hydroxy-benzyl)-methyl-amino]-4-methyl-pentanoic acid [2-(4-benzyloxy-phenyl)-1-tert-butylcarbamoyl-ethyl]-amide;

[S-(R*,R*)]-4-Methyl-2-(methyl-pyridin-4-ylmethyl-amino)-pentanoic acid [2-(4-benzyloxy-phenyl)-1-tert-butylcarbamoyl-ethyl]-amide;

[S-(R*,S*)]-4-Methyl-2-[methyl-(3-methyl-butyl)-amino]-pentanoic acid [2-(4-benzyloxy-phenyl)-1-tert-butylcarbamoyl-ethyl]-amide;

[S-(R*,R*)]-3-(4-Benzyloxy-phenyl)-2-[4-methyl-2-(tetrahydro-pyran-4-ylamino)-pentanoylamino]-propionic acid tert-butyl ester; and

[S-(R*,R*)]-2-(Isopropyl-methyl-amino)-4-methyl-pentanoic acid [2-(4-benzyloxy-phenyl)-1-tert-butylcarbamoyl-ethyl]-amide.

18. The compounds:

[S-(R*,R*)]-4-Methyl-2-[methyl-(tetrahydro-pyran-4-yl)-amino]-pentanoic acid [2-(4-benzyloxy-phenyl)-1-tert-butylcarbamoyl-ethyl]-amide;

[S-[R*,R*,(RS)]]-2-[(2-Hydroxy-1-methyl-ethyl)-methyl-amino]-4-methyl-pentanoic acid [2-(4-benzyloxy-phenyl)-1-tert-butylcarbamoyl-ethyl]-amide;

[S-(R*,R*)]-4-Methyl-2-[methyl-(1H-pyrrol-2-ylmethyl)-amino]-pentanoic acid [2-(4-benzyloxy-phenyl)-1-tert-butylcarbamoyl-ethyl]-amide;

[S-(R*,R*)]-2-(Furan-2-ylmethyl-methyl-amino)-4-methyl-pentanoic acid [2-(4-benzyloxy-phenyl)-1-tert-butylcarbamoyl-ethyl]-amide;

[S-(R*,R*)]-3-(4-Benzyloxy-phenyl)-2-[2-(cyclohexylmethyl-amino)-4-methyl-pentanoylamino]-propionic acid tert-butyl ester;

[S-(R*,R*)]-3-(4-Benzyloxy-phenyl)-2-(2-isopropylamino-4-methyl-pentanoylamino)-propionic acid tert-butyl ester;

[S-(R*,R*)]-3-3-(4-Benzyloxy-phenyl)-2-(2-cyclohexylamino-4-methyl-pentanoylamino)-propionic acid tert-butyl ester;

[S-(R*,R*)]-4-Methyl-2-morpholin-4-yl-pentanoic acid [2-(4-benzyloxy-phenyl)-1-tert-butylcarbamoyl-ethyl]-amide;

[S-(R*,R*)]-3-(4-Benzyloxy-phenyl)-2-[4-methyl-2-(3-methyl-butylamino)-pentanoylamino]-propionic acid tert-butyl ester; and

[S-(R*,R*)]-({1-[2-(4-Benzyloxy-phenyl)-1-tert-butylcarbamoyl-ethylcarbamoyl]-3-methyl-butyl}-methyl-amino)-acetic acid ethyl ester.

19. The compounds:

[S-(R*,R*)]-2-[(3-Hydroxy-butyl)-methyl-amino]-4-methyl-pentanoic acid [2-(4-benzyloxy-phenyl)-1-tert-butylcarbamoyl-ethyl]-amide;

[S-(R*,R*)]-2-[(4-Methoxy-benzyl)-methyl-amino]-4-methyl-pentanoic acid [2-(4-benzyloxy-phenyl)-1-tert-butylcarbamoyl-ethyl]-amide;

[S-(R*,R*)]-4-Methyl-2-piperidin-1-yl-pentanoic acid [2-(4-benzyloxy-phenyl)-1-tert-butylcarbamoyl-ethyl]-amide;

[S-(R*,R*)]-2-Ethylamino-4-methyl-pentanoic acid [2-(4-benzyloxy-phenyl)-1-tert-butylcarbamoyl-ethyl]-amide;

[S-(R*,R*)]-4-Methyl-2-(methyl-pyridin-3-ylmethyl-amino)-pentanoic acid [2-(4-benzyloxy-phenyl)-1-tert-butylcarbamoyl-ethyl]-amide;

[S-(R*,R*)]-3-(4-Benzyloxy-phenyl)-N-tert-butyl-2-{2-[methyl-(3-methyl-butyl)-amino]-acetylamino}-propionamide;

[S-[R*,R*,(RS)]]-2-(sec-Butyl-methyl-amino)-4-methyl-pentanoic acid [2-(4-benzyloxy-phenyl)-1-tert-butylcarbamoyl-ethyl]-amide;

(S)-N-[2-(4-Benzyloxy-phenyl)-1-tert-butylcarbamoyl-ethyl]-2-(3-methyl-butylamino)-isobutyramide;

[S-(R*,R*)]-4-Methyl-2-(3-methyl-butylamino)-pentanoic acid [2-(4-benzyloxy-phenyl)-1-tert-butylcarbamoyl-ethyl]-amide; and 4-Methyl-2-[methyl-(tetrahydro-pyran-4-yl)-amino]-pentanoic acid [2-(4-benzyloxyphenyl)-1-(1-methoxymethyl-propylcarbamoyl)-ethyl]-amide.

20. The compounds:

4-Methyl-2-[methyl-(3-methylbutyl)-amino]3-pentanoic acid [2-(4-benzyloxyphenyl)-1-(1-methoxymethyl-propylcarbamoyl)-ethyl]-amide;

2-(Isopropyl-methyl-amino)-4-methyl-pentanioc acid [2-(4-benzyloxyphenyl)-1-(1-methoxymethyl-propylcarbamoyl)-ethyl]-amide;

-2-[(4-tert-butyl-benzyl)-methyl-amino]-4-methyl-pentanoic acid [2-(4-benzyloxyphenyl)-1-(1-methoxymethyl-propylcarbamoyl)-ethyl]-amide;

2-[(4-Dimethylamino-benzyl)-methyl-amino]-4-methyl-pentanoic acid [2-(4-benzyloxyphenyl)-1-(1-methoxymethyl-propylcarbamoyl)-ethyl]-amide;

4-Methyl-2-[methyl-tetrahydropyran-4-yl)-amino]-pentanoic acid [2-(4-benzyloxyphenyl)-1-(1-propyl-piperidin-3-ylcarbamoyl)-ethyl]-amide;

4-Methyl-2-[methyl-(3-methyl-butyl-amino]-pentanoic acid [2-(4-benzyloxyphenyl)-1-(1-propyl-piperidin-3-ylcarbamoyl)-ethyl]-amide;

2-(Isopropyl-methyl-amino)-methyl-pentanoic acid [2-(4-benzyloxyphenyl)-1-(1-propyl-piperidin-3-ylcarbamoyl)-ethyl]-amide;

2-[(4-tertButyl-benzyl-)-methyl-amino]-4-methyl-pentanoic acid [2-(4-benzyloxyphenyl)-1-(1-propyl-piperidin-3-ylcarbamoyl)-ethyl]-amide;

2-[(4-Dimethylamino-benzyl)-methyl-amino]-4-methyl-pentanoic acid [2-(4-benzyloxy phenyl)-1-(1-propyl-piperidin-3-ylcarbamoyl)-ethyl]-amide;

[S,(R*,R*)]-4-Methyl-2-piperidin-1-yl-pentanoic acid [2-(4-benzyloxy-phenyl)-1-tert-butylcarbamoyl-ethyl]-amide; and

[S,(R*,R*)]-4-Methyl-2-morpholin-4-yl-pentanoic acid [2-(4-benzyloxy-phenyl)-1-tert-butylcarbamoyl-ethyl]-amide monohydrochloride.

21. The compounds:

[S-(R*,R*)]-2-Dimethylamino-4-methyl-pentanoic acid {1-tert-butylcarbamoyl-2-[4-(pyridin-3-ylmethoxy)-phenyl]-ethyl}-amide;

[S-(R*,R*)]-2-(Cyclohexyl-methyl-amino)-4-methyl-pentanoic acid {1-tert-butylcarbamoyl-2-[4-(pyridin-3-ylmethoxy)-phenyl]-ethyl}-amide;

[S-(R*,R*)]-4-Methyl-2-[methyl-(3-methyl-butyl)-amino]-pentanoic acid {1-tert-butylcarbamoyl-2-[4-(pyridin-3-ylmethoxy)-phenyl]-ethyl}-amide;

[S-(R*,R*)]-2-[(4-tert-Butyl-benzyl)-methyl-amino]-4-methyl-pentanoic acid {1-tert-butylcarbamoyl-2-[4-(pyridin-3-ylmethoxy)-phenyl]-ethyl}-amide;

[S-(R*,R*)]-2-[(3-Methoxy-benzyl)-methyl-amino]-4-methyl-pentanoic acid [2-(4-benzyloxyphenyl)-1-tert-butylcarbamoyl-ethyl]-amide;

[S-(R*,R*)]-2-[(2-Methoxy-benzyl)-methyl-amino]-4-methyl-pentanoic acid [2-(4-benzyloxyphenyl)-1-tert-butylcarbamoyl-ethyl]-amide;

[S-(R*,R*)]-2-[(4-Chloro-benzyl)-methyl-amino]-4-methyl-pentanoic acid [2-(4-benzyloxyphenyl)-1-tert-butylcarbamoyl-ethyl]-amide;

[S-(R*,R*)]-2-[(3-Chloro-benzyl)-methyl-amino]-4-methyl-pentanoic acid [2-(4-benzyloxyphenyl)-1-tert-butylcarbarnoyl-ethyl]-amide;

[S-(R*,R*)]-2-[(2-Chloro-benzyl)-methyl-amino]-4-methyl-pentanoic acid [2-(4-benzyloxyphenyl)-1-tert-butylcarbamoyl-ethyl]-amide; and

[S-(R*,R*)]-4-Methyl-2-[methyl-(4-methylsulfanyl-benzyl)-amino]-pentanoic acid [2-(4-benzyloxyphenyl)-1-tert-butylcarbamoyl-ethyl]-amide.

22. The compounds:

[S-(R*,R*)]-4-Methyl-2-[methyl-(tetrahydro-pyran-4-yl)-amino]-pentanoic acid {2-(4-benzyloxy-phenyl)-1-[3-(2-oxo-pyrrolidin-1-yl)-propylcarbamoyl]-ethyl}-amide;

[S-(R*,R*)]-4-Methyl-2-[methyl-(3-methyl-butyl)-amino]-pentanoic acid {2-(4-benzyloxy-phenyl)-1-[3-(2-oxo-pyrrolidin-1-yl)-propylcarbamoyl]-ethyl}-amide;

[S-(R*,R*)]-2-(Isopropyl-methyl-amino)-4-methyl-pentanoic acid {2-(4-benzyloxy-phenyl)-1-[3-(2-oxo-pyrrolidin-1-yl)-propylcarbamoyl]-ethyl}-amide;

[S-(R*,R*)]-2-[(3-Hydroxy-butyl)-methyl-amino]-4-methyl-pentanoic acid {2-(4-benzyloxy-phenyl)-1-[3-(2-oxo-pyrrolidin-1-yl)-propylcarbamoyl]-ethyl}-amide;

[S-(R*,R*)]-2-[(4-tert-Butyl-benzyl)-methyl-amino]-4-methyl-pentanoic acid {2-(4-benzyloxy-phenyl)-1-[3-(2-oxo-pyrrolidin-1-yl)-propylcarbamoyl]-ethyl}-amide;

[S-(R*,R*)]-2-[(4-Dimethylamino-benzyl)-methyl-amino]-4-methyl-pentanoic acid {2-(4-benzyloxy-phenyl)-1-[3-(2-oxo-pyrrolidin-1-yl)-propylcarbamoyl]-ethyl}-amide;

[S-(R*,R*)]-2-(Isopropyl-methyl-amino)-4-methyl-pentanoic acid [2-(4-benzyloxy-phenyl)-1-(2-piperidin-1-yl-ethylcarbamoyl)-ethyl]-amide;

[S-(R*,R*)]-2-[(3-Hydroxy-butyl)-methyl-amino]-4-methyl-pentanoic acid [2-(4-benzyloxy-phenyl)-1-(2-piperidin-1-yl-ethylcarbamoyl)-ethyl]-amide;

[S-(R*,R*)]-2-[(4-tert-Butyl-benzyl)-methyl-amino]-4-methyl-pentanoic acid [2-(4-benzyloxy-phenyl)-1-(2-piperidin-1-yl-ethylcarbamoyl)-ethyl]-amide; and

[S-(R*,R*)]-2-[(4-Dimethylamino-benzyl)-methyl-amino]-4-methyl-pentanoic acid [2-(4-benzyloxy-phenyl)-1-(2-piperidin-1-yl-ethylcarbamoyl)-ethyl]-amide.

23. The compounds:

[S-(R*,R*)]-4-Methyl-2-[methyl-(tetrahydro-pyran-4-yl)-amino]-pentanoic acid [1-(4-benzyloxy-benzyl)-2-[1,4']bipiperidinyl-1'-yl-2-oxo-ethyl]-amide;

[S-(R*,R*)]-4-Methyl-2-[methyl-(3-methyl-butyl)-amino]-pentanoic acid [1-(4-benzyloxy-benzyl)-2-[1,4']bipiperidinyl-1'-yl-2-oxo-ethyl]-amide;

[S-(R*,R*)]-2-(Isopropyl-methyl-amino)-4-methyl-pentanoic acid [1-(4-benzyloxy-benzyl)-2-[1,4']bipiperidinyl-1'-yl-2-oxo-ethyl]-amide;

2-[(3-Hydroxy-butyl)-methyl-amino]-4-methyl-pentanoic acid [1-(4-benzyloxy-benzyl)-2-[1,4']bipiperidinyl-1'-yl-2-oxo-ethyl]-amide;

[S-(R*,R*)]-2-[(4-tert-Butyl-benzyl)-methyl-amino]-4-methyl-pentanoic acid [1-(4-benzyloxy-benzyl)-2-[1,4']bipiperidinyl-1'-yl-2-oxo-ethyl]-amide;

[S-(R*,R*)]-2-[(4-Dimethylamino-benzyl)-methyl-amino]-4-methyl-pentanoic acid [1-(4-benzyloxy-benzyl)-2-[1,4']bipiperidinyl-1'-yl-2-oxo-ethyl]-amide;

[S-(R*,R*)]-2-[(4-tert-Butyl-benzyl)-methyl-amino]-4-methyl-pentanoic acid [1-(2-benzylamino-ethylcarbamoyl)-2-(4-benzyloxy-phenyl)-ethyl]-amide; and

[S-(R*,R*)]-2-[(4-Dimethylamino-benzyl)-methyl-amino]-4-methyl-pentanoic acid [1-(2-benzylamino-ethylcarbamoyl)-2-(4-benzyloxy-phenyl)-ethyl]-amide.

24. The compounds:

[S-(R*,R*)]-4-Methyl-2-[methyl-(tetrahydro-pyran-4-yl)-amino]-pentanoic acid [1-(2-benzylamino-ethylcarbamoyl)-2-(4-benzyloxy-phenyl)-ethyl]-amide;

[S-(R*,R*)-4-Methyl-2-[methyl-(3-methyl-butyl)-amino]-pentanoic acid [1-(2-benzylamino-ethylcarbamoyl)-2-(4-benzyloxy-phenyl)-ethyl]-amide;

[S-(R*,R*)]-2-[(3-Hydroxy-butyl)-methyl-amino]-4-methyl-pentanoic acid [2-(4-benzyloxy-phenyl)-1-(1-propyl-piperidin-3-ylcarbamoyl)-ethyl]-amide; and

[S-(R*,R*)]-4-Methyl-2-methyl-(3-methyl-butyl)-amino]-pentanoic acid [2-(4-benzyloxy-phenyl)-1-(1-propyl-piperidin-3-ylcarbamoyl)-ethyl]-amide.

25. The compounds:

[S-(R*,R*)]-2-(Isopropyl-methyl-amino)-4-methyl-pentanoic acid [2-(4-benzyloxy-phenyl)-1-(3-imidazol-1-yl-propylcarbamoyl)-ethyl]-amide;

2-[(3-Hydroxy-butyl)-methyl-amino]-4-methyl-pentanoic acid [2-(4-benzyloxy-phenyl)-1-(1,1-bis-hydroxymethyl-propylcarbamoyl)-ethyl]-amide;

[S-(R*,R*)]-2-[(4-tert-Butyl-benzyl)-methyl-amino]-4-methyl-pentanoic acid [2-(4-benzyloxy-phenyl)-1-(1,1-bis-hydroxymethyl-propylcarbamoyl)-ethyl]-amide;

[S-(R*,R*)]-2-[(4-Dimethylamino-benzyl)-methyl-amino]-4-methyl-pentanoic acid [2-(4-benzyloxy-phenyl)-1-(1,1-bis-hydroxymethyl-propylcarbamoyl)-ethyl]-amide;

[S-(R*,R*)]-2-[(4-tert-Butyl-benzyl)-methyl-amino]-4-methyl-pentanoic acid [2-(4-benzyloxy-phenyl)-1-(3-imidazol-1-yl-propylcarbamoyl)-ethyl]-amide;

[S-(R*,R*)]-2-[(4-Dimethylamino-benzyl)-methyl-amino]-4-methyl-pentanoic acid [2-(4-benzyloxy-phenyl)-1-(3-imidazol-1-yl-propylcarbamoyl)-ethyl]-amide;

[S-(R*,R*)]-2-(Isopropyl-methyl-amino)-4-methyl-pentanoic acid [2-(4-benzyloxy-phenyl)-1-(3-imidazol-1-yl-propylcarbamoyl)-ethyl]-amide; and

[S-(R*,R*)]-2-[(3-Hydroxy-butyl)-methyl-amino]-4-methyl-pentanoic acid [2-(4-benzyloxy-phenyl)-1-(3-imidazol-1-yl-propylcarbamoyl)-ethyl]-amide.

26. The compounds:

[S-(R*,R*)]-2-(Isopropyl-methyl-amino)-4-methyl-pentanoic acid [2-(4-benzyloxy-phenyl)-1-(2-hydroxy-1,1-dimethyl-ethylcarbamoyl)-ethyl]-amide;

2-[(3-Hydroxy-butyl)-methyl-amino]-4-methyl-pentanoic acid [2-(4-benzyloxy-phenyl)-1-(2-hydroxy-1,1-dimethyl-ethylcarbamoyl)-ethyl]-amide;

2-[(4-tert-Butyl-benzyl)-methyl-amino]-4-methyl-pentanoic acid [2-(4-benzyloxy-phenyl)-1-(2-hydroxy-1,1-dimethyl-ethylcarbamoyl)-ethyl]-amide;

2-[(4-Dimethylamino-benzyl)-methyl-amino]-4-methyl-pentanoic acid [2-(4-benzyloxy-phenyl)-1-(2-hydroxy-1,1-dimethyl-ethylcarbamoyl)-ethyl]-amide; and 2-[(3-Hydroxy-butyl)-methyl-amino]4-methyl-pentanoic acid [2-(4-benzyloxy-phenyl)-1-(1-methoxymethyl-propylcarbamoyl)-ethyl]-amide.

27. The compounds:

[S-(R*,R*)]-4-Methyl-2-[methyl-(3-methyl-butyl)-amino]-pentanoic acid [2-(4-benzyloxy-phenyl)-1-(2-hydroxy-1,1-dimethyl-ethylcarbamoyl)-ethyl]-amide;

[S-(R*,R*)]-4-methyl-2-(3-methyl-butylamino)-pentanoic acid [2-(4-phenethyl-phenyl)-1-tert-butylcarbamoyl-ethyl] amide;

[S-(R*,R*)]-4-methyl-2-(3-methyl-butylamino)-pentanoic acid [2-(4-(2-cyclohexyl-ethyl)-phenyl)-1-tert-butylcarbamoyl-ethyl] amide;

[S-(R*,R*)]-4-methyl-2-(3-methyl-butylamino)-pentanoic acid [2-(4-(2-cyclopentyl-ethyl)-phenyl)-1-tert-butylcarbamoyl-ethyl] amide; and

[S-(R*,R*)]-4-methyl-2-(3-methyl-butylamino)-pentanoic acid [2-(4-(2-cyclohexyl-ethyl)-phenyl)-1-(1,1-bis-hydroxymethyl-propylcarbamoyl)-ethyl] amide.

28. The compounds:

4-Methyl-2-[methyl-(tetrahydro-pyran-4-yl)-amino]-pentanoic acid [2-(4-benzyloxyphenyl)-1-(1-methoxymethyl-propylcarbamoyl)-ethyl]-amide;

4-Methyl-2-[methyl-(3-methylbutyl)-amino]-pentanoic acid [2-(4-benzyloxy-phenyl)-1-(1-methoxymethyl-propylcarbamoyl)-ethyl]-amide;

2-(Isopropyl-methyl-amino)-4-methyl-pentanioc acid [2-(4-benzyloxyphenyl)-1-(1-methoxymethyl-propylcarbamoyl)-ethyl]-amide;

2-[(4-tert-butyl-benzyl)-methyl-amino]-4-methyl-pentanoic acid [2-(4-benzyloxyphenyl)-1-(1-methoxymethyl-propylcarbamoyl)-ethyl]-amide;

2-[(4-Dimethylamino-benzyl)-methyl-amino]-4-methyl-pentanoic acid [2-(4-benzyloxyphenyl)-1-(1-methoxymethyl-propylcarbamoyl)-ethyl]-amide;

4-Methyl-2-[methyl-tetrahydropyran-4-yl)-amino]-pentanoic acid [2-(4-benzyloxyphenyl)-1-(1-propyl-piperidin-3-ylcarbamoyl)-ethyl]-amide;

4-Methyl-2-[methyl-(3-methyl-butyl-amino]-pentanoic acid [2-(4-benzyloxyphenyl)-1-(1-propyl-piperidin-3-ylcarbamoyl)-ethyl]-amide;

2-(Isopropyl-methyl-amino)-methyl-pentanoic acid [2-(4-benzyloxyphenyl)-1-(1-propyl-piperidin-3-ylcarbamoyl)-ethyl]-amide;

2-[(4-tertButyl-benzyl-)-methyl-amino]-4-methyl-pentanoic acid [2-(4-benzyloxyphenyl)-1-(1-propyl-piperidin-3-ylcarbamoyl)-ethyl]-amide; and 2-[(4-Dimethylamino-benzyl)-methyl-amino]-4-methyl-pentanoic acid [2-(4-benzyloxyphenyl)-1-(1-propyl-piperidin-3-ylcarbamoyl)-ethyl]-amide.

29. The compounds:

[S-(R*,R*)]-4-Methyl-2-morpholin-4-yl-pentanoic acid [2-(4-benzyloxy-phenyl)-1-(2-morpholin-4-yl-ethylcarbamoyl)-ethyl]-amide;

[S-(R*,R*)]-4-Methyl-2-morpholin-4-yl-pentanoic acid [2-(4-benzyloxy-phenyl)-1-(2-pyridin-2-yl-ethylcarbamoyl)-ethyl]-amide;

[S-(R*,R*)]-4-Methyl-2-morpholin-4-yl-pentanoic acid [2-(4-benzyloxy-phenyl)-1-(3-imidazol-1-yl-propylcarbamoyl)-ethyl]-amide;

[S-(R*,R*)]-4-Methyl-2-morpholin-4-yl-pentanoic acid [2-(4-benzyloxy-phenyl)-1-(2-thiomorpholin-4-yl-ethylcarbamoyl)-ethyl]-amide;

[S-(R*,R*)]-4-Methyl-2-morpholin4-yl-pentanoic acid [2-(4-benzyloxy-phenyl)-1-(2-hydroxy-1,1-dimethyl-ethylcarbamoyl)-ethyl]-amide;

[S-(R*,R*)]-4-Methyl-2-morpholin-4-yl-pentanoic acid [2-(4-benzyloxy-phenyl)-1-(1,1-bis-hydroxymethyl-propyl-carbamoyl)-ethyl]-amide;

[S-(R*,R*)]-4-Methyl-2-morpholin-4-yl-pentanoic acid [2-(4-benzyloxy-phenyl)-1-(2-pyrrolidin-1-yl-ethylcarbamoyl)-ethyl]-amide;

[S-(R*,R*)]-4-Methyl-2-morpholin-4-yl-pentanoic acid [2-(4-benzyloxy-phenyl)-1-(4-hydroxypiperidinylcarbamoyl)-ethyl]-amide;

[S-(R*,R*)]-4-Methyl-2-(tetrahydropyran-4-yl-amino)-pentanoic acid [2-(4-benzyloxy-phenyl)-1-(2-morpholin-4-yl-ethylcarbamoyl)-ethyl]-amide;

[S-(R*,R*)]-4-Methyl-2-(tetrahydropyran-4-yl-amino)-pentanoic acid [2-(4-benzyloxy-phenyl)-1-(-(2-pyridin-2-yl-ethylcarbamoyl)-ethyl]-amide;

[S-(R*,R*)]-4-Methyl-2-(tetrahydropyran-4-yl-amino)-pentanoic acid [2-(4-benzyloxy-phenyl)-1-(3-imidazol-1-yl-propylcarbamoyl)-ethyl]-amide;

[S-(R*,R*)]-4-Methyl-2-(tetrahydropyran-4-yl-amino)-pentanoic acid [2-(4-benzyloxy-phenyl)-1-(2-pyrrolidine-1-yl-ethylcarbamoyl)-amide;

[S-(R*,R*)]-4-Methyl-2-(tetrahydropyran-4-yl-amino)-pentanoic acid [2-(4-benzyloxy-phenyl)-1-(4-hydroxy-piperinylcarbamoyl]-amide;

[S-(R*,R*)]-2-Dimethylamino-4-methyl-pentanoic acid [2-(4-benzyloxy-phenyl)-1-(2-morpholin-4-yl-ethylcarbamoyl)-ethyl]-amide;

[S-(R*,R*)]-2-Dimethylamino-4-methyl-pentanoic acid [2-(4-benzyloxy-phenyl)-1-(2-(2-aminoethyl)pyridine carbamoyl)-ethyl]-amide;

[S-(R*,R*)]-2-Dimethylamino-4-methyl-pentanoic acid [2-(4-benzyloxy-phenyl)-1-(3-imidazol-1-yl-propylcarbamoyl)-ethyl]-amide;

[S-(R*,R*)]-2-Dimethylamino-4-methyl-pentanoic acid [2-(4-benzyloxy-phenyl)-1-(thiomorpholinecarbamol)-ethyl)-ethyl]-amide;

[S-(R*,R*)]-2-Dimethylamino-4-methyl-pentanoic acid [2-(4-benzyloxy-phenyl)-1-(2-aminopropan-1-ol carbamoyl)-ethyl]-amide;

[S-(R*,R*)]-2-Dimethylamino-4-methyl-pentanoic acid [2-(4-benzyloxy-phenyl)-1-(2-hydroxymethylbutan-1-ol)-ethyl]-amide;

[S-(R*,R*)]-2-Dimethylamino-4-methyl-pentanoic acid [2-(4-benzyloxy-phenyl)-1-(1-methoxymethyl-propylcarbamoyl)-ethyl]-amide;

[S-(R*,R*)]-2-Dimethylamino-4-methyl-pentanoic acid [2-(4-benzyloxy-phenyl)-1-(2-pyrrolidin-1-yl-ethylcarbamoyl)-ethyl]-amide; and

[S-(R*,R*)]-2-Dimethylamino-4-methyl-pentanoic acid {2-(4-benzyloxy-phenyl)-1-[2-(2-hydroxy-ethylamino)-ethylcarbamoyl]-ethyl}-amide.

* * * * *